United States Patent
Horwell et al.

(10) Patent No.: US 6,194,437 B1
(45) Date of Patent: Feb. 27, 2001

(54) NON-PEPTIDE BOMBESIN RECEPTOR ANTAGONISTS

(75) Inventors: David Christopher Horwell, Cambridge; Martyn Clive Pritchard, Cambridgeshire, both of (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/230,933

(22) PCT Filed: Aug. 6, 1997

(86) PCT No.: PCT/US97/13871

§ 371 Date: Feb. 3, 1999

§ 102(e) Date: Feb. 3, 1999

(87) PCT Pub. No.: WO98/07718

PCT Pub. Date: Feb. 26, 1998

Related U.S. Application Data

(60) Provisional application No. 60/024,323, filed on Aug. 22, 1996.

(51) Int. Cl.$^7$ ............... C07D 401/12; C07D 213/56; A61K 31/395; A61K 31/44
(52) U.S. Cl. ............ 514/332; 514/341; 514/352; 514/357; 514/337; 514/400; 514/419; 514/616; 546/265; 546/275.1; 546/277.4; 546/336; 548/338.1; 548/503; 564/155
(58) Field of Search ................. 546/304, 329, 546/265, 277.4, 275.1, 336; 514/352, 357, 337, 341, 332, 400, 419, 616; 564/152; 548/338.1, 503

(56) References Cited

U.S. PATENT DOCUMENTS

| | | |
|---|---|---|
| 4,000,297 | 12/1976 | Rovati et al. .............. 424/274 |
| 4,518,587 | 5/1985 | Laruelle et al. .............. 514/19 |
| 4,639,451 | 1/1987 | Katakami et al. ............ 514/247 |

(List continued on next page.)

FOREIGN PATENT DOCUMENTS

| | | |
|---|---|---|
| 0288965 | 11/1988 | (EP) . |
| 415413 | * 3/1991 | (EP) . |
| 0632036 | 1/1995 | (EP) . |
| 07101929 | 10/1993 | (JP) . |
| 9204045 | 3/1992 | (WO) . |
| 93/01169 | * 1/1993 | (WO) . |
| 9324458 | 12/1993 | (WO) . |
| 94/04494 | * 3/1994 | (WO) . |

OTHER PUBLICATIONS

Blommaert, J. Med. Chem, 36, pp. 2868–2877, 1993.*
Sartori et al, Eur. J. Med. Chem. vol. 29, pp. 431–439, 1994.*
Schogl, Chemical Abstracts, vol. 51, No. 11, Abstract 8074g, Jun. 1957.*

(List continued on next page.)

Primary Examiner—Zinna Northington Davis
(74) Attorney, Agent, or Firm—Elizabeth M. Anderson

(57) ABSTRACT

The compounds of the instant invention are novel compounds of Formula I

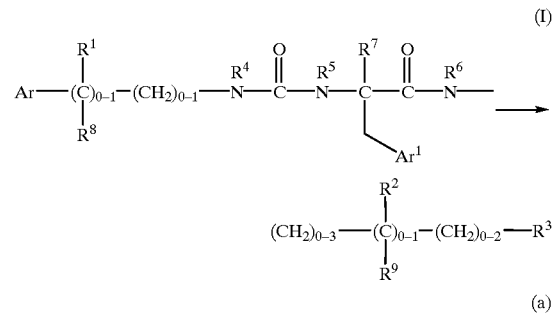

(I)

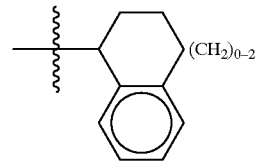

(a)

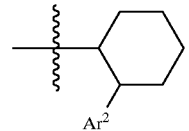

(b)

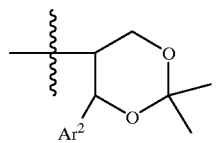

(c)

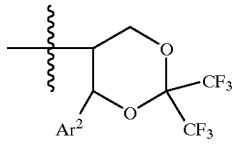

(d)

or a pharmaceutically acceptable salt thereof wherein Ar is phenyl or pyridyl unsubstituted or substituted. $Ar^1$ can be independently selected from Ar and can also include pyridyl-N-oxide, indolyl, imidazole, and pyridyl; $R^3$ can be independently selected from Ar or is hydrogen, hydroxy, $NMe_2$, N-methyl-pyrrole, imidazole, tetrazole, thiazole (a), (b), (c), or (d), wherein $Ar^2$ is phenyl or pyridyl. The instant compounds antagonize the bombesin receptors in mammals and are therefore effective in treating and/or preventing depression, psychoses, seasonal affective disorders, cancer, feeding disorders, gastrointestinal disorders, inflammatory bowel disease, sleep disorders, and memory impairment.

20 Claims, No Drawings

U.S. PATENT DOCUMENTS

| | | | |
|---|---|---|---|
| 4,965,263 | 10/1990 | Nishina et al. | 514/247 |
| 5,200,408 | 4/1993 | Bru-Maginez et al. | 514/237.2 |
| 5,340,798 | 8/1994 | Nutt et al. | 514/18 |
| 5,346,907 | 9/1994 | Kerwin, Jr. et al. | 514/312 |
| 5,378,803 | 1/1995 | Morgan et al. | 530/317 |
| 5,455,262 | 10/1995 | Schwartz et al. | 514/418 |
| 5,470,834 | 11/1995 | Schwartz et al. | 514/19 |
| 5,472,978 | 12/1995 | Baker et al. | 514/443 |
| 5,495,047 | 2/1996 | Van Niel et al. | 564/346 |
| 5,594,022 * | 1/1997 | Horwell et al. | 514/419 |
| 5,610,183 | 3/1997 | Owens et al. | 514/539 |
| 5,629,347 | 5/1997 | Swain et al. | 514/620 |

OTHER PUBLICATIONS

Medenica et al., "Polypeptide Levels Increase During Acute Onset of Hepatic Porphyrias", *Cellular and Molecular Biology*, vol. 41, No. 1, 1997, 9–27.

Kulkosky, "Bombesin and Ceruletide–induced Grooming and Inhibition of Ingestion in the Rat", *Ann. N.Y. Acad. Sci*, vol. 525, 1988, 201–218.

Hurel et al., "Treatment of pulmonary hypertension with bombesin antagonist", *Lancet*, vol. 348, 1996, 1243.

Anastasi et al., "Isolation and Structure of Bombesin and Alytesin, two Analogous Active Peptides from the Skin of the European Amphibians Bombina and Alytes", *Experiencia*, vol. 27, 1971, 166–167.

Dutta, "Bombesin/Gastrin–Releasing Peptide", *Small Peptides; Chemistry, Biology, and Clinical Studies*, Chapter 2, 1993, 66–82.

Battey and Wada, "Two distinct receptor subtypes for mammalian bombesin–like peptides", *TINS*, vol. 14, No. 12, 1991, 524–528.

Brown et al., "Bombesin–like activity: radioimmunologic assessment in biological tissues", *Life Sciences*, vol. 23, 1978, 2721–2728.

Walsh et al., "Bombesin–like peptides in mammals", *Federation Proceedings*, vol. 38, 1979, 2315–2319.

Taylor et al., "Progress in the Development of Competitive Bombesin Antagonists", *Ann. N.Y. Acad. Sci.*, vol. 547, 1988, 150–157.

Rozengurt, "Bombesin–Induction of Cell Proliferation in 3T3 Cells", *Ann. N.Y. Acad. Sci.*, vol. 547, 1988, 277–292.

Cuttitta et al., "Bombesin–like peptides can function as autocrine growth factors in human small–cell lung cancer", *Nature*, vol. 316, 1985, 823–826.

Kozacko et al., "Bombesin antagonist prevents $CO_2$ laser–induced promotion of oral cancer", *Proc. Natl. Acad. Sci USA*, vol. 93, 1996, 2953–2957.

Ghatei et al., "Bombesin: Action on Gut Hormones and Calcium in Man", *Journal of Clinical Endocrinolology and Metabolism*, vol. 54, No. 5, 1982, 980–985.

Erspamer and Melchiorri, "Active polypeptides of the amphibian skin and their synthetic analogues", *Pure Appl. Chem.*, vol. 35, 1973, 463–494.

Kulkosky et al., "Behavioral Effects of Bombesin Administration in Rats", *Physiology & Behavior*, vol. 28, 1982, 505–512.

Gmerek and Cowan, "Studies on Bombesin–Induced Grooming in Rats", *Peptides*, vol. 4, 1983, 907–913.

Cowan, "Behavioral Effects of Bombesin", *Ann. N.Y. Acad. Sci.*, vol. 547, 1988, 204–209.

Brown et al., "Bombesin: Central Nervous System Actions to Affect the Autonomic Nervous System", *Ann. N.Y. Acad. Sci.*, vol. 547, 1988, 174–182.

Kirkham et al., "Meal Pattern Analysis in Rats Reveals Partial Agonist Activity of the Bombesin Receptor Antagonist BW2258U89", *Pharmacology Biochemistry and Behavior*, vol. 52, No. 1, 1995, 101–106.

Ladenheim et al., "Blockade fo feeding inhibition by neuromedin B using a selective receptor antagonist", *European Journal of Pharmacology*, vol. 271, 1994, R7–R9.

Albers et al., "Interaction of Colocalized Neuropeptides: Functional Significance in the Circadian Timing System", *The Journal of Neuroscience*, vol. 11, No. e, 1991, 846–851.

Walsh, "Peptides as regulators of gastric acid secretion", *Ann. Rev. Physiol.*, vol. 50, 1988, 41–63.*

Lebacq–Verheyden et al., "Bombesin and Gastrin–Releasing Peptide: Neuropeptides, Secretogogues, and Growth Factors", *Handbook of Experimental Pharmacology*, vol. 95 (Part II), 1990, 71–124.*

Pert et al., "Bombesin: receptor distribution in brain and effects on nociception and locomotor activity", *Brain Research*, vol. 193, 1980, 209–220.*

Flood and Morley, "Effects of bombesin and gastrin–releasing peptide on memory processing", *Brain Research*, vol. 460, 1988, 314–322.*

Pow and Crook, "Rapid postmortem changes in the cellular localisation of amino acid transmitters in the retina as assessed by immunocytochemistry", *Brain Research*, vol. 653, 1994, 199–209.*

Pinnock and Woodruff, "Bombesin excites a subpopulation of 5–hydroxytryptamine–sensitive neurones in the rat dorsal raphe nucleus in vitro", *Journal of Physiology*, vol. 440, 1991, 55–65.*

Zinner and Bock, "Zur Kenntnis der UGI–Reaktion mit Hydriznen, II", *Arch. Pharmaz.*, vol. 304, No. 12, 1971, 933–943.*

Beaver et al., "Preparation and bacteriostatic activity of substituted ureas", Chemical Abstracts, vol. 51, column 11268, 1972.*

Ye et al., "A Recombinant Human Stromelysin Catalytic Domain Identifying Tryptophan Derivatives as Human Stromelysin Inhibitors", *J. Med. Chem.*, vol. 37, 1994, 206–209.*

Galaverna et al., "Diaminomethane dihydrochloride, a novel reagent for the synthesis of primary amides of amino acids and peptides from active esters", *Int. J. Peptide Protein Res.*, vol. 42, 1993, 53–57.*

Nozaki and Muramatsu, "Convenient Synthesis of N–Protected Amino Acid Amides", *Bull. Chem. Soc. Jpn.*, vol. 61, No. 7, 1988, 2647–2648.*

Maton et al., "Carbobenzoxy amino acids: structural requirements for cholecystokinin receptor antagonist activity", *Am. J. Physiol.*, vol. 248(4, Pt 1), 1985, G479–G484.*

Appel and Hiester, "Dichlorotris(dimethylamino)phosphorane as a Dehydratisation Reagent for the Preparation of N–Protected Amino Acid Amides", *Chem. Ber.*, vol. 116, No. 5, 1983, 2037–2040.*

Kamber et al., "The Synthesis of Cystine Peptides by Iodine Oxidation of S–Trityl–cysteine and S–Acetamidomethyl–cysteine Peptides", *Helv. Chim. Acta*, vol. 63, vol. 4, 1980, 899–915.*

Bajusz et al., "Synthesis of a hexapeptide, a potential inhibitor of GH–RH* liberation", *Acta Chim. (Budapest)*, vol. 76, 1973, 431–436.

Sokolovsky and Fuchs, "Reaction of tetranitromethane with tryptophan and related compounds", *FEBS Letters*, vol. 7, No. 2, 1970, 167–170.

Weinryb, "The effect of solvent viscosity on the fluorescence of tryptophan derivatives", *Biochem. Biophys. Res. Commun.*, vol. 34, No. 6, 1969, 865–868.

Weinryb and Steiner, "The Luminescence of Tryptophan and Phenylalanine Derivatives", *Biochemistry*, vol. 7, No. 7, 1968, 2488–2495.

Jelokhani–Niaraki et al., "Changes in Conformation and Antimicrobial Properties Caused by Replacement of D–Amino Acids with alpha–Aminoisobutyric Acid in the Gramicidin Backbone: Synthesis and Circular Dichroic Studies", *J. Chem. Soc. Perkin Trans. 2*, vol. 7, 1992, 1187–1193.

Boyle et al., "Rational Design of High Affinity Tachykinin $NK_1$ Receptor Antagonists", *Bioorganic & Medicinal Chemistry*, vol. 2, No. 5, 1994, 357–370.

Horwell et al., "Quantitative Structure–Activity Relationships (QSARs) of N–Terminus Fragments of NK1 Tachykinin Antagonists: A Comparison of Classical QSARs and Three–Dimensional QSARs from Similarity Matrices", *J. Med. Chem.*, vol. 38, No. 22, 1995, 4454–4462.

Horwell et al., "Alpha–Methyl tryptophanylphenylalanines and their arylethylamine "dipeptoid" analogues of the tetrapeptide cholecystokinin (30–33)", *Eur. J. Med. Chem.*, vol. 25, No. 1, 1990, 53–60.

Blommaert et al., "Cholecystokinin Peptidomimetics as Selective CCK–B Antagonists: Design, Synthesis, and in Vitro and in Vivo Biochemical Properties", *J. Med. Chem.*, vol. 36, No. 20, 1993, 2868–2877.

Rizzo and Jäckle, "Side–Chain vs. Main–Chain Conformational Flexibility in Aromatic Dipeptides", *J. Am. Chem. Soc.*, vol. 105, No. 13, 1983, 4195–4205.

Westerhuis et al., "Enzymatic synthesis of a peptide bond between a tryptic fragment of horse heart cytochrome c and a synthetic model peptide", *Recl. Trav. Chim. Pays–Bas*, vol. 99, No. 12, 1980, 400–403.

Dutta and Morley, "Polypeptides. Part XII. The Preparation of 2–Pyridyl Esters and Their Use in Peptide Synthesis", *J. Chem. Soc. C*, vol. 17, 1971, 2896–2902.

Saito et al., "Chemistry of Diborane and Sodium Borohydride. VII. Reduction of a–Amino Acid Amides with Sodium Borohydride", *Chem. Pharm. Bull*, vol. 18, No. 9, 1970, 1731–1736.

Milne and Most, Jr., "Peptide Synthesis via Oxidation of N–Acyl–alpha–amino Acid Phenylhydrazides. II. Benzyloxycarbonyl Peptide Phenylhydrazides", *J. Org. Chem.*, vol. 33, No. 1, 1968, 169–175.

Neklyudov et al., "Synthesis and pharmacological activity of aminoalkyl derivatives of substituted tryptamines", *Khim.–Farm. Zh.*, vol. 8, No. 6, 1974, 7–11.

Kashima et al., "Amino alcohols as C–Terminal Protecting Groups in Peptide Synthesis", *J. Chem. Soc. Perkin Trans. I*, vol. 3, 1988, 535–539.

Nesvadba, "Aminosäure–beta–naphthylamide zur Aktivitätsbestimmung proteolytischer Fermente", *Monatsch.*, vol. 93, 1962, 386–396.

Sarges and Witkop, "Gramicidin A. V. The Structure of Valine– and Isoleucine–gramicidin A", *J. Amn. Chem. Soc.*, vol. 87, No. 9, 1965, 2011–2020.

Scoffone et al., "Oxidative modification of tryptophan residues in peptides", *Peptides, Proc. European, Symp.*, $6^{th}$, Athens, 1963, Pub. 1966, 183–188.

Barth, "Über den Nachweis des Aminolyseverlaufes von Cbo–Aminosäure–4–(phenylazo)–phenylestern mit Hilfe der Dünnschichtchromatographie", *J. Prakt. Chem.*, vol. 27, Nos. 3–4, 1965, 181–188.

Krainova et al., "Peptides containing unnatural amino acids. II. Peptides of DL–beta–pyridyl–alpha–alanine with glycine", *Zh. Obshch. Khim.*, vol. 41, No. 7, 1971, 1617–1619.

\* cited by examiner

NON-PEPTIDE BOMBESIN RECEPTOR ANTAGONISTS

This application is derived from application number PCT/US97/13871 filed on Aug. 6, 1997, under 35 U.S.C. §371, and claims benefit of priority from U.S. provisional application No. 60/024,323 filed on Aug. 22, 1996.

BACKGROUND OF THE INVENTION

Bombesin is a 14-amino acid peptide originally isolated from the skin of the European frog Bombina bombina (Anastasi A., et a., *Experientia,* 1971;27:166). It belongs to a class of peptides which share structural homology in their C-terminal decapeptide region (Dutta A. S. Small Peptides; Chemistry, Biology, and Clinical Studies, Chapter 2, pp 66–82). At present, two mammalian bombesin-like peptides have been identified (Battey J., et a., *TINS,* 1991;14:524), the decapeptide neuromedin B (NMB) and a 23-residue amino acid, gastrin-releasing peptide (GRP). Bombesin-like immunoreactivity detected in mammalian brain (Braun M., et al., *Life. Sci.,* 1978;23:2721) and GI tract (Walsh J. H., et al., *Fed. Proc. Fed. Am. Soc. Exp. Biol.,* 1979;38:2315) together with the more recent studies measuring mRNA levels in rat brain (Battey J., et al., *TINS,* 1991;14:524), point to the widespread distribution of both NMB and GRP in mammalian peripheral and central nervous systems.

NMB and GRP are believed to mediate a variety of biological actions via actin upon the corresponding bombesin receptors including their action as autocrine growth factors in human small cell lung carcinoma and other cancers (Taylor J. E., et al., *Ann. N.Y. Acad. Sci.,* 1988;547:350; Rozengurt E., Ibid., 277; Cuttitta F., et al., *Nature,* 1985;316:823; Kozacko M. F., et al., *Proc. Natl. Acad. Sci. USA,* 1996;93:2953), secretion of other neuropeptides and hormones (Ghatei M. A., et al.,*J. Clin. Endocrinol. Metab.,* 1982;54:98), contraction of smooth muscle (Erspamer V., et al.,*Pure Appl. Chem.,* 1973;35:463), behavioral effects (Kulkosky P. J. et al., *Physiol. Behav.* 1982;28:505; Gmerek D. E., et al., *Peptides,* 1983;4:907; Cowan A.,*Ann. N.Y. Acad. Sci.,* 1988;547:204), thermoregulation (Brown M. R., et al., *Ann. N.Y. Acad. Sci.,* 1988;547:174), effects on satiety (Kirkham T. C., et al., *Pharma. Biochem, Behav.,* 1995;52:101 and Ladenheim E. E., et al., *Eur. J. Pharmacol.,* 1994;271:R7), regulation of circadian rhythms (Albers H., et al., *J. Neurosci.,* 1991;11:846), regulation of gastric acid section (Walsh J. H., *Ann. Rev. Physiol.,* 1988;50:41) and gastrointestinal motility (see Lebacq-Verheyden A., et al., in *Handbook of Experimental Pharmacology,* 1990;95 (Part II) and references therein), effects on locomotor activity and nociception (Pert A., et al., *Brain Res.,* 1980;193:209), effects on memory (Flood J. F., et al., *Brain Res.,* 1988;460:314), and interaction with 5HT-containing neurones (Pinnock R. D., et al., *Brain Res.,* 1994;653:199 and Pinnock R. D., et al., *J. Physio.,* 1991;440:55).

Accordingly, compounds capable of antagonizing the effects of NMB and/or GRP at bombesin receptors will be useful in treating or preventing a variety of disorders including depression, psychoses, seasonal affective disorders, cancer, feeding disorders, gastrointestinal disorders including colitis, Crohn's disease and inflammatory bowel disease, sleeping disorders, and memory impairment.

SUMMARY OF THE INVENTION

This invention is for compounds which are bombesin receptor antagonists. The compounds have proved to be antagonists of bombesin receptors.

The compounds of the invention are those of Formula I

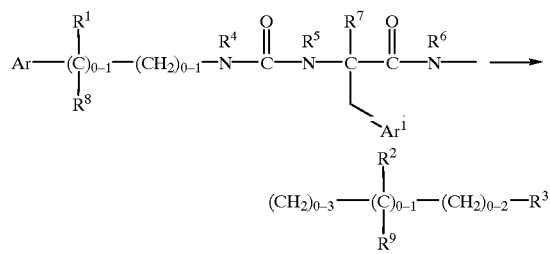

or a pharmaceutically acceptable salt thereof wherein

Ar is phenyl or pyridyl unsubstituted or substituted by from 1 to 3 substitutents selected from alkyl, halogen, alkoxy, nitro, amino, $NH_2CH_2$—, cyano, $CF_3$, —$NHCONH_2$, and $CO_2R^1$;

$R^1$ is hydrogen or straight, branched, or cyclic alkyl of from 1 to 7 carbon atoms;

$R^8$ is hydrogen or forms a ring with $R^1$ of from 3 to 7 carbon atoms;

$R^2$ is hydrogen or straight, branched, or cyclic alkyl of from 1 to 8 carbon atoms which can also contain 1 to 2 oxygen or nitrogen atoms;

$R^9$ is hydrogen or forms a ring of from 3 to 7 carbon atoms with $R^2$ which can contain an oxygen or nitrogen atom;

$Ar^1$ can be independently selected from Ar and can also include pyridyl-N-oxide, indolyl, imidazole, and pyridyl;

$R^4,R^5,R^6$, and $R^7$ are each independently selected from hydrogen and methyl;

$R^3$ can be independently selected form Ar or is hydrogen, hydroxy, $NMe_2$, N-methyl-pyrrole, imidazole, tetrazole, thiazole

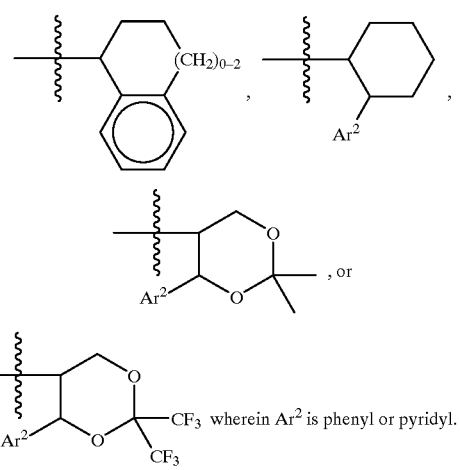

DETAILED DESCRIPTION

The compounds of the invention are those of Formula I above.

Preferred compounds are those of Formula I

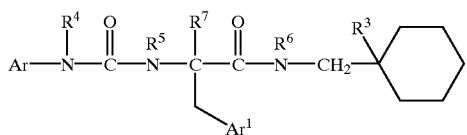

wherein
- Ar is phenyl unsubstituted or substituted with 1 or 2 substituents selected from isopropyl, chloro, nitro, and cyano;
- $R^4$, $R^5$, and $R^6$ are hydrogen;
- $R^7$ is methyl or hydrogen;
- $R^3$ is 2-pyridyl or hydroxy; and
- $Ar^1$ is indolyl, pyridyl, pyridyl-N-oxide, and imidazol.

Other preferred compounds are those of Formula I wherein
- Ar is unsubstituted phenyl;
- $R^1$ is cyclopentyl or tert-butyl;
- $R^4$ and $R^5$ are hydrogen;
- $R^7$ is methyl;
- $R^6$ is hydrogen;
- $R^3$ is phenyl with two isopropyl substituents, unsubstituted phenyl, or

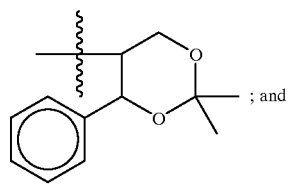; and

- $Ar^1$ is indolyl.

Other preferred compounds are those of Formula I wherein
- Ar is 2,6-diisopropyl-phenyl, 4-nitro-phenyl, and 4-cyano-phenyl;
- $R^4$, $R^5$, and $R^6$ are hydrogen;
- $R^7$ is methyl;
- $R^2$ is hydrogen or cyclohexyl; and
- $R^3$ is hydroxyl, pyridyl,

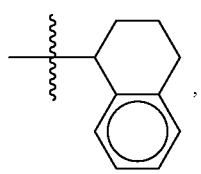,

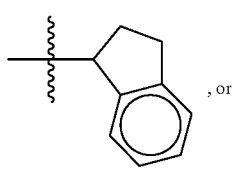, or

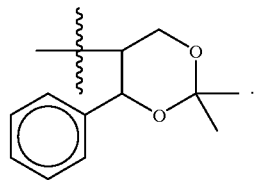.

More preferred compounds are selected from
- N-Cyclohexylmethyl-2-[3-(2,6-diisopropyl-phenyl)-ureido]-3-(1H-indol-3-yl)-2-methyl-propionamide;
- N-Cyclohexylmethyl-2-[3-(2,6-diisopropyl-phenyl)-ureido]-3-(1H-indol-3-yl)-N-methyl-propionamide;
- N-Cyclohexylmethyl-2-[3-(2,6-diisopropyl-phenyl)-1-methyl-ureido]-3-(1H-indol-3-yl)-propionamide;
- 2-[3-(2,6-Diisopropyl-phenyl)-ureido]-2-methyl-3-(1-oxy-pyridin-2-yl)-N-(1-pyridin-2-yl-cyclohexylmethyl)-propionamide;
- 2-[3-(2,6-Diisopropyl-phenyl)-ureido]-2-methyl-3-pyridin-2-yl-N-(1-pyridin-2-yl-cyclohexylmethyl)-propionamide;
- 2-[3-(2-tert-Butyl-phenyl)-ureido]-N-cyclohexylmethyl-3-(1H-indol-3-yl)-2-methyl-propionamide;
- N-Cyclohexylmethyl-2-[3-(2,6-dichloro-phenyl)ureido]-3-(1H-indol-3-yl)-2-methyl-propionamide;
- N-Cyclohexylmethyl-2-[3-(2,6-dimethoxy-phenyl)ureido]-3-(1H-indol-3-yl)-2-methyl-propionamide;
- N-Cyclohexylmethyl-2-[3-(2,6-dimethylamino-phenyl)-ureido]-3-(1H-indol-3-yl)-2-methyl-propionamide;
- [1-(Cyclohexylmethyl-carbamoyl)-2-(1H-indol-3-yl)-1-methyl-ethyl]-carbamic acid 4-nitro-benzyl ester;
- N-Cyclohexylmethyl-2-[3-(2,2-dimethyl-1-phenyl) propyl)-ureido]-3-(1H-indol-3-yl)-2-methyl-propionamide;
- {2-(1H-Indol-3-yl)-1-methyl-1-[(1-pyridin-2-yl-cyclohexylmethyl)-carbamoyl]-ethyl}-carbamic acid 3-nitro-benzyl ester;
- N-(2,2-Dimethyl-4-phenyl-[1,3]dioxan-5-yl)-3-(1H-indol-3-yl)-2-methyl-2-[3-(1-phenyl-cyclopentylmethyl)-ureido]-propionamide;
- (S)-N-(2,6-Diisopropyl-phenyl)-2-[3-(2,2-dimethyl-1-phenyl-propyl)-ureido]-3-(1H-indol-3-yl)-propionamide;
- (R)-N-(2,6-Diisopropyl-phenyl)-2-[3-(2,2-dimethyl-1-phenyl-propyl)-ureido]-3-(1H-indol-3-yl)-propionamide;
- 2-[3-(2,6-Diisopropyl-phenyl)-ureido]-N-(2,2-dimethyl-4-phenyl-[1,3]dioxan-4-yl)-3-(1H-indol-3-yl)-2-methyl-propionamide;
- N-Cyclohexyl-2-[3-(2,6-diisopropyl-phenyl)-ureido]-3-(1H-indol-3-yl)-2-methyl-propionamide;
- N-(2-Cyclohexyl-ethyl)-2-[3-(2,6-diisopropyl-phenyl)-ureido]-3-(1H-indol-3-yl)-2-methyl-propionamide;
- 2-[3-(2,6-Diisopropyl-phenyl)-ureido]-3-(1H-indol-3-yl)-2-methyl-propionamide;
- 2-[3-(2,6-Diisopropyl-phenyl)-ureido]-3-(1H-indol-3-yl)-2-methyl-N-(3-methyl-butyl)-propionamide;
- 2-[3-(2,6-Diisopropyl-phenyl)-ureido]-3-(1H-indol-3-yl)-2-methyl-N-(3-phenyl-propyl)-propionamide;
- 2-[3-(2,6-Diisopropyl-phenyl)-ureido]-3-(1H-indol-3-yl)-2-methyl-N-(1,2,3,4-tetrahydro-naphthalen-1-yl)-propionamide;

2-[3-(2,6-Diisopropyl-phenyl)-ureido]-3-(1H-indol-3-yl)-2-methyl-N-(2-phenyl-cyclohexyl)-propionamide;

2-[3-(2,6-Diisopropyl-phenyl)-ureido]-N-indan-1-yl-3-(1H-indol-3-yl)-2-methyl-propionamide;

2-[3-(2,6-Diisopropyl-phenyl)-ureido]-N-(1-hydroxy-cyclohexylmethyl)-3-(1H-indol-3-yl)-2-methyl-propionamide;

2-[3-(2,6-Diisopropyl-phenyl)-ureido]-3-(1H-indol-3-yl)-2-methyl-N-(1-pyridin-2-yl-cyclohexylmethyl)-propionamide; and 2-[3-(2,6-Diisopropyl-phenyl)-uredio]-3-(1H-indol-3-yl)-2-methyl-N-(6,7,8,9-tetrahydro-5H-benzocyclohepten-5-yl)-propionamide.

The compounds of the invention include solvates, hydrates pharmaceutically acceptable salts, and polymorphs (different crystalline lattice descriptors) of the compounds of Formula I.

Pharmaceutical compounds of compounds of the invention are also covered by the instant invention.

Method of using the compounds of the instant invention are antagonizing the effect of neuromedin B and/or gastrin-releasing peptide at bombesin receptors. Other treatments are depressing seasonal affective disorders, feeding disorders, gastrointestinal disorders, sleep disorders, memory impairment, psychoses treatment, and cancer treatment, for example, treatment of small cell lung cancers.

The compounds of the invention are those for Formula I and the pharmaceutically salts thereof. All stereoisomers of the compounds are included in the scope of the invention.

Prodrugs of the above are also contemplated such as would occur to one skilled in the art, see Bundgaard, et al., *Acta Pharm. Suec.*, 1987;24:233–246.

The alkyl groups contemplated by the invention include straight, branched, or cyclic carbon chains of from 1 to 8 carbon atoms except where specifically stated otherwise. Representative groups are methyl ethyl, propyl, isopropyl, n-propyl, n-butyl, iso-butyl, sec-butyl, tert-butyl, 2-methylhexyl, n-pentyl, 1-methylbutyl, 2,2-dimethylbutyl, 2-methylpentyl, 2,2-dimethylpropyl, n-hexyl, and the like.

The cycloalkyl groups contemplated by the invention comprise those having 3 to 7 carbon atoms. They may be substituted with from 1 to 3 groups selected from halogens, nitro, alkyl, and alkoxy.

The alkoxy groups contemplated by the invention comprise both straight and branched carbon chains of from 1 to 6 carbon atoms unless otherwise stated. Representative groups are methoxyl, ethoxy, propoxy, i-propoxy, t-butoxy, and hexoxy.

The term "halogen" is intended to include fluorine, chlorine, bromine, and iodine.

The term "Ar" is intended to include substituted or unsubstituted phenyl. The substituents include one or more substitutents such as halogens, nitro, alkyl, alkoxy, and others as specified or as would occur to one skilled in the art.

The term "amine" is free amino, alkylated amines, and acylated amines.

The compounds of the instant invention are highly selective antagonists of bombesin receptors.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The compounds of the present invention can have multiple chiral centers in the above Formula I depending on their structures. In particular, the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by conventional methods well known in the art such as conversion to a salt with an optically active compound, followed by separation by chromatography or recrystallization and reconversion to the nonsalt form.

Where it is appropriate to form a salt, the pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, gluceptate, gluconate, glutamate, glycoloylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate pamoate (embonate), pantothenate, phosphate/diphosphate, polygalacturonate, salicylate, stearate, subacetate, succinate, sulfate, tannate, tartrate, theoclate, triethiodide, benzathine, chloroprocaine, chloline, diethanolamine, ethylenediamine, meglumine, procaine, aluminum, calcium, lithium, magnesium, potassium, sodium, and zinc.

Cyclodextrin is one suitable inclusion in a pharmaceutical preparation.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of the invention have been evaluated in receptor binding assays which measure the affinity of the novel compounds in a cloned human NMB-preferring receptor ($BB_1$) assay and in a cloned human GRP-preferring receptor ($BB_2$) assay.

Protocol for Binding Assays

CHO-K1 cells stably expressing cloned human NMB and GRP receptors were routinely grown in Ham's F12 culture medium supplemented with 10% foetal calf serum and 2 mM glutamine. For binding experiments, cells were harvested by trypsinization, and stored frozen at −70° C. in Ham's F12 culture medium containing 5% DMSO until required. On the day of use, cells were thawed rapidly, diluted with an excess of culture medium, and centrifuged for 5 minutes at 2000 g. Cells were resuspended in 50 mM Tris-HCl assay buffer (pH 7.4 at 21° C., containing 0.02% BSA, 40 $\mu$g/ml bacitracin, 2 $\mu$g/mL chymostatin, 4 $\mu$g/mL leupeptin, and 2 $\mu$M phosphoramidon), counted, and polytronned (setting 5, 10 sec) before centrifuging for 10 minutes at 28,000 g. The final pellet was resuspended in assay buffer to a final cell concentration of $1.5 \times 10^5$/mL. For binding assays, 200 $\mu$L aliquots of membranes were incubated with [$^{125}$I][Tyr$^4$]bombesin (<0.1 nM) in the presence and absence of test compounds (final assay volume 250 $\mu$L) for 60 minutes and 90 minutes for NMB and GRP receptors, respectively. Nonspecific binding was defined by 1 $\mu$M bombesin. Assays were terminated by rapid filtration under vacuum onto Whatman GF/C filters presoaked in 0.2% PEI for >2 hours, and washed 50 mM Tris-HCl (pH 6.9 at 21° C.; 6×1 mL). Radioactivity bound was determined using a gamma counter. See Table 1.

The compounds of the invention have been tested in in vitro functional assays using cloned human NMB-preferring receptors expressed in CHO cells.

Protocols for functional assays:

1. Measurement of intracellular calcium levels

Culture of Chinese hamster ovary cells

Chinese hamster ovary cells were routinely grown as monolayers in Ham's F12 nutrient mixture supplemented with 10% FBS and 2 nM glutamine, and maintained at 37° C. under 5% $CO_2$. Cells were passaged every 3 to 4 days. At each passaging, cells were seeded at a density of 3 to 6 million per 175 cm$^2$ flask. For the imaging experiments, cells were plated out onto glass coverslips at a density of 5 to 10,000/cm$^2$ and usually used within 2 to 3 days after plating.

[$Ca^{2+}$] Studies in single cells

Plated cells were incubated with 2 $\mu$M Fura-2-AM for between 45 and 120 minutes at 25° C. to 29° C. This procedure loaded the cells with the dye which was hydrolysed to the free acid form inside the intact cells. Single coverslips were then mounted in a chamber on top of an inverted fluorescence microscope and perfused with a Krebs-Hepes assay buffer (composition in mM: NaCl 118, KCl 4.7, $MgSO_4$ 1.2, $CaCl^2$ 1.2, $KH^2PO^4$ 1.2, Hepes 10, glucose 11, pH 7.2 at 37° C.) {332}.

Measurements of [$Ca^{2+}$]$_i$ in individual cells were made from the fluorescence ratio (excitations 340/380 nM, emission >510 nM for Fura-2) using a specially designed filter wheel assembly, CCD camera or photomulipler tubes, and specially designed suites of software (MAGICAL OR phocal, Applied Imaging, Sunderland, UK) which samples emission following excitation at different wavelengths at regular intervals. The [$Ca^{2+}$]$_i$ could be calculated from a calibration curve using the equation [$Ca^{2+}$]=Kd*$\beta$((R-Rmin)/(Rmax-R)) where Rmax, Rmin, and R were, respectively, the maximum ratio, minimum ratio, and measured ratio at lower $\lambda$/upper$\lambda$. Rmax (14.5), Rmin (0.75), and $\beta$(8.51) were determined from free standing solution of 2 mM and zero [$Ca^{2+}$]$_o$ (+1 mM EGTA) in Hepes buffer solution as previously described {458, 457}. These values did not vay significantly from day to day. The data was displayed as ratio values of emission after excitation at the lower$\lambda$ and upper$\lambda$ (ie, 340/380 nM) due to the uncertainties in calculating cytosolic [$Ca^{2+}$] from a calibration curve determined in free standing solutions. The relative concentration of Fura-2 inside cells over the course of an experiment was monitored by measuring emission after excitation at the dye's isobestic point (360 nM).

2. Measurement of extracellular acidification (CYTOSENSOR)

The Cytosensor Microphysiometer (Molecular Devices Corp., Calif. USA) has been demonstrated to measure the activity of isolated cells in terms of their rate of production of hydrogen ions. This acidification rate is detected as a change in potential across a silicon light addressable sensor, during periods of media cessation (McConnell, et al., 1992).

CHO-NMB Cells seeded on polycarbonate microporous capsule cups were placed insensor chambers at 37° C. inside the microphysiometer, and maintained by a flow of nonbuffering Ham's F12 nutrient media (growth media without $NaHCO_3$, pH 7.3–7.4) at approximately 120 $\mu$L/min. The flow was halted for 22 seconds at the end of each 2 minute repeated cycle, and the rate of acidification ($\mu$ volts/sec) measured for 15 seconds during that period.

Agonists were introduced sequentially every 28 to 30 minutes to the perfusing media, 20 seconds before flow-off periods, and removed after two rate measurements via the automatic valve-switch.

The effects of various antagonists were determined after continuous perfusion 30 minutes prior to, and throughout the application of agonists. All agents were applied at the working pH of the media.

TABLE 1

Human NMB and GRP Receptor Binding Affinities

| Example No. | NMB $K_i$ (nM) | GRP $K_i$ (nM) |
|---|---|---|
| 11 | 103 | IA |
| 7 | 487 | IA |
| 24 | 413 | IA |
| 10 | 758 | 1460 |
| 19 | 3 | 762 |
| 22 | 35 | 589 |
| 20 | 33 | IA |
| 21 | 20 | 2550 |
| 23 | 16 | 5360 |

TABLE 1-continued

Human NMB and GRP Receptor Binding Affinities

| Example No. | NMB $K_i$ (nM) | GRP $K_i$ (nM) |
|---|---|---|
| 17 | 3310 | 2940 |
| 12 | 0.7 | 60 |
| 14 | 0.15 | 19 |
| 16 | 3 | 140 |
| 15 | 2 | 165 |
| 13 | 0.3 | 38 |
| 8 | 3 | 450 |
| 9 | 3.3 | 1130 |
| 18 | 25 | IA |
| 4 | 215 | IA |
| 5 | 942 | IA |
| 25 | 95 | IA |
| 2 | 14 | IA |
| 6 | 783 | IA |
| 1 | 5 | IA |
| 3 | 130 | IA |
| 26 | 0.25 | 29 |
| 27 | 0.15 | 1.0 |
| 28 | 0.81 | 79 |
| 29 | 10 | IA |
| 31 | 0.17 | 21 |
| 32 | 0.17 | 20 |

* IA is defined as those compounds which bind with lower than 10 micromolar affinity at the receptor.

TABLE 2

In Vitro Functional Activity of Compounds at NMB-Preferring Receptor (BB,1)

| Example No. | $[Ca^{2+}]_i$ Mobilization KE (nM) | Acidification Response appKB |
|---|---|---|
| 2 | — | 54.3 (2.5–152.4) |
| 1 | 18 (10–33) | 7.6 (5.3–110) |
| 14 | 1.2 | 1.0 |

General synthetic schemes for compounds of the invention follow.

DESCRIPTION OF SYNTHETIC SCHEMES

Scheme I describes the synthesis of C-terminal derivatives Examples 1 through 6. Intermediate I is prepared by the addition of 2,6-diisopropyl phenyl isocyanate to α-methyl Trp in DMF at 100° C. Coupling of Intermediate I to a selection of amines using HBTU and DIPEA in DMF furnished Examples 1 through 6.

Scheme II highlights the synthesis of Example 7. Addition of 2,6-diisopropyl phenyl isocyanate to (RS)-tryptophan in DMF at 100° C. provided Intermediate IV. This was then coupled to N-methyl cyclohexyl methyl amine using HBTU and DIPEA in DMF to give Example 7.

In Scheme III the intermediate acid V is prepared following the addition of p-nitrophenylisocyanate to (S)-α-methyl tryptophan in DMF at 60° C. Subsequent coupling of the intermediate acid V to cyclohexyl methyl amine and cyclohexan-1-ol methyl amine using HBTU and DIPEA in DMF yielded Examples 8 and 9, respectively.

Scheme IV outlines the preparation of Example 10. Initial addition of 2,6-diisopropyl phenyl isocyanate to (RS)-N-methyl tryptophan in DMF at 50 C. furnished the intermediate acid VI which was subsequently coupled to cyclohexyl methyl amine to provide Example 10.

In Scheme V the intermediate acid VII is prepared following the addition of $Boc_2O$ to (S)-α-methyl tryptophan in dioxan/water in the presence of $NaHCO_3$. Coupling of this intermediate to either cyclohexyl methyl amine or 1-(2-pyridyl) 1-aminomethyl cyclohexane (Intermediate II) in the presence of either HBTU, DIPEA, or DCC,PFP yielded the required Intermediate VIII. Deprotection of the Boc group using TFA in $CH_2Cl_2$ followed by coupling of the revealed amine to a selection of isocyanates in THF provided Examples 11 through 17.

Scheme VI describes the preparation of Example 18. Intermediate X is generated by adding $Boc_2O$ in dioxan/water in the presence of $NaHCO_3$ to (S)-α-methyl tryptophan. Coupling of the free carboxylic acid in Intermediate X to 2,6-diisopropyl phenyl amine using HBTU and DIPEA in DMF yielded Intermediate XI. Subsequent removal of the Boc protecting group using TFA in $CH_2Cl_2$ followed by reaction of the revealed amine with (RS)-α-t-butyl benzyl isocyanate in THF furnished Example 18.

In Scheme VII the intermediate acid XIII is prepared via the addition of 2,6-diisopropyl phenyl isocyanate to the required (RS)-α-methyl amino acid in DMF at 60° C. This intermediate is then coupled to 1-(2-pyridyl)-1-aminomethyl cyclohexane (Intermediate II) using HBTU and DIPEA in DMF to yield Examples 19 through 21. Catalytic hydrogenation of Example 19 furnished Example 22.

Scheme VIII outlines the preparation of Example 23. (RS)-N-trityl-histidine was reacted with 2,6-diisopropyl-phenylisocyanate in DMF at 60° C. to provide Intermediate XIV. This acid was then coupled to 1-(2-pyridyl)-1-aminomethyl cyclohexane (Intermediate II) using HBTU and DIPEA in DMF to give Intermediate XV which was subsequently reacted with formic acid in $CH_2Cl_2$ to provide Example 23.

The synthesis of Example 24 is outlined in Scheme IX. Reacting p-nitrophenyl chloroformate with (RS)-α-methyl tryptophan methyl ester provided the reactive Intermediate XVI which was then added to 2,6-diisopropylphenyl-N-methyl amine in toluene to yield Intermediate XVII. Hydrolysis of the methyl ester using LiOH in MeOH/water gave Intermediate XVIII which was then coupled with cyclohexyl methyl amine using HBTU and DIPEA in DMF to give Example 24.

In Scheme X Intermediate XIX is prepared by adding the acetonide of (S)-phenyl serinol to (RS)-N-Boc-α-methyl tryptophan using DCC and HOBt in $CH_2Cl_2$. Subsequent removal of the N-Boc protecting group using HCl gas in $Et_2O$ gave Intermediate XX which was then reacted with 2,6-diisopropyl phenyl isocyanate in EtOAc to give Example 25 after column chromatography.

Intermediate II was prepared after initial alkylation of pyridine-2-acetonitrile with 1,5-dibromopentane followed by reduction of the nitrile with Raney nickel.

Intermediate III was prepared by initial displacement of the alcohol in 2-phenyl cyclohexan-1-ol with azide via the use of DEAD, $PPh_3$, and $(PhO)_2PON_3$ in THF followed by catalytic reduction of the azide to give the amine Intermediate III.

SCHEME 1

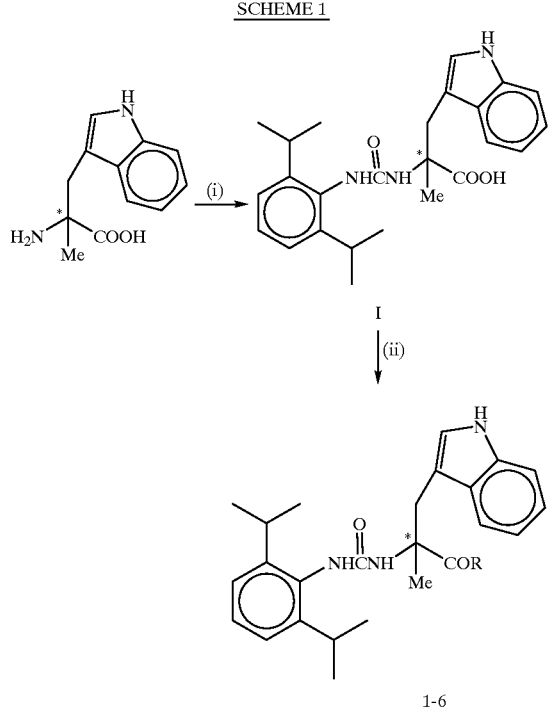

Reagents and Conditions:
i) 2,6-diisopropylphenylisocyanate, triethylamine, DMF, 100° C.;
ii) HBTU, R, DIPEA, DMF, 20° C.

Table for Scheme 1

| Example No. | * | R |
|---|---|---|
| 1 | S | II |
| 2 | R | HN—tetrahydronaphthyl (S) |
| 3 | R | HN—indanyl (S) |
| 4 | RS | HN—cyclohexylethyl |
| 5 | RS | NHPh |
| 6 | R | 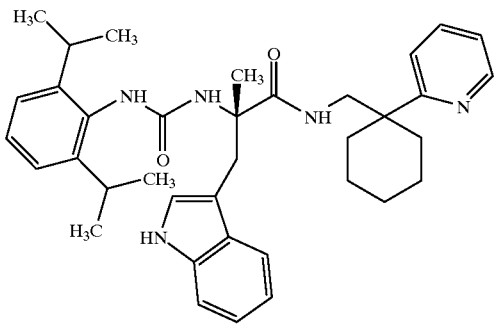 III |

Synthesis of Examples 1–6

Step 1

To a stirred solution of α-methyl-tryptophan (1.0 g, 4.6 mmol) in DMF (50 mL) was added 2,6-diisopropyl phenyl isocyanate (1.0 g, 5 mmol) followed by triethylamine (1.4 g, 14 mmol), and the mixture was heated to 100° C. for 1 hour. The reaction mixture was allowed to cool to room temperature and was taken up in EtOAc, washed with 1N HCl, brine, and dried (MgSO$_4$). The solvents were removed in vacuo, and the residue was triturated with ether to yield intermediate I as a white solid (1.38 g, 71%).

$^1$H NMR (DMSO): δ 1.15 (12H, br, 4×C$\underline{H}_3$($^i$Pr)), 1.46 (3H, s, αC$\underline{H}_3$), 3.26 (3H, br, 2×C$\underline{H}$($^i$Pr), C$\underline{H}$H indole), 3.41 (1H, d, 14.4 Hz, CH$\underline{H}$ indole), 6.32 (1H, br s, urea N$\underline{H}$), 6.96–7.39 (7H, br m, 3×C$\underline{H}$ (Ph), indole $\underline{H}$-2,$\underline{H}$-5,$\underline{H}$-6,$\underline{H}$-7), 7.56 (2H, br, indole $\underline{H}$-4, benzylic urea N$\underline{H}$), 10.96 (1H, br, indole N$\underline{H}$), 12.59 (1H, br, acid O$\underline{H}$);

IR (film): 3357, 2959, 1704, 1657, 1620, 1526, and 1456 cm$^{-1}$; MS m/e (CI) 422 (M$^+$+H) (4%) 204 (100%); Analysis C$_{25}$H$_{31}$N$_3$O$_3$·0.25H$_2$O,C,H,N; mp 194–195° C.

EXAMPLE 1

2-[3-(2,6-Diisopropyl-phenyl)-ureido]-3-(1H-indol-3-yl)-2-methyl-N-(1-pyridin-2-yl-cyclohexylmethyl)-propionamide To a stirred solution of the acid (I) (674 mg, 1.6 mmol) in DMF (80 mL) was added 2-(1H-benzotriazol-1-yl)-1,1,3,3,-tetramethyl uranium hexafluorophosphate (HBTU) (607 mg, 1.6 mmol) followed by diisopropyl ethyl amine (620 mg, 4.8 mmol), and the mixture was stirred at room temperature for 5 minutes. Amine II (304 mg, 1.6 mmol) was added to the solution which was stirred for a further 2 hours. The reaction mixture was taken up in EtOAc and washed with NaHCo$_3$ (aq), brine, dried (MgSO$_4$), and concentrated in vacuo. The residue was purified on reverse phase silica eluting with a gradient of MeOH/H$_2$O 50% to 100% to give Example 1 as a white solid (696 mg, 73%).

$^1$H NMR (CDCl$_3$): δ 0.75 and 0.88 (6H, 2×br d, (C$\underline{H}_3$)$_2$CH), 1.03 (6H, br d, (C$\underline{H}_3$)$_2$CH), 1.22–1.64 (8H, m, cyclohexyl), 1.64 (3H, s α C$\underline{H}_3$), 2.09–2.13 (2H, m, cyclohexyl), 2.97–3.04 (3H, m, (CH$_3$)$_2$ C$\underline{H}$×2, C$\underline{H}$H indole), 3.22 (1H, d, 14.65 Hz, CH$\underline{H}$ indole),

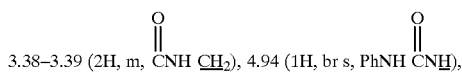

3.38–3.39 (2H, m, CNH C$\underline{H}_2$), 4.94 (1H, br s, PhNH CN$\underline{H}$), 5.44 (1H, br s, PhN$\underline{H}$), 6.34 (1H, brs, N$\underline{H}$ amide), 6.93–7.00 (2H, m, 2Ar$\underline{H}$), 7.03–7.11 (4H, m 4Ar$\underline{H}$), 7.22 (1H, d, 8.06 Hz, Ar$\underline{H}$), 7.26–7.31 (2H, m, 2Ar$\underline{H}$), 7.36 (1H, d, 8.06 Hz, Ar$\underline{H}$), 7.633 and 7.63 (1H, dt, 7.60 Hz, Ar$\underline{H}$), 7.73 (1H, br s, indole N$\underline{H}$), 8.54 (1H, d, 3.17 Hz, Ar$\underline{H}$);

IR (film 3291.0, 2955.0, 2870.0, 1652.0, 1532.0, 1457.0 and 742.0 cm$^{-1}$; MS m/e (APCI): 594.7 (M$^+$+H); Analysis C$_{37}$H$_{47}$N$_5$O$_2$, C, H, N; mp 116–117° C.; HPLC R.T.=12.88, C$^{18}$ reverse phase, 40% to 100% MeCN:TFA/H$_2$O:TFA.

EXAMPLE 2

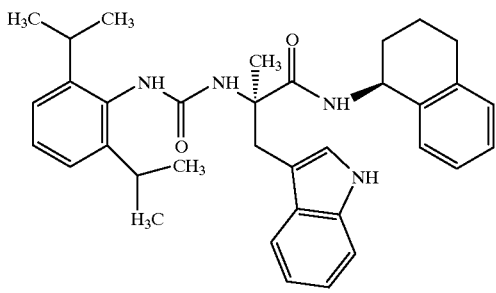

2-[3-(2,6-Diisopropyl-phenyl)-ureido]-3-(1H-indol-3-yl)-2-methyl-N-(1,2,3,4-tetrahydro-naphthalen-1-yl)-propionamide Example 2 was prepared as for Scheme 1 using 1,2,3,4-tetrahydro-1-napthyl amine(s).

Example 2 was isolated in 24% yield.

$^1$H NMR (CDCl$_3$); δ 0.43–0.52 (3H, br d, C$\underline{H}_3$CH), 0.90–0.94 (3H, br d, C$\underline{H}_3$CH), 0.98 and 1.07 (6H, 2×d, 6.59 and 6.11 Hz, (C$\underline{H}_3$)$_2$CH), 1.70 (3H, s, αC$\underline{H}_3$), 1.78–1.84 (3H, m, CHC$\underline{H}$HC$\underline{H}_2$tetralin), 1.87–2.04 (1H, m, CH$_2$C H$\underline{H}$tetralin), 2.69–2.91 (3H, m, (CH$_3$)$_2$C$\underline{H}$, PhC$\underline{H}_2$), 2.89 (1H, d, 14.65 Hz, CH$\underline{H}$ indole), 3.06–3.15 (1H, m, (CH$_3$)$_2$C $\underline{H}$), 3.47 (1H, d, 14.40 Hz, C$\underline{H}$H indole),

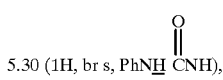

6.28 (1H, br s, N$\underline{H}$ amide), 6.63 (1H, br d, 7.57 Hz, Ar$\underline{H}$), 6.71 (1H, br d, 7.81 Hz, Ar$\underline{H}$), 6.91 (1H, t, 7.82 Hz, Ar$\underline{H}$), 6.98 (1H, t, 7.32 Hz, Ar$\underline{H}$), 7.04 (2H, t, 6.84 Hz, Ar$\underline{H}$), 7.09–7.16 (2H, m, 2Ar$\underline{H}$), 7.22–7.37 (3H, m, 3Ar$\underline{H}$), 7.39 (1H, d, 8.3 Hz, Ar$\underline{H}$), 7.77 (1H, br s, indole N$\underline{H}$);

IR (film): 3291.0, 2962.0, 1674.0, 1651.6, 1506.0, 14560.0, and 737.0 cm$^{-1}$; MS m/e (APCI) 551.5 (M+H$^+$);

Analysis C$_{35}$H$_{42}$N$_4$O$_2$, C, H, N; α$^D$=−45.33 (MeOH, c=0.075 g, 100 mL$^{-1}$); mp 210–212° C.; HPLC R.T.=17.90, C$^{18}$ reverse phase, 40% to 100% MeCN:TFA/H$_2$O:TFA.

EXAMPLE 3

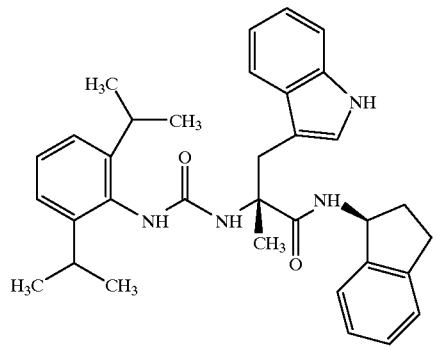

2-[3-(2,6-Diisopropyl-phenyl)-ureido]-N-indan-1-yl-3-(1H-indol-3-yl)-2-methyl-propionamide Example 3 was prepared as for Scheme 1 using S-(+)-1-aminoindone.

Example 3 was isolated in 40.5% yield.

$^1$H NMR (CDCl$_3$): δ 0.55 (3H, br s, C$\underline{H}_3$CH), 0.94 (3H, br d, 5.62 Hz, C$\underline{H}_3$CH), 0.99 (3H, br d, 6.35 Hz, C$\underline{H}_3$CH), 1.07 (3H, br d, 6.10 Hz, C$\underline{H}_3$CH), 1.70 (3H, s, αC$\underline{H}_3$),

2.78–2.97 (4H, m, C$\underline{H}$H indole, PhC$\underline{H}_2$, (CH$_3$)$_2$C$\underline{H}$), 3.01–3.20 (1H, Br m (CH$_3$)$_2$C$\underline{H}$), 3.47 (1H, d, 14.40 Hz, CH $\underline{H}$ indole),

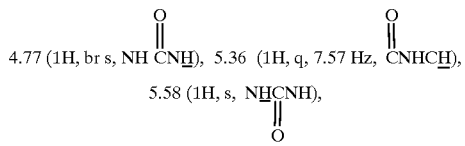

6.30 (1H, br s, amide n$\underline{H}$), 6.60 (1H, br d, 6.59 Hz, Ar$\underline{H}$), 6.65 (1H, br d, 8.06 Hz, Ar$\underline{H}$), 6.94–7.06 (3H, m, 3Ar$\underline{H}$), 7.11–7.20 (4H, m 4Ar$\underline{H}$), 7.26–7.34 (2H, m, 2Ar$\underline{H}$), 7.38 (1H, d, 7.32 Hz, Ar$\underline{H}$), 7.82 (1H, br s, indole NH);

IR (film): 3354.0, 1668.0, 1506.0 and 1060.0 cm$^{-1}$;

MS m/e (APCI) 537.7 (M+H$^+$); Analysis C$_{34}$H$_{40}$N$_4$O$_2$, C, H, N; α$^D$=−30.29° (MeOH, c=0.175 g, 100 mL$^{-1}$); mp 228–230° C.; HPLC R.T.=16.96, C$^{18}$ reverse phase, 40% to 100% MeCN:TFA/H$_2$O:TFA.

EXAMPLE 4

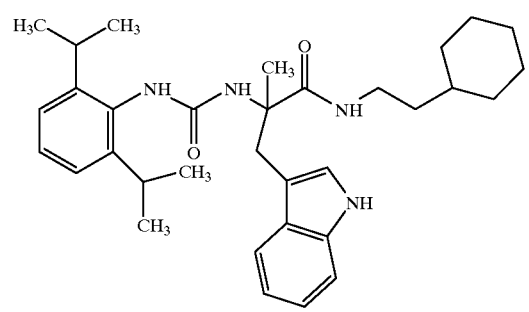

-continued

N-(2-Cyclohexyl-ethyl)-2-[3-(2,6-diisopropyl-phenyl)-ureido]-3-(1H-indol-3-yl)-2-methyl-propionamide Example 4 was prepared as for Scheme 1 using cyclohexyl ethyl amine.

Example 4 was isolated in 54% yield.

$^1$H NMR (DMSO-$d_6$): δ 0.50–1.73 (28H, br, α C$\underline{H}_3$+cyclohexyl+2×(C$\underline{H}_3$)$_2$CH+C$\underline{H}_2$ cyclohexyl), 2.92–3.30 (5H, br, CH$_2$N+2×(CH$_3$)$_2$C$\underline{H}$+C$\underline{H}$H indole), 3.50 (1H, br d, CH$\underline{H}$ indole, 6.42 (1H, br s, (PhNHCN$\underline{H}$), 6.83–7.38 7H, br m, 3 Ar$\underline{H}$+4 indole $\underline{H}$), 7.52 (1H, d, 8.0 z, indole $\underline{H}$), 7.71 2H, br, PhN$\underline{H}$C + amide N$\underline{H}$), 10.90 (1H, br, indole NH);

IR (film): 3289.0, 2924.0, 1668.0, 1652.0, 1520.0, 1456.0, and 740.0 cm$^{-1}$; MS m/e (CI) 531.8 (M$^+$+H): Analysis C$_{33}$H$_{46}$N$_4$O$_2$•0.2 H$_2$O, C, H, N;

mp 113°116° C.

EXAMPLE 5

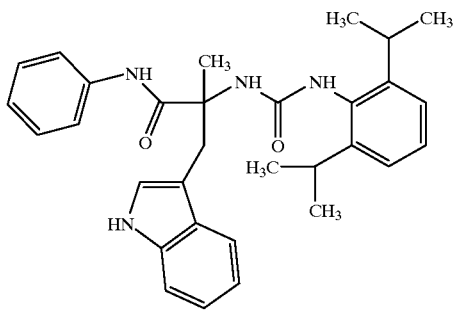

2-[3-(2,6-Diisopropyl-phenyl)-ureido]-3-(1H-indol-3-yl)-2-methyl-N-phenyl-propionamide Example 5 was prepared as for Scheme 1 using phenylamine.

Example 5 was isolated in 69% yield.

$^1$H NMR (DMSO-$d_6$): δ 1.11 (12H, br, 2× (C$\underline{H}_3$)$_2$CH), 1.47 (3H, br s, αC$\underline{H}_3$), 3.29 (2H, br, 2× (CH$_3$)$_2$C$\underline{H}$), 3.45 (2H, br, C$\underline{H}_2$ indole), 6.43 (1H, br s, PhNHCN$\underline{H}$), 6.90–7.39 (10H, br m, 6Ar$\underline{H}$+4 indole $\underline{H}$), 7.50–.71 (4H, br, 2Ar$\underline{H}$ + indole $\underline{H}$ + PhN$\underline{H}$CNH), 9.70 (1H, br s, amide N$\underline{H}$), 10.98 (1H, br, indole NH);

IR (film): 3278.0, 2927.0, 1673.0, 1599.0, 1519.0, 1499.0; MS m/e (CI) 497.6 (M$^+$+H); Analysis C$_{31}$H$_{36}$N$_4$O$_2$•0.5 H$_2$O, C, H, N; mp 121°124° C.

EXAMPLE 6

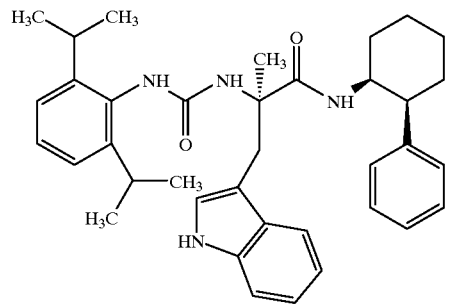

2-[3-(2,6-Diisopropyl-phenyl)-ureido]-3-(1H-indol-3-yl)-2-methyl-N-(2-phenyl-cyclohexyl)-propionamide Example 6 was prepared as for Scheme 1 using Intermediate III.

Yield (78 mg, 53%).

$^1$H NMR (CDCl$_3$): 0.85–2.04 (20H, m, 4× C$\underline{U}_2$), 1.36 (3H, s, α-C$\underline{U}_3$), 2.79 (1H, d, C$\underline{H}$H), 2.92–3.10 (3H, m, CH$\underline{H}$, 2×C$\underline{U}$(CU$_3$)$_2$), 4.46–4.51 (2H, m, NHC$\underline{H}$, PhC$\underline{U}$), 5.63 (1H, s, CON$\underline{H}$), 6.14 (1H, s, N$\underline{H}$CO), 6.91–7.28 (13H, m, aromatic), 7.70 (1H, s, N$\underline{H}$), 7.92 (1H, bs, CON$\underline{H}$);

IR (film); 3286, 3061, 2928, 2867, 1674, 1662, 1496, 906, and 734; MS m/e M$^+$580, 405, 377; HPLC 97.6%, R.T.= 16.55, 60% to 100% acetonitrile in water TFA);

$[α]\frac{22}{D} + 67.5°(c = 0.57, \text{acetone})$.

SCHEME 2

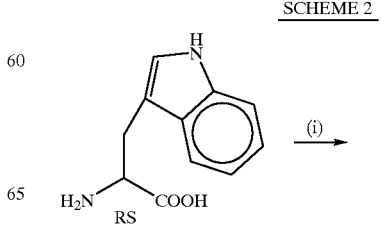

-continued

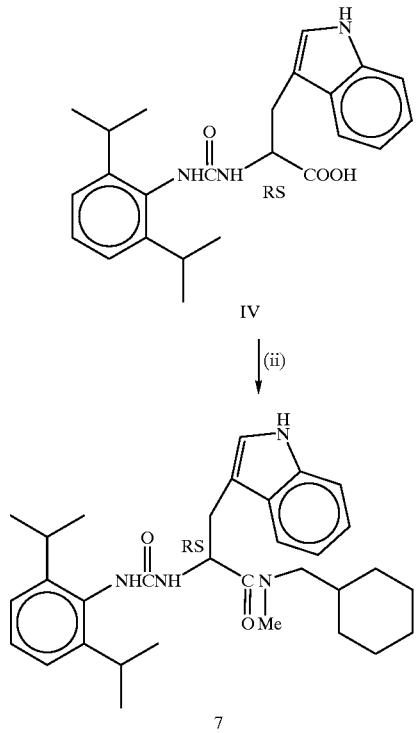

IV

Reagents and Conditions:
i) 2,6-Diisopropyl phenyl isocyanate, triethylamine, DMF, 100° C.
ii) HBTU, DIPEA, DMF, 20° C., N-methyl cyclohexyl methyl amine Synthesis of Example 7

Step 1

To a stirred solution of tryptophan (203 mg, 1.0 mmol) and triethylamine (9 mL, 65 mol) in dioxan (50 mL) was added diisopropyl phenyl isocyanate (203 mg, 1.0 mmol), and the mixture was refluxed for 3 hours. The reaction mixture was allowed to cool to room temperature and was taken up in EtOAc and washed with 1N HCl (aq), brine, and dried (MgSO$_4$). The solvents were removed in vacuo and the residue was triturated with ether to yield IV as a white solid (191 mg, 47%).

IR (film): 2962.0, 1614.0, and 1456.0 cm$^{-1}$; MS m/e (CI) 408 (M+H).

EXAMPLE 7

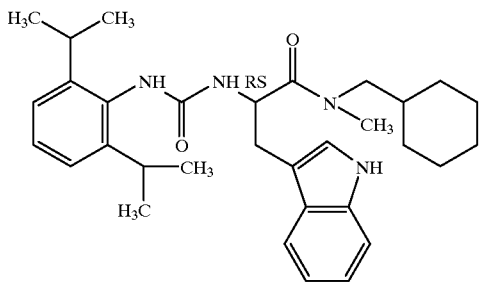

N-Cyclohexylmethyl-2-[3-(2,6-diisopropyl-phenyl)-ureido]-3-(1H-indol-3-yl)-N-methyl-propionamide Example 7 was isolated in 75% yield.

To a stirred solution of the acid IV (122 mg, 0.3 mmol), HBTU (114 mg, 0.3 mmol), and diisopropyl ethyl amine (116 mg, 0.9 mmol) in DMF (50 mL) which had been stirred for 5 minutes was added N-methyl cyclohexyl methyl amine (76.2 mg, 0.6 mmol). The mixture was stirred for 2 hours and then taken up in EtOAc (150 mL) and washed with NaHCO$_3$ (aq), 1N HCl (aq), brine, dried (MgSO$_4$), and concentrated in vacuo. The residue was purified on normal phase silica eluting with a gradient of heptane to 6:4 heptane: EtOAc to yield 7 (116.3 mg, 75%).

$^1$H NMR (CDCl$_3$): δ 0.51–1.07 (6H, m, cyclohexyl), 1.14 and 1.16 (12H, 2×d, 6.83 Hz, [(C$\underline{H}_3$)$_2$CH]×2), 1.23–1.60 (5H, m, cyclohexyl), 2.53–2.89 (2H, m, [(CH$_3$)$_2$C$\underline{H}$]×2), 2.57 and

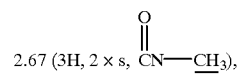

2.67 (3H, 2 × s, CN—CH$_3$), 3.01–3.26 (4H, m, C$\underline{HH}$ indole and N(Me)C$\underline{H}_2$),

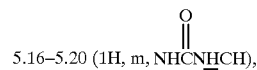

5.16–5.20 (1H, m, NHCN$\underline{H}$CH), 5.22–5.27 (1H, m, αH),

5.72 (1H, m, N$\underline{H}$CNH), 6.98–7.02 (1H, m, Ar$\underline{H}$), 7.08–7.19 (4H, m, 4Ar$\underline{H}$), 7.26–7.34 (2H, m, 2Ar$\underline{H}$), 7.69 (1H, d, 8.06 Hz, Ar$\underline{H}$), 7.95 (1H, br s, indole N$\underline{H}$);

IR (film: 3291.0, 2925.0, 1615.0, 1538.0, 1213.0, and 740.0 cm$^{-1}$; MS m/e (CI) 518 (M+H); Analysis C$_{32}$H$_{45}$N$_4$O$_2$, C, H, N; mp 179°–181° C.; HPLC R.T.=18.09, C$^{18}$ reverse phase, 10% to 80% MeCN:TFA/H$_2$O:TFA.

SCHEME 3

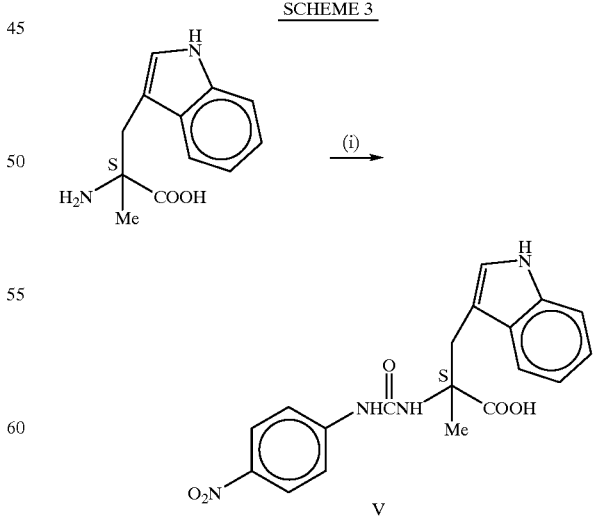

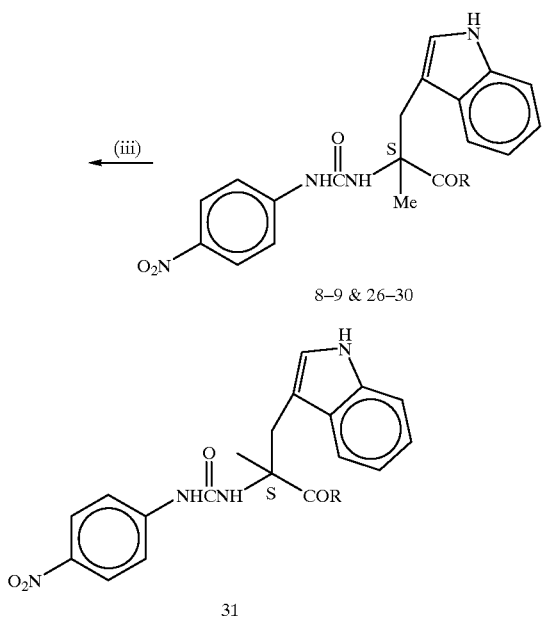

8–9 & 26–30

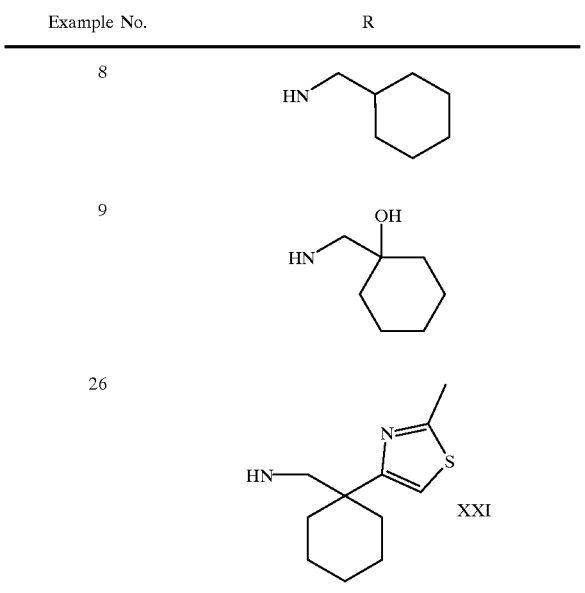

31

Reagents and Conditions:
i) p-nitrophenyl, isocyanate, pyridine, DMF, 60° C.
ii) HBTU, R, DIPEA, DMF, 20° C.
iii) 2N HCl, MeOH, Reflux

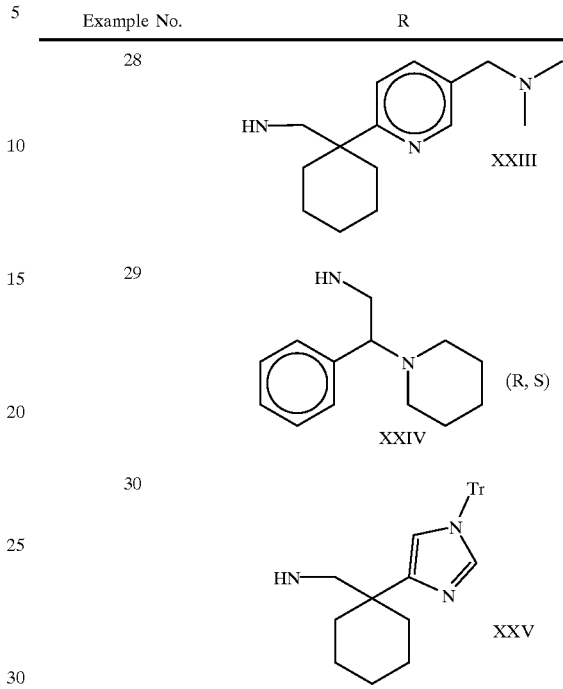

Synthesis of Examples 8 and 9, 26 through 30

Step 1

To a mixture of (S)-αMe tryptophan (2.51 g, 11.5 mmol) in DMF (100 mL) was added p-nitro phenyl isocyanate (1.89 g, 11.5 mmol) followed by pyridine (1 mL), and the reaction mixture was heated to 60° C. for 30 minutes. The solvent was removed in vacuo, and the residue was taken up in 1N NaHCO$_3$ (aq) and extracted with ether. The aqueous layer was acidified with 5N HCl (aq) to pH 1 and re-extracted with EtOAc, dried (MgSO$_4$), and concentrated in vacuo to give V as a yellow solid (4.07 g, 96.1%).

$^1$H NMR (DMSO): δ 1.55 (3H, s, αC$\underline{H}_3$), 3.31 (1H, d, obscured by water peak, CH$\underline{H}$ indole), 3.48 1H, d, 14.40 Hz, C$\underline{H}$H indole), 6.57 (1H, s, NH CN$\underline{H}$), 6.82 (1H, t, 7.81 Hz, indole H5), 6.99 (1H, t, 7.32 Hz, indole H6), 7.04 (1H, d, 2.2 Hz, indole H2), 7.30 (1H, d, 8.3 Hz, indole H7), 7.49 (1H, d, 8.06 Hz, indole H4), 7.62 (2H, d, 9.04 Hz, 2× p-NO$_2$Ph Ar$\underline{H}$), 8.16 (2H, d, 9.03 Hz, 2× P-NO$_2$ Ar$\underline{H}$,

9.45 (1H, s, NHCNH), 10.89 (1H, s, indole NH).

EXAMPLE 8

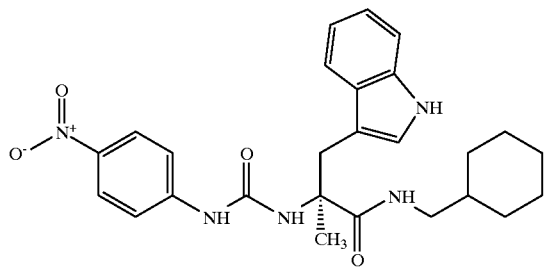

N-Cyclohexylmethyl-3-(1H-indol-3-yl)-2-methyl-2-[3-(4-nitro-phenyl)-ureido]-propionamide Example 8 was isolated in 54.4% yield.

To a solution of the acid V (150 mg, 0.4 mol), HBTU (155 mg, 0.4 mmol), and diisopropyl ethyl amine (158 mg, 1.2 mmol) in DMF (100 mL) which had been stirred for 5 minutes was added cyclohexyl methyl amine (250 mg, 2.17 mmol), and the reaction mixture was stirred for 2 hours. The mixture was taken up in EtOAc and washed with 1N HCl (aq), 1N NaHCO$_3$ (aq), brine, dried (MgSO$_4$), and concentrated in vacuo. The residue was purified on silica eluting with 1:1 heptane:EtOAc to EtOAc to give a yellow solid which was washed with EtOAc to yield pure 8 (104 mg, 54.4%).

$^1$H NMR (DMSO): δ 0.78–0.86 (2H, m, cyclohexyl), 1.06–1.20 (3H, m, cyclohexyl), 1.40–1.49 (1H, m, cyclohexyl), 1.57 (3H, s, αCH$_3$), 1.56–1.63 (5H, m, cyclohexyl),

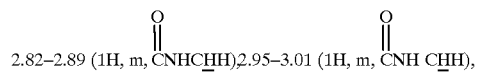

2.82–2.89 (1H, m, CNHCHH)2.95–3.01 (1H, m, CNH CHH), 3.34 (1H, d, 14.89 Hz, CHH indole), 3.58 (1H, d, 14.65 Hz, CHH indole),

6.66 (1H, s, PhNH CNH), 6.81 (1H, t, 7.57 Hz, indole H5), 6.94 (1H, s, indole H2), 6.98 (1H, t, 7.33 Hz, indole H6), 7.27 (1H, d, 8.06 Hz, indole H7), 7.48 (1H, d, 8.06 Hz, indole H4), 7.62 (2H, d, 9.3 Hz, 2-p-NO$_2$Ph ArH),

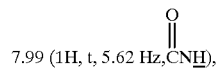

7.99 (1H, t, 5.62 Hz,CNH), 8.15 (2H, d, 9.03 Hz, 2× pNO$_2$Ph ArH,

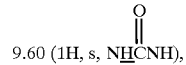

9.60 (1H, s, NHCNH), 10.81 (1H, s, indole NH);

IR (film): 3345.0, 2924.0, 2852.0, 1695.0, 1644.0, 1557.0, 1505.0, 1456.0, 1329.0, 1302.0, 1231.0, 1112.0, and 741.0 cm$^{-1}$; MS m/e (APCI) 478.6 (M+H$^+$);

Analysis C$_{26}$H$_{31}$N$_5$O$_4$•0.35 H$_2$O, C, H, N; mp 129–131 then 208°–225° C.; HPLC R.T.=13.52, C$^{18}$ reverse phase, 40% to 100% MeCN:TFA/H$_2$O:TFA.

EXAMPLE 9

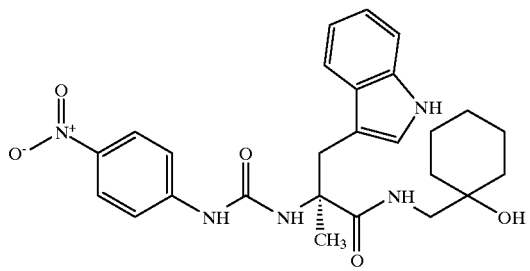

N-(1-Hydroxy-cyclohexylmethyl)-3-(1H-indol-3-yl)-2-methyl-2-[3-(4-nitro-phenyl)-ureido]-propionamide Example 9 was prepared as for Scheme 3 using 1-amino methyl-1-cyclohexanol.

Example 9 was isolated in 59% yield.

$^1$H NMR (DMSO): δ 1.13–1.57 (8H, m, cyclohexyl), 1.42 (3H, s, αCH$_3$), 2.07–2.12 (2H, m, cyclohexyl),

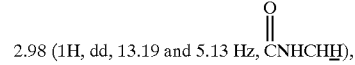

2.98 (1H, dd, 13.19 and 5.13 Hz, CNHCHH),

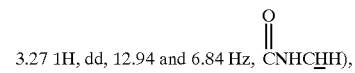

3.27 1H, dd, 12.94 and 6.84 Hz, CNHCHH), 3.41 and 3.37 (2H, 2× d, 14.90 Hz, CHH indole),

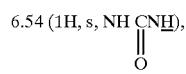

6.54 (1H, s, NH CNH), 6.81 (1H, t, 7.57 Hz, indole H5), 6.93 (1H, s, indole H2), 6.98 (1H, t, 7.57 Hz, indole H6), 7.10 (1H, t, 7.33 Hz, ArH),

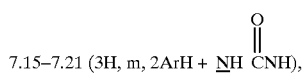
7.15–7.21 (3H, m, 2ArH + NH CNH), 7.27–7.30 (3H, m, 3ArH), 7.44 (1H, d, 8.06 Hz, indole H7), 7.66 (2H, d, 9.28 Hz, 2× pNO₂Ph ArH), 8.18 (2H, d, 9.28 Hz, 2pNO₂Ph ArH), 9.52 (1H, s, CNH), 10.81 (1H, s, indole NH).

IR (film): 3323.0, 1698.3, 1645.0, 1615.2, 1558.5, and 1505.0 cm⁻¹; MS m/e (APCI) 554.5 (M+H⁺); Analysis C₂₆H₃₁N₅O₅, C, H, N; mp 182°–184° C.; HPLC R.T.=10.53, C¹⁸ reverse phase, 40% to 100% MeCN:TFA/H₂O:TFA.

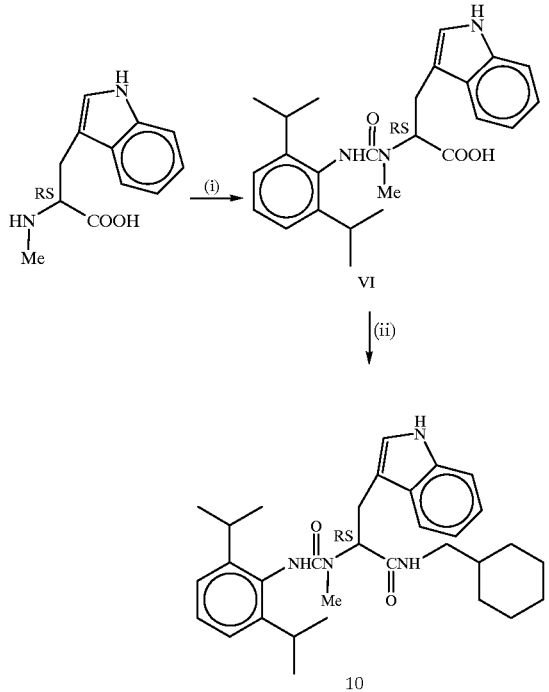

Reagents and Conditions:
i) 2,6-Diisopropylphenylisocyanate, triethylamine, DMF, 50° C.
ii) HBTU, cyclohexylmethylamine, DIPEA, DMF Synthesis of Example 10

Step 1

To a suspension of N-methyl (RS) tryptophan (500 mg, 2.3 mmol) in DMF (30 mL) was added 2,6-diisopropyl phenyl isocyanate (0.54 mL, 2.53 mmol), and triethyl amine (697 mg, 6.9 mmol), and the reaction mixture was heated to 50° C. and stirred for 30 minutes. The mixture was allowed to cool to room temperature before being taken up in EtOAc and washed with 1N HCl, brine, dried (MgSO₄), and concentrated in vacuo to give VI (966 mg, 100%).

¹H NMR (CDCl₃): δ 1.15 (6H, d, 6.84 Hz, (CH₃)₂CH), 1.25 (6H, d, 6.84 Hz, (CH₃)₂CH), 2.94 (3H, s, N-me), 2.88–3.05 (2H, 2×m, [(CH₃)₂CH]₂), 3.45–3.47 (2H, m, C HH indole), 4.97 (1H, t, 8.06 Hz, αH), 5.81 (1H, s, NHC), 7.10–7.20 (5H, m, 5ArH), 7.22 (1H, t, 7.1 Hz, ArH), 7.26–7.30 (1H, m, ArH), 7.38 (1H, d, 8.06 Hz, ArH), 7.66 (1H, d, J=7.82 Hz, ArH), 8.17 (1H, s, indole NH);
IR (film: 3320.8, 2963.0, 2291.5, 1716.0, 1652.0, 1507.0, 1466.8, and 743.0 cm⁻¹;
MS m/e (ES) 420.7 (M–H⁺) 421.7 (M⁺).

EXAMPLE 10

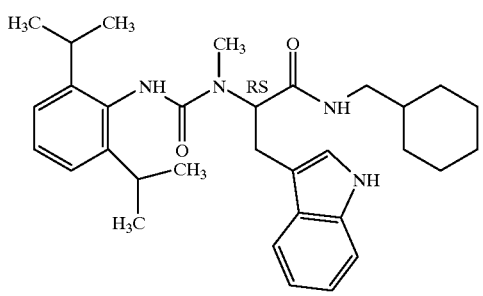

N-Cyclohexylmethyl-2-[3-(2,6-diisopropyl-phenyl)-1-methyl-ureido]-3-(1H-indol-3-yl)-propionamide Example 10 was isolated in 32.6% yield.

To a solution of the acid VI (211 mg, 0.5 mmol) in DMF (50 mL) was added HBTU (189.6 mg, 0.5 mmol), diisopropyl ethyl amine (194 mg, 1.5 mmol), and the mixture was stirred for 10 minutes. Cyclohexyl methyl amine (80 mg, 0.7 mmol) was then added to the reaction mixture and this was stirred for a further 5 hours. The mixture was taken up in EtOAc and washed with 1N HCl (aq), NaHCO₃ (aq), brine, dried (MgSO), and concentrated in vacuo. The residue was purified on normal phase silica eluting with a gradient of heptane to 6:4 heptane:EtOAc to give a solid which was washed with ether to yield pure 10 (84.2 mg, 32.6%).

¹H NMR (CDCl₃): δ 0.82–0.91 (2H, m, cyclohexyl), 1.10–1.20 (8H, m, cyclohexyl), 1.14 (12H, d, 6.84 Hz, [(CH₃)₂CH]×2), 1.38–1.43(1H, m, CNHCH₂CH), 1.58–1.70 (2H, m, [(CH₃)₂CH]×2), 3.03 (3H, s, N—CH₃), 3.08(2H, t, 6.35 Hz, CNHCH₂), 3.30 (1H, dd, 9.77 and 15.87 Hz, CHH indole), 3.36 (1H, dd, 6.10 and 15.87 Hz, CHH indole), 5.29–5.33 (1H, m, αH), 5.65(1H, s, Ph N<u>H</u>C),
  ‖
  O 6.50 (1H, bt, amide N<u>H</u>), 7.08 (1H, d, 2.2 Hz, indole H2), 7.10–7.20 (3H, m, 3Ar<u>H</u>), 7.20 (1H, t, 7.10 Hz, Ar<u>H</u>), 7.22–7.26 (1H, m, Ar<u>H</u>), 7.37 (1H, d, 8.3 Hz, Ar<u>H</u>), 7.67 (1H, d, 7.57 Hz, 1Ar<u>H</u>), 7.97 (1H, s, indole N<u>H</u>);

IR (film): 3323.0, 2925.0, 1668.2, 1645.0, and 1506.0 cm$^{-1}$; MS m/e (APCI) 515.9 (M$^+$), 517.7 (M+H$^+$); Analysis $C_{32}H_{44}N_4O_2$, C, H, N; mp 183–185.5° C.; HPLC R.T.= 18.41, $C^{18}$ reverse phase, 40% to 100% MeCN:TFA/$H_2O$:TFA.

SCHEME 5

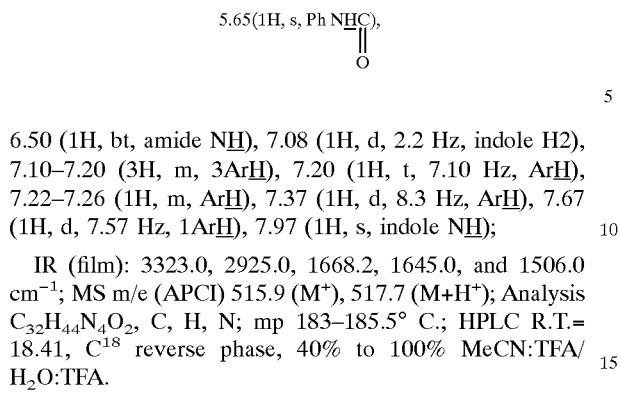

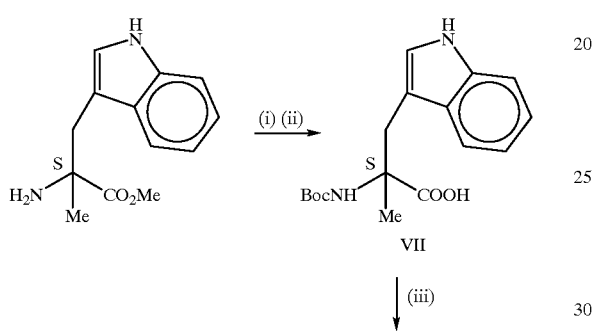

Reagents and Conditions:
i) Boc$_2$O, NaHCO$_3$, dioxan
ii) LiOH, THF, MeOH
iii) HBTU, R, DIPEA, DMF or DCC, PFP, R, EtOAc
iv) TFA, DCM
v) R'NCO, THF Table for Scheme 5

| Example No. | R | R' |
|---|---|---|
| 11 | 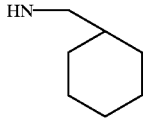 | 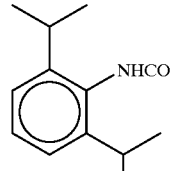 |
| 12 | 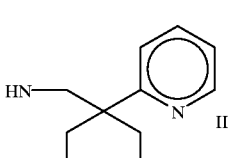 | 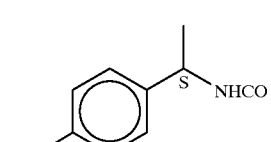 |
| 13 | 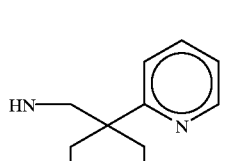 |  |

Table for Scheme 5

| Example No. | R | R' |
|---|---|---|
| 14 | HN-CH2-C(cyclohexyl)(2-pyridyl) | 4-NO2-C6H3-NHCO- (O2N, NHCO) |
| 15 | HN-CH2-C(cyclohexyl)(2-pyridyl) | 4-CF3-C6H3-NHCO- (F3C, NHCO) |
| 32 | HN-CH2-C(cyclohexyl)(5-OMe-2-pyridyl) (XXII) | 4-CN-C6H3-NHCO- (NC, NHCO) |
| 16 | HN-CH2-C(cyclohexyl)(2-pyridyl) | 4-EtO2C-C6H3-NHCO- (EtO2C, NHCO) |
| 17 (R,S-stereochemistry) | HN-CH2-cyclohexyl | 2,6-(OMe)2-C6H3-NHCO- |

Synthesis of Examples 12–16

Step 1 as for Examples 11 and 17.

Step 2

To a solution of the acid VII (2.067 g, 6.5 mmol), HBTU (2.47 g, 6.5 mmol), and diisopropyl ethyl amine (2.52 g, 19.5 mmol) in DMF (130 mL) which had been stirred~5 minutes was added the amine II (1.24 g, 6.5 mmol), and stirring was continued for a further 2 hours. The reaction mixture was taken up in EtOAc and washed with NaHCO$_3$ (aq), 1N HCl (aq), dried (MgSO$_4$), and concentrated in vacuo. The residue was purified on reverse phase silica eluting with 77% MeOH/H$_2$O to obtain pure VIII (R=II) (2.17 g, 68%).

$^1$H NMR (CDCl$_3$): δ 1.27–1.63 (8H, m, cyclohexyl), 1.40 (9H, s, (C$\underline{H}_3$)$_3$C), 1.52 (3H, s, αC$\underline{H}_3$), 2.0–2.13 (2H, m, cyclohexyl), 3.31 (1H, d, 14.65 Hz, CH$\underline{H}$ indole), 3.29–3.50 (3H, m, CH$\underline{H}$ indole and $\overset{O}{\underset{\|}{C}}$NHC$\underline{H}_2$), 5.05–5.15 (1H, br s, $\overset{O}{\underset{\|}{C}}$N$\underline{H}$), 6.93 (1H, s, indole H2), 7.0–7.12 (2H, m, 2ArH), 7.16 (1H, t, 8.06 Hz, ArH), 7.10–7.22 (1H, m, N$\underline{H}\overset{O}{\underset{\|}{C}}$), 7.31 (2H, t, 7.81 Hz, 2ArH), 7.52 (1H, d, 7.57 Hz, ArH), 7.63 (1H, t, 7.81 Hz, ArH), 7.99 (1H, br s, indole NH), 8.50 (1H, d, 3.66 Hz, pyridyl H);

IR (film): 3333.0, 2928.0, 1652.0, 1471.0, and 1163.0 cm$^{-1}$; MS m/e (APCI) 491.6 (M+H$^+$); Analysis $C_{29}H_{38}N_4O_3$, C, H, N; mp: 78.5–79.5° C.; HPLC R.T.=8.47 and 8.73, $C^{18}$ reverse phase, 40% to 100% MeCN:TFA/$H_2O$:TFA.

Step 3

VIII (R=II) (473 mg, 0.96 mmol) was dissolved in formic acid (30 mL) and stirred for 5 hours. The mixture was basified with dilute sodium hydroxide solution to pH 14 and extracted with EtOAc, dried (MgSO$_4$), and concentrated in vacuo to give IX (R=II) (300 mg, 80%).

$^1$H NMR (CDCl$_3$): δ 1.27–1.63 (8H, m, cyclohexyl), 1.32 (3H, s, αC$\underline{H}_3$), 2.0–2.22 (2H, 2×m, cyclohexyl), 2.79 (1H, d, 14.65 Hz, indole CH$\underline{H}$), 3.35 (1H, d, 14.65 Hz, indole C$\underline{H}$H), 3.36 (1H, dd, 6.35 Hz, 13.18 Hz, CNHC$\underline{H}$H), 3.42 (1H, dd, 6.10 and 13.18 Hz, CH$\underline{H}$NHC), 7.00 (1H, d, 2.44 Hz, indole H2), 7.03–7.19 (4H, m, 4Ar$\underline{H}$), 7.35 (1H, d, 8.06 Hz, Ar$\underline{H}$), 7.52 (1H, td, 1.95 and 7.57 Hz, Ar$\underline{H}$), 7.59 (1H, d, 7.82 Hz, Ar$\underline{H}$), 7.60–7.68 (1H, br t, CN$\underline{H}$), 8.02 (1H, br s, indole N$\underline{H}$), 8.51–8.58 (1H, m, pyridyl $\underline{H}$); MS m/e (ES) 391.7 (M+H$^+$).

EXAMPLE 12

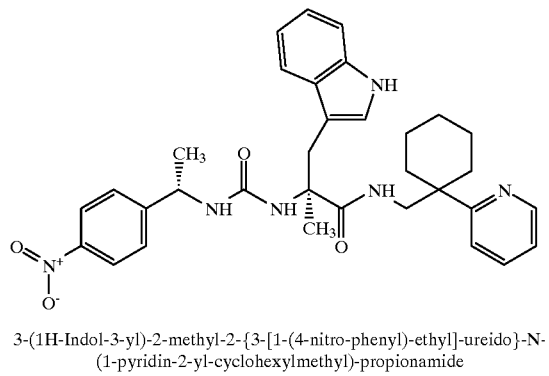

3-(1H-Indol-3-yl)-2-methyl-2-{3-[1-(4-nitro-phenyl)-ethyl]-ureido}-N-(1-pyridin-2-yl-cyclohexylmethyl)-propionamide Example 12 was isolated in 39% yield.

To a solution of the amine IX (R=II) (100 mg, 0.26 mmol) in THF (100 mL) was added 4-nitrol-α-methyl benzyl isocyanate (180 mg, 0.94 mmol), and the solution was stirred for 4 hours at room temperature. The reaction mixture was taken up in EtOAc and washed (H$_2$O), dried (MgSO$_4$), and concentrated in vacuo. The residue was taken up in EtOAc and crystallized to yield 12 (58.6 mg, 39%).

$^1$NMR (DMSO): δ 1.08–1.48 (8H, m, cyclohexyl), 1.24 (3H, s, αC$\underline{H}_3$), 1.33 (3H, d, 7.08 Hz, PNO$_2$PhCHC$\underline{H}_3$), 2.03–2.18 (2H, m, cyclohexyl), 3.07(1H, dd, 5.62 and 12.94 Hz, C$\underset{\overset{\|}{O}}{N}$HCH$\underline{H}$), 3.21–3.15(2H, m, CH$\underline{H}$ indole and C$\underset{\overset{\|}{O}}{N}$HC$\underline{H}$H), 3.34–3.29 (1H, d, obscured by water peak CH$\underline{H}$ indole), 4.90 (1H, m, C$\underline{H}$CH$_3$), 5.93(1H, s, CHN$\underline{H}$C$\underset{\overset{\|}{O}}{N}$H), 6.77 (1H, d, 7.32 Hz, Ar$\underline{H}$), 6.86–6.90(2H, m, 1Ar$\underline{H}$, and C$\underset{\overset{\|}{O}}{N}$$\underline{H}$), 7.01 (1H, t, 7.32 Hz, Ar$\underline{H}$), 7.13–7.16 (1H, m, Ar$\underline{H}$), 7.27–7.30 (2H, m, 2Ar$\underline{H}$), 7.36–7.40(2H, m, C$\underset{\overset{\|}{O}}{N}$$\underline{H}$ and Ar$\underline{H}$), 7.55 (2H, d, 8.79 Hz, 2×p—NO$_2$Ph Ar$\underline{H}$), 7.64 (1H, td, 1.95 and 7.81 Hz, Ar$\underline{H}$), 8.16 (2H, d, 8.54 Hz, 2×p—NO$_2$Ph Ar $\underline{H}$), 8.50 (1H, d, 2.93 Hz, pyridyl $\underline{H}$), 10.85 (1H, s, indole N $\underline{H}$);

IR (film): 3340.0, 2923.6, 1642.0, 1520.0, 1345.6, and 1107.0 cm$^{-1}$; MS m/e (APCI) 583.6 (M+H$^+$); Analysis $C_{33}H_{38}N_6O_4$, C, H, N; mp 202–203.5° C.; HPLC R.T.=9.38 and 9.77, $C^{18}$ reverse phase, 40% to 100% MeCN:TFA/$H_2O$:TFA;

EXAMPLE 13

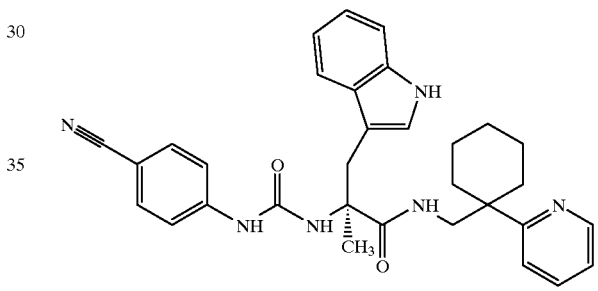

2-[3-(4-Cyano-phenyl)-ureido]-3-(1H-indol-3-yl)-2-methyl-N-(1-pyridin-2-yl-cyclohexylmethyl)-propionamide Example 13 was prepared as for Scheme 5 using Intermediate II and 4-cyano phenyl isocyanate.

Example 13 was isolated in 37% yield.

$^1$H NMR (DMSO): δ 1.13–1.55 (8H, m, cyclohexyl), 1.41 (3H, s, αC$\underline{H}_3$), 2.16–2.23 (2H, m, cyclohexyl), 3.09(1H, dd, 5.37 and 12.94 Hz, C$\underset{\overset{\|}{O}}{N}$HCH$\underline{H}$), 3.28–3.39(3H, m obscured by water peak, C$\underset{\overset{\|}{O}}{N}$HCH$\underline{H}$ and indole CH$\underline{H}$), 6.44(1H, s, NH C$\underset{\overset{\|}{O}}{N}$$\underline{H}$), 6.81 (1H, t, 7.32 Hz, indole H5), 6.92 (1H, d, 2.20 Hz, indole H2), 6.98 (1H, t, 7.08 Hz, indole H6), 7.07–7.10 (1H, m, Ar $\underline{H}$), 7.28 (2H, t, 8.06 Hz, 2Ar$\underline{H}$), 7.41 (1H, d, 8.06 Hz, indole H7), 7.44–7.52(3H, m, 2ArH and CNH), 7.56 (2H, d, 8.79 Hz, 2×pNO₂Ph ArH), 7.68 (2H, d, 8.79 Hz, 2×pNO₂Ph ArH), 8.47–8.49(1H, m, pyridyl H), 9.22 1H, s, CNH), 10.81 (1H, s, indole NH);
IR (film): 3352.0, 2934.2, 1652.0, 1532.0, and 1113.0 cm⁻¹; MS m/e (APCI): 535.5 (M+H⁺); Analysis C₃₂H₃₄N₆O₂, C, H, N; mp 234.5–237° C.; HPLC R.T.=6.75 and 7.02, C¹⁸ reverse phase, 40% to 100% MeCN:TFA/H₂O:TFA;

EXAMPLE 14

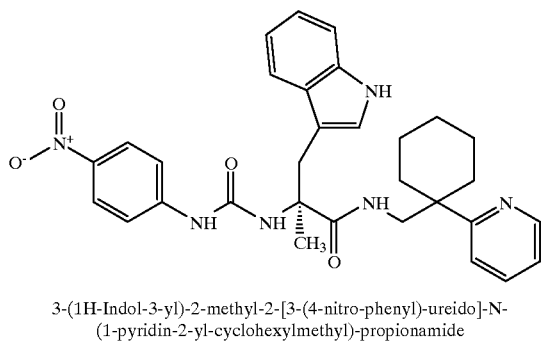

3-(1H-Indol-3-yl)-2-methyl-2-[3-(4-nitro-phenyl)-ureido]-N-(1-pyridin-2-yl-cyclohexylmethyl)-propionamide Example 14 was isolated in 63.3% yield.

Example 14 was prepared as for Scheme 5 using Intermediate II and 4-nitrophenyl isocyanate.

¹H NMR (DMSO): δ 1.11–1.55 (8H, m, cyclohexyl), 1.44 (3H, s, αCH₃), 2.18–2.25 (2H, m, cyclohexyl), 3.09(1H, dd, 5.37 and 13.18 Hz, CNH CHH), 3.29–3.38(3H, m, CHH indol and CNHCHH), 6.54(1H, s, NHCNH), 6.81 (1H, t, 8.06 Hz, indole H5), 6.93 (1H, s, indole H2), 6.98 (1H, t, 7.08 Hz, indole H6), 7.07–7.10 (1H, m, ArH), 7.28 (2H, t, 9.03 Hz, 2ArH), 7.42 (1H, d, 7.81 Hz, indole H7), 7.49–7.60 (2H, m, amide NH and 1ArH), 7.62 (2H, d, 9.28 Hz, 2×p—NO₂Ph ArH), 8.16 (2H, d, 9.28 Hz, 2×p—NO₂Ph ArH), 8.48-8.50 (1H,m,pyridyl H), 9.49 1H,s,PhN HCNH), 10.81 (1H, s, indole NH);
IR (film): 3363.0, 2934.2, 1644.2, 1454.1, 1433.0, and 1046.0 cm⁻¹; MS m/e (APCI): 555.5 (M+H⁺); Analysis C₃₁H₃₄N₆O₄, C, H, N; mp 215–219° C.; HPLC R.T.=8.79, C¹⁸ reverse phase, 40% to 100% MeCN:TFA/H₂O:TFA.

EXAMPLE 15

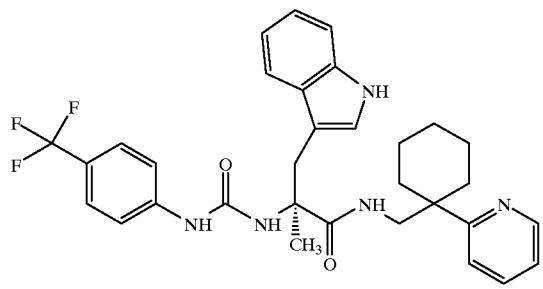

3-(1H-Indol-3-yl)-2-methyl-N-(1-pyridin-2-yl-cyclohexylmethyl)-2-[3-(4-trifluoromethyl-phenyl)-ureido]-propionamide Example 15 was isolated in 20% yield.

Example 15 was prepared as for Scheme 5 using Intermediate II and 4-trifluoromethylphenylisocyanate.

¹H NMR (DMSO): δ 1.12–1.55 (8H, m, cyclohexyl), 1.40 (3H, s, αCH₃), 2.18–2.26 (2H, m, cyclohexyl), 3.08(1H, dd, 5.37 and 12.94 Hz, CNHCHH), 3.27–3.36(3H, obscured by water peak, CHH indole and CNHCHH), 6.38(1H, s, NH CNH), 6.81 (1H, t, 7.81 Hz, indole H5), 6.93 (1H, d, 2.2 Hz, indole H2), 6.98 (1H, t, 7.57 Hz, indole H6), 7.07–7.10 (1H, m, Ar H), 7.29 (2H, t, 9.03 Hz, 2ArH), 7.42 (1H, d, 8.06 Hz, indole H7), 7.46–7.51(2H, m, ArH and NHC), 7.59 (4H, s, 4×ArH), 8.48 8.49 (1H, m, pyridyl H), 9.13(1H, s, NHC), 10.83 (1H, br s, indole NH);

IR (film): 3360.0, 2934.2, 1651.9, 1559.3, 1440.3, 1334.6, and 1070.0 cm⁻¹; MS m/e (APCI): 578.5 (M+H⁺); Analysis C₃₂H₃₄N₅O₂F₃, C, H, N; HPLC R.T.=10.99, C¹⁸ reverse phase, 40% to 100% MeCN:TFA/H₂O:TFA.

EXAMPLE 16

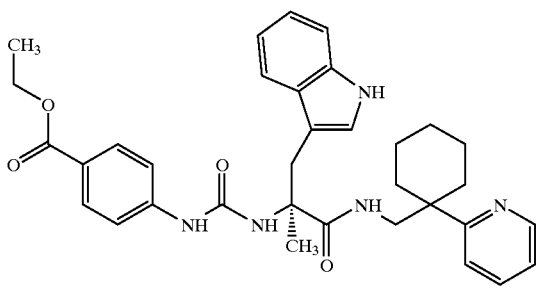

4-(3-{2-1H-Indol-3-yl)-1-methyl-1-[(1-pyridin-2-yl-cyclohexylmethyl)-carbamoyl]-ethyl}-ureido)-benzoic acid ethyl ester Example 16 was prepared as for Scheme 5 using Intermediate II and ethyl-4-isocyanatobenzoate.

Example 16 was isolated in 55% yield.

$^1$H NMR (CDCl$_3$): δ 1.26–1.61 (8H, m, cyclohexyl), 1.39 (3H, t, 7.08 Hz, C$\underline{H}_3$CH$_2$O), 1.70 (3H, s, αC$\underline{H}_3$), 2.03–2.1(2H, m, cyclohexyl),

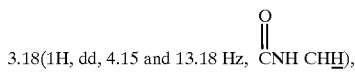

3.18(1H, dd, 4.15 and 13.18 Hz, CNH CH$\underline{H}$), 3.30 (1H, d, 14.65 Hz, indole),

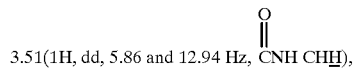

3.51(1H, dd, 5.86 and 12.94 Hz, CNH CH$\underline{H}$), 3.53 (1H, d, 14.65 Hz, CH$\underline{H}$ indole CH$\underline{H}$), 4.35 (1H, q', 7.08 Hz, CH$_3$C$\underline{H}_2$O),

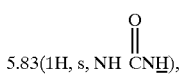

5.83(1H, s, NH CN$\underline{H}$), 6.85 (1H, d, 2.44 Hz, Ar$\underline{H}$), 6.98 (1H, t, 7.81 Hz, Ar$\underline{H}$),

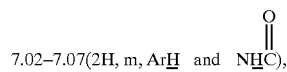

7.02–7.07(2H, m, Ar$\underline{H}$ and N$\underline{H}$C), 7.11 (1H, t, 7.08 Hz, Ar$\underline{H}$), 7.24–7.33 (4H, m, 4Ar$\underline{H}$),

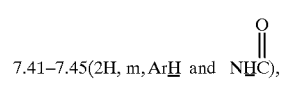

7.41–7.45(2H, m, Ar$\underline{H}$ and N$\underline{H}$C), 7.59 (1H, td, 7.57 and 1.95 Hz, Ar$\underline{H}$), 7.90 (2H, d, 8.79 Hz, 2Ar$\underline{H}$), 7.95 (1H, br s, indole NH), 8.44–8.45 (1H, m, pyridyl $\underline{H}$).

IR (film): 3342.0, 2931.0, 1645.0, 1538.0, 1279.0, 1174.0, and 1107.0 cm$^{-1}$; MS m/e (APCI) 582.5 (M+H$^+$); Analysis C$_{34}$H$_{39}$N$_5$O$_4$, C, H, N; mp 117–120° C.; HPLC R.T.=9.58, C$^{18}$ reverse phase, 40% to 100% MeCN:TFA/H$_2$O:TFA.

Synthesis of Examples 11 and 17

Step 1

To a stirring solution of (S)-α-methyl tryptophan methyl ester (5.0 g, 22 mmol) in dioxan (50 mL) water (50 mL) was added NaHCO$_3$ (3.0 g, 36 mmol) followed by di-t-butyl dicarbonate (5.0 g, 23 mmol). Stirring was continued for 18 hours at ambient temperature. The mixture was acidified (HCl, 200 mL, 2N aq, cautiously at first) and the products extracted (EtOAc, 300 mL). The organic phase was dried (MgSO$_4$) and evaporated to dryness in vacuo (60° C.). The residual brown oil was purified by flash column chromatography (silica gel, eluant 40% EtOAc/60% heptane). Recovered 7.0 g (99%) of the protected ester as a pale yellow oil, which was not fully characterized. To a stirring solution of this ester (7.0 g, 21 mmol) in MeOH (60 mL)/THF (60 mL) was added a solution of LiOH.H$_2$O (1.5 g, 35 mmol) in water (20 mL). Stirring was continued for 18 hours at ambient temperature. The mixture was acidified (HCl, 200 mL, 2N aq) and the products extracted (EtOAc, 2×150 mL). The combined organics were dried (MgSO$_4$) and evaporated to dryness in vacuo (60° C.). Recovered (VII) 6.8 g (99%) as a pale yellow oil. This was not fully characterized.

IR (film): 1702 and 1694 cm$^{-1}$.

Step 2

To a stirring solution of (VII) (0.5 g, 1.6 mmol) in EtOAc (30 mL) was added N,N-dicyclohexyl carbodiimide (0.5 g, 2.4 mmol) and pentafluorophenol (0.4 g, 2.2 mmol). Stirring was continued for 30 minutes at ambient temperature, then the white precipitate was removed by filtration. To the filtrate was added, with stirring, aminomethyl cyclohexane (0.4 mL, 0.3 g, 3.0 mmol). Stirring was continued for 30 minutes at ambient temperature, then the reaction mixture was washed with HCl (50 mL, 2N aq), dried (MgSO$_4$), and evaporated to dryness in vacuo (60° C.). The residue was purified by flash column chromatography (silica gel, eluant 80% EtOAc/heptane) followed by reverse phase column chromatography (74% MeOH/26% H$_2$O). This gave (VIII) (R=CH$_2$ cyclohexyl) as a white foam (0.54 g, 83%).

$^1$H NMR (DMSO-d$_6$): δ 0.83 (2H, br, cyclohexyl), 1.08–1.72 (21H, m, α-C$\underline{H}_3$+(C$\underline{H}_3$)$_3$O+cyclohexyl), 2.78–3.02 (2H, br, C$\underline{H}_2$ N), 3.18 (1H, br, CH$\underline{H}$ indole), 3.31 (obscured, C$\underline{H}$H indole),

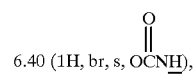

6.40 (1H, br, s, OCN$\underline{H}$), 6.92 (1H, t, 7.6 Hz, indole $\underline{H}$), 6.96 (1H, s, indole $\underline{H}$), 7.03 (1H, t, 7.6 Hz, indole $\underline{H}$), 7.31 (1H, d, 8.0 Hz, indole $\underline{H}$), 7.48 (1H, d, 7.6 Hz, indole H), 7.61 (1H, br, amide N$\underline{H}$), 10.85 (1H, br, indole N$\underline{H}$);

IR (film): 3322, 2922, 1698, 1652, 1519, 1490, and 1455 cm$^{-1}$; MS m/e (CI) 414 (M$^+$+H);,mp 82–85° C.; Analysis C$_{24}$H$_{35}$N$_3$O$_3$.0.1 H$_2$O, C, H, N;

$$\alpha\frac{20}{D} = -29°(c = 0.5, \text{MeOH}).$$

Step 3

To a solution of (VIII) (0.14 g, 0.34 mmol) in CH$_2$Cl$_2$ (30 mL) was added trifluoroacetic acid (0.1 mL, 1.3 mmol), and the reaction was warmed to reflux for 30 minutes, then allowed to cool to ambient temperature. The mixture was taken up in EtOAc (100 mL) and washed (Na$_2$CO$_3$, 2N aq, 100 mL), dried (MgSO$_4$), and evaporated to dryness in vacuo (60° C.). Recovered (IX) as a yellow oil (109 mg, 103%). This was to fully characterized.

EXAMPLE 11

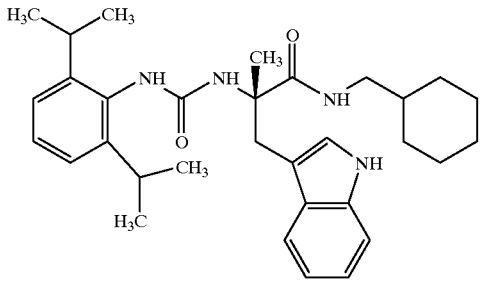

N-Cyclohexylmethyl-2-[3-(2,6-diisopropyl-phenyl)-ureido]-3-(1H-indol-3-yl)-2-methyl-propionamide Example 11 was isolated in 74% yield.

To a stirring solution of (IX) (109 mg, 0.34 mmol) in THF (40 mL) was added, 2,6-diisopropyl phenyl isocyanate (0.15 g, 0.7 mmol), and the reaction was heated to reflux for 30 minutes, then allowed to cool to ambient temperature. Volatiles were removed in vacuo (60° C.), and the residue was purified by flash column chromatography (silica gel, eluant 50% EtOAc/50% heptane) followed by reverse phase column chromatography (63% acetonitrile/37% water). Recovered Example 11 as a white solid (132 mg, 74%), mp 229–231° C.

$^1$H NMR (DMSO-d$_6$): δ 0.50–1.70 (26H, br m, αCH$_3$+2×(CH$_3$)$_2$CH+cyclohexyl), 2.88 (2H, br, CH$_2$N), 3.10–3.60 (4H, br, 2×(CH$_3$)$_2$CH+CHH indole),

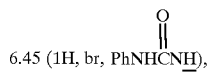

6.45 (1H, br, PhNHCNH), 6.94 (1H, br, indole CH),

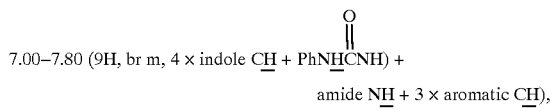

7.00–7.80 (9H, br m, 4 × indole CH + PhNHCNH) + amide NH + 3 × aromatic CH), 10.90 (1H, br s, indole NH);

IR (film): 3287, 2925, 1668, and 1519 cm$^{-1}$;

MS m/e (CI) 517 (M$^+$+H); Analysis C32H44N4O2, C, H, N; mp 229–231° C.;

$$\alpha \frac{20}{D} = 2° (c = 0.25, \text{MeOH}).$$

EXAMPLE 17

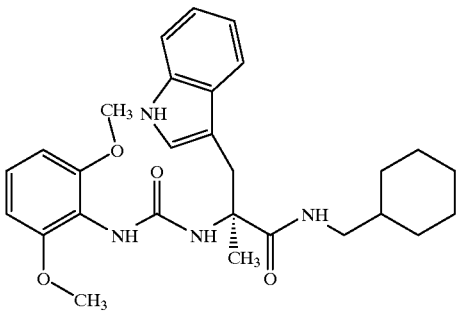

Example 17 was prepared as for Scheme 5 using cyclohexylmethylamine and 2,6-dimethoxy phenylisocyanate.

Example 17 was isolated as a white amorphous solid (70 mg).

$^1$H NMR (CDCl$_3$); δ 0.90 (2H, m), 1.20 (3H, m), 1.30 (2H, m), 1.40 (1H, m), 1.65 (3H, s), 1.70 (2H, m), 2.90 (1H, m), 3.05 and 3.45 (2H, ABq, J=15 Hz), 3.20 (1H, m), 3.58 (6H, s), 5.20 (1H, s), 5.70 (1H, s), 6.45 (2H, m), 6.82 (1H, s), 6.90 (1H, br s), 7.00 (1H, br s), 7.15 (2H, m), 7.30 (1H, d, J=6 Hz), 7.45 (1H, d, J=6 Hz), 8.10 (1H, br s);

IR (CDCl$_3$, film): 3306, 3050, 2924, 1668, 1652, 1594, and 1258 cm$^{-1}$;

Analysis calculated for C$_{28}$H$_{36}$N$_4$O$_4$: C, 68.27; H, 7.37; N, 11.37.

Found: C, 68.21; H, 7.55; N, 11.01.

SCHEME 6

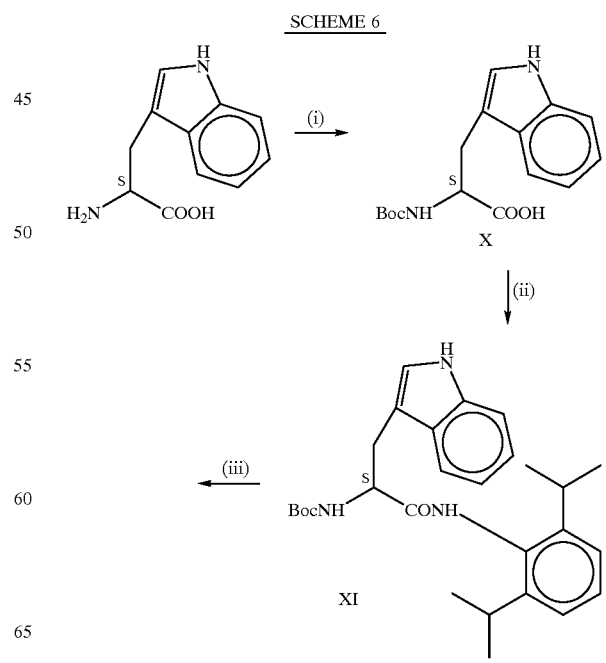

37
-continued

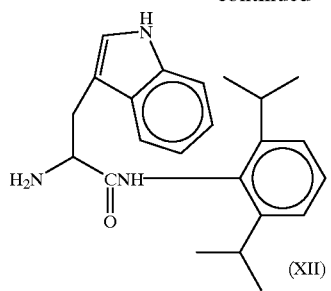

(XII)

↓ (iv)

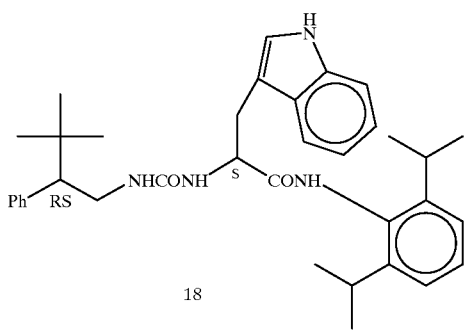

18

Reagents and Conditions:
i) Boc₂O, 10% Na₂CO₃, dioxan
ii) HBTU, 2,6-diisopropylphenylamine, DIPEA, DMF
iii) TFA, DCM
iv) α-t-butyl benzyl isocyanate, THF Synthesis of Example 18

Step 1

To a solution of (S)-tryptophan (5.1 g, 25 mmol) in 10% Na$_2$CO$_3$ (aq) (61 mL) and dioxan (150 mL) was added di tertiary butyl dicarbonate (5.67 g, 26 mmol), and the mixture was stirred for 18 hours. The solvent was removed in vacuo, and the residue was taken up in water and EtOAc. The mixture was acidified to pH 2–3 and extracted with EtOAc, dried (MgSO$_4$), and concentrated in vacuo to yield X as a white foam (7.6 g, 100%).

$^1$H NMR (CDCl$_3$): δ 1.43 (9H, s, C(CH$_3$)$_3$), 3.32 (2H, m, CH$_2$ indole), 4.66 (1H, m, αCH), 5.06 (1H, m, NH), 7.02 (1H, s, ArH), 7.10 (1H, t, ArH), 7.20 (1H, t, ArH), 7.35 (1H, d, 8 Hz, ArH), 7.60 (1H, d, 7.6 Hz, ArH), 8.14 (1H, br s, NH indole).

Step 2

To a mixture of the acid X (3.04 g, 10 mmol), HBTU (3.79 g, 10 mmol), and diisopropyl ethyl amine (3.77 g, 30 mmol) in DMF (100 mL) which had been stirred for 20 minutes was added diisopropyl aniline, and the mixture was stirred for a further 18 hours. The solvent was removed in vacuo, and the residue was taken up in EtOAc and washed with ammonium chloride saturated solution, brine, dried (MgSO$_4$), and concentrated in vacuo. The residue was purified on normal phase silica with 2.5% MeOH in DCM to yield XI (1.39 g, 30%).

$^1$H NMR (CDCl$_3$): δ 0.98–1.06 (12H, m, [(CH$_3$)$_2$CH]$_2$), 1.46 (9H, s, C(CH$_3$)$_3$), 2.7 (2H, m, [CH(CH$_3$)$_2$]$_2$), 3.34 (2H, dd, 3.6 and 8 Hz, CH$_2$ indole), 4.70 (1H, m, αH), 5.20 (1H, br s, CNH), 7.09–7.27 (7H, m, 6ArH + CNH), 7.39 (1H, d, 8.0 Hz, ArH), 7.75 (1H, d, 8.0 Hz, ArH), 8.10 (1H, s, indole NH); IR (film): 3289.0, 2966.0, 1694.9, 1668.0, 1505.0, 1366.0, 1250.0, 1167.0, 910.0, and 739.0 cm$^{-1}$;

MS m/e (Fab) 464 (M+H$^+$); Analysis C$_{28}$H$_{37}$N$_3$O$_3$, C, H, N; mp 98–100° C.

Step 3

XI (1.0 g, 2.2 mmol) was dissolved in formic acid (30 mL) and stirred for 5 hours. The mixture was basified with dilute sodium hydroxide solution to pH 14 and extracted with EtOAc, dried (MgSO$_4$), and concentrated in vacuo to give XII (745 mg, 95%) as a crude yield which was used without further purification in the next step.

EXAMPLE 18

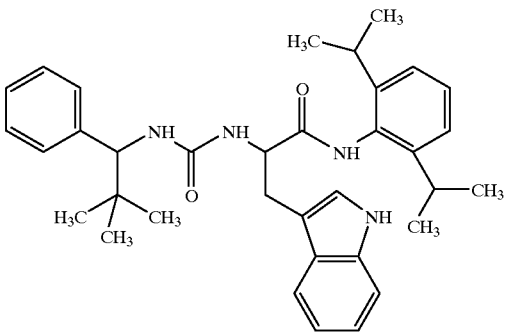

N-(2,6-Diisopropyl-phenyl)-2-[3-2,2dimethyl-1-phenyl-propyl)-ureido]-3-(1H-indol-3-yl)-propionamide To a solution of the amine XII (51.0 g, 0.14 mmol) in THF (50 mL) was added α-t-butyl benzyl isocyanate (27 mg, 0.14 mmol), and the mixture was stirred at room temperature for 15 hours. The solvent was removed under reduced pressure and the residue purified by column chromatography using 1:1 EtOAc/heptane as eluant to yield 18 as a white solid (>7 mg, >10%).

$^1$H NMR (CDCl$_3$): δ 0.81 and 0.85 (9H, 2×s, t-butyl), 0.93 (6H, d, 7.20 Hz, (CH$_3$)$_2$CH), 1.02 (6H, d, 6.8 Hz, (CH$_3$)$_2$CH), 2.58–2.68 (2H, m, [(CH$_3$)$_2$CH]$_2$), 3.2–3.7 (2H, m, CH$_2$ indole), 4.40–4.50 (1H, m, αH), 4.8–5.5 (3H, m,CNH × 2 and PhCHC(CH$_3$)$_3$), 6.7–6.8 (1H, m, CNH), 7.0–7.26 (11H, m, 11ArH), 7.4 and 7.44 (1H, 2×d, ArH), 7.65–7.75 (1H, m, 1ArH), 7.85 and 7.05 (1H, 2×br s, indole NH); IR (film): 3387.7, 3296.8, 1653.8, 1663.3, and 1552.8 cm$^{-1}$;

Analysis C$_{35}$H$_{44}$N$_4$O$_2$, C, H, N; mp 160–161° C.

SCHEME 7

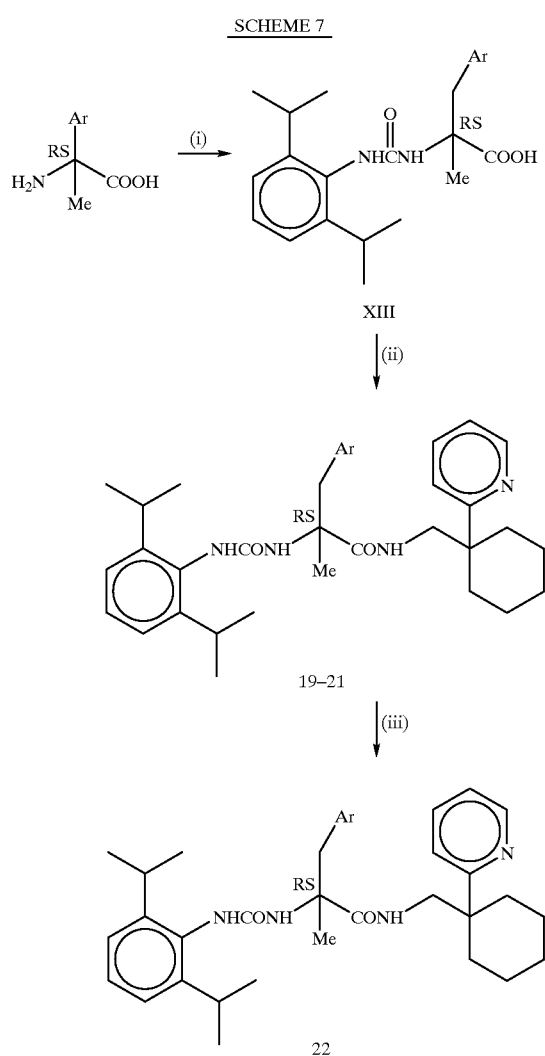

Reagents and Conditions:
i) 2,6-diisopropyl phenyl isocyanate, DMF, 60° C.
ii) Intermediate II, HBTU, DIPEA, DMF
iii) Pd/C, H$_2$, EtOH Table for Scheme 7

| Example No. | Ar |
|---|---|
| 19 | 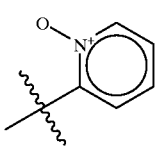 |
| 20 | 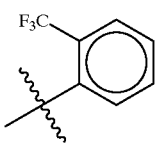 |
| 21 | 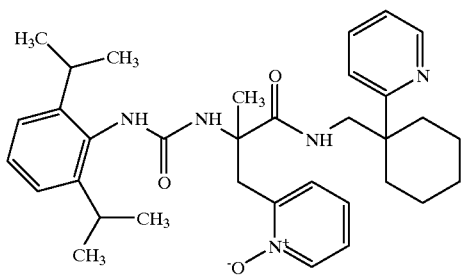 (O$_2$N-phenyl) |
| 22 | (pyridin-2-yl) |

Synthesis of Example 19

Step 1

To a suspension of the racemic amino acid (500 mg) in THF (10 mL) was added NEt$_3$ (244 mg) followed by the isocyanate (250 mg). The reaction mixture was refluxed for 4 days, evaporated to dryness, and the residue partitioned between EtOAc and 0.1 M HCl to yield the crude acid XIII (Ar=2-pyridine-N-oxide) as a yellow gum (405 mg). The compound was taken without purification onto the next step.

EXAMPLE 19

2-[3-(2,6-Diisopropyl-phenyl)-ureido]-2-methyl-3-(1-oxy-pyridin-2-yl)-N-(1-pyridin-2-yl-cyclohexylmethyl)-propionamide To a solution of the acid XIII (Ar=2-pyridine-N-oxide) (200 mg), HBTU (198 mg) and Intermediate II (100 mg) in DMF (3 mL) was added DIPEA (135 mg). The reaction mixture was stirred at room temperature for 2 days, evaporated to dryness, and the residue partitioned between EtOAc/H$_2$O to yield the crude product as a yellow gum. This was then purified by column chromatography to yield Example 19 as a white amorphous solid (195 mg).

$^1$H NMR (CDCl$_3$): δ 0.95 (2H, br s), 1.05 (2H, br s), 1.20–1.60 (8H, m), 1.70 (3H, br s), 2.20 (2H, m), 3.10–3.50 (4H, m), 5.50 (1H, s), 7.00–7.20 (5H, m), 7.40 (3H, m), 7.60 (2H, m), 7.80 (1H, br s), 8.60 (1H)s;

IR (CDCl$_3$, film): 3253, 3050, 2931, 1667, 1661, 1531, and 1441 cm$^{-1}$;

Analysis for C$_{34}$H$_{45}$N$_5$O$_3$·0.5 CH$_2$Cl$_2$; Calculated: C, 67.47; H, 7.55; N, 11.40. Found: C, 67.89; H, 7.58; N, 11.63.

Synthesis of Example 20

Step 1

As for Step 1 in synthesis of Example 19, yield of XIII (Ar=2-trifluoromethyl phenyl) was 280 mg. Used without purification in the next step.

EXAMPLE 20

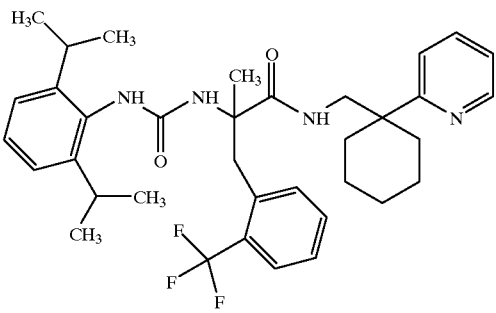

2-[3-(2,6-Diisopropyl-phenyl)-ureido]-2-methyl-N-(1-pyridin-2-yl-cyclohexylmethyl)-3-(2-trifluoromethyl-phenyl)-propionamide As for Step 2 in synthesis of Example 19, yield of Example 20 was 100 mg (amorphous solid).

$^1$H NMR (CDCl$_3$): δ 0.90 (2H, br s), 1.10 (12H, br s), 1.30–1.60 (8H, m), 1.55 (3H, s), 2.00 (2H, m), 3.10 (1H, br s), 3.30–3.50 (3H, m), 5.10 (1H, s), 5.50 (1H, s), 7.10–7.30 (9H, m), 7.50 (1H, d, J=8 Hz), 7.65 (1H, t, J=7 Hz), 8.50 (1H, d, J=2 Hz);

IR (CDCl$_3$, film): 3334, 3050, 2932, 1668, 1651, 1538, and 1311 cm$^{-1}$;

Analysis for C$_{36}$H$_{45}$F$_3$N$_4$O$_2$; Calculated: C, 69.43; H, 7.28; N, 8.99. Found: C, 69.43; H, 7.38; N, 8.70.

Synthesis of Example 21

Step 1

As for Step 1 in synthesis of Example 19, yield of XIII (Ar=2-nitrophenyl) was 450 mg. Used without purification in the next step.

EXAMPLE 21

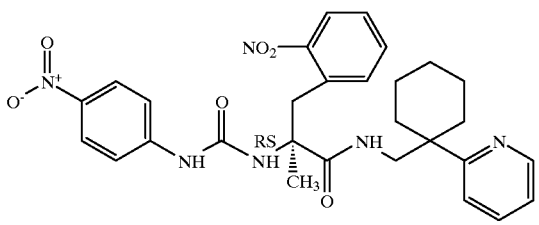

2-Methyl-3-(2-nitro-phenyl)-2-[3-(4-nitro-phenyl)-ureido]-N-(1-pyridin-2-yl-cyclohexylmethyl)-propionamide As for Step 2 in synthesis of Example 19, yield of Example 21 was 80 mg (amorphous white solid).

$^1$H NMR (CDCl$_3$): δ 0.90 (2H, br s), 1.10 (12H, br s), 1.30–1.50 (8H, m), 1.60 (3H, s), 2.10 (2H, m), 3.10 (1H, m), 3.30–3.60 (3H, m), 5.50 (2H, br s), 7.10 (4H, m), 7.30 (3H, m), 7.35 (2H, d, J=8 Hz), 7.65 (2H, m), 8.60 (1H, d, J=2 Hz);

IR (CDCl$_3$, film): 3335, 3050, 2931, 1667, 1651, 1527, and 1351 cm$^{-1}$;

Analysis for C$_{35}$H$_{45}$N$_5$O$_4$·0.2 heptane: Calculated: C, 70.53; H, 7.84; N, 11.30. Found: C, 70.92; H, 7.91; N, 11.06.

EXAMPLE 22

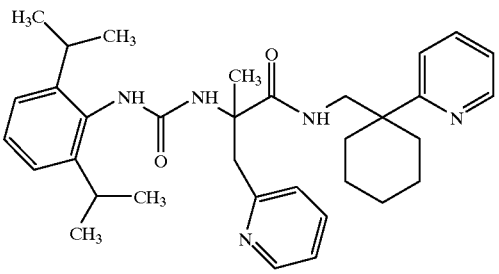

2-[3-(2,6-Diisopropyl-phenyl)-ureido]-2-methyl-3-pyridin-2-yl-N-(1-pyridin-2-yl-cyclohexylmethyl)-propionamide To a solution of the N-oxide 19 (153 mg, 0.27 mmol) in ethanol (50 mL) was added 10% Palladium on Carbon, and the reaction mixture was shaken on a Parr hydrogenation apparatus under 55 psi of hydrogen at 35° C. for 20 hours. The reaction mixture was filtered through celite, and the filtrate was concentrated in vacuo. The residue was purified on normal phase silica eluting with a gradient of heptane to 1:1 heptane:EtOAc to yield 22 (24.9 mg, 16.7%).

$^1$H NMR (CDCl$_3$): δ0.99–1.05 (6H, m, (C$\underline{H}_3$)$_2$CH), 1.05–1.20 (6H, m (CH$_3$)$_2$CH), 1.31–1.69 (8H, m, cyclohexyl), 1.56 (3H, s, αC$\underline{H}_3$), 2.12–2.21 (2H, m, cyclohexyl), 2.72–2.75 (1H, m, (CH$_3$)C$\underline{H}$), 3.10–3.20 (3H, m, pyridyl, C$\underline{H}_2$, (CH$_3$)$_2$C$\underline{H}$),

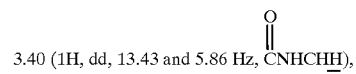

3.40 (1H, dd, 13.43 and 5.86 Hz, CNHCH$\underline{H}$),

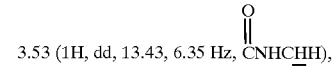

3.53 (1H, dd, 13.43, 6.35 Hz, CNHC$\underline{H}$H),

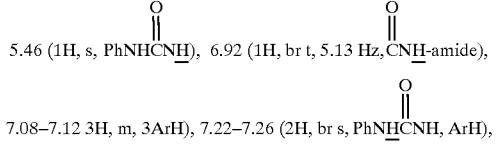

5.46 (1H, s, PhNH$\underline{C}$N$\underline{H}$), 6.92 (1H, br t, 5.13 Hz, CN$\underline{H}$-amide), 7.08–7.12 3H, m, 3ArH), 7.22–7.26 (2H, br s, PhN$\underline{H}$CNH, ArH), 7.27–7.48 (4H, m, 4ArH), 7.62–7.66 (2H, m, 2ArH), 8.60–8.62 (1H, m, ArH);

IR (film): 3278.0, 2929.0, 1668.0, 1590.0, 1520.0, 1471.0, and 1208.0 cm$^{-1}$; MS m/e (APCl) 556.0 (M+H$^+$); Analysis C$_{34}$H$_{45}$N$_5$O$_2$·0.25 H$_2$O, C, H, N;

mp 185–186° C; HPLC R.T.=6.16, C$^{18}$ reverse phase, 40% to 100% MeCN:TFA/H$_2$O:TFA.

SCHEME 8

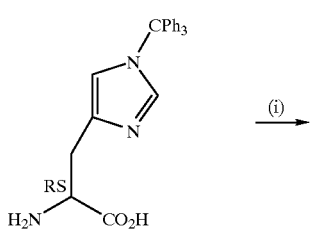

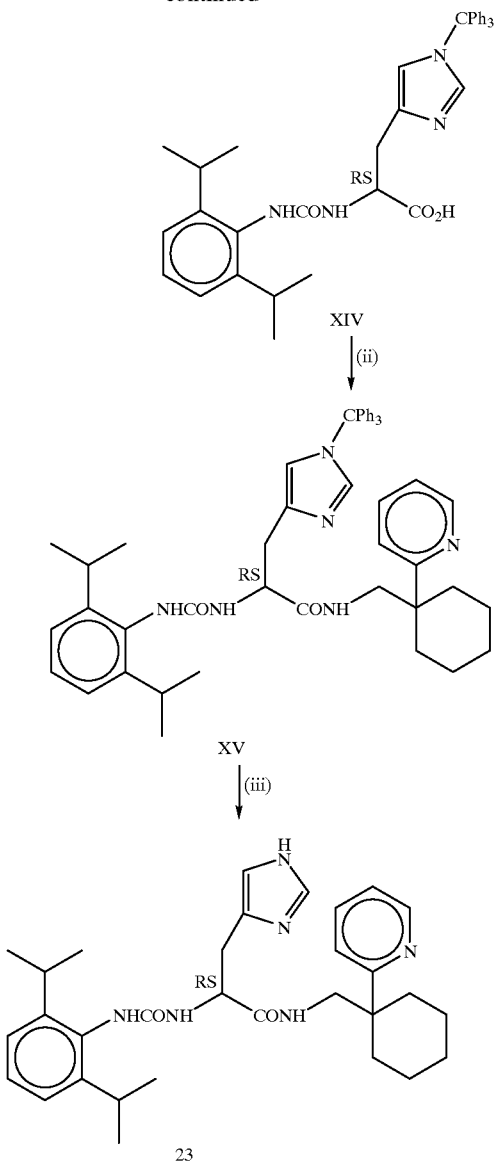

Reagents and Conditions:
i) 2,6-Diisopropyl phenyl isocyanate, DMF, 60° C.
ii) Intermediate II, HBTU, DIPEA, DMF
iii) Formic acid, DCM Synthesis of Example 23

Step 1

To a mixture of N-trityl histidine (0.99 g, 2.5 mmol) in THF (70 mL) and DMF (20 mL) was added pyridine (396 mg, 5 mmol) followed by diisopropyl phenyl isocyanate (1.02 g, 5 mmol), and the mixture was refluxed for 1.5 hours. The reaction mixture was allowed to cool to room temperature before being taken up in EtOAc and washed with 1N HCl (aq), dried (MgSO$_4$), and concentrated in vacuo. The residue was used crude for the next step (2.20 g, 100%) XIV.

Step 2

To a solution of the acid XIV (500 mg, 0.81 mmol) in DMF (50 mL) was added HBTU (309 mg, 0.81 mmol) and diisopropyl ethyl amine (316 mg, 2.43 mmol), and the mixture was stirred for 5 minutes. The amine II (155 mg, 0.81 mmol) was then added to the reaction mixture which was then stirred for a further 2 hours. The mixture was taken up in EtOAc and washed with NaHCO$_3$ (aq), brine, dried (MgSO$_4$), and concentrated in vacuo. The residue was purified on normal phase silica eluting with a gradient of heptane:EtOAc 1:1 to EtOAc and then repurified on reverse phase silica eluting with MeOH to yield pure XV (120 mg, 7.8%).

$^1$H NMR (CDCl$_3$): δ0.90–1.64 (20H, 4×m, [(CH$_3$)$_2$CH]$_2$ and cyclohexyl -8H), 2.05–2.18 (2H, m, cyclohexyl), 2.60–2.70 (1H, m, (CH$_3$)$_2$CH), 2.96 (1H, dd, 14.65 and 4.39 Hz, indole CHH), 3.35 (1H, dd, 5.86 and 13.19 Hz, CNHCHH), 3.45 (1H, dd, 6.35 and 13.43 Hz, CNHCHH), 3.0–3.25 (2H, m, CHH indole and (CH$_3$)$_2$CH), 4.47 (1H, m, 5.58–5.65 (1H, m,CNH), 6.05–6.15 (1H, m, CNH), 6.5 (1H, s, PhNHCNH), 6.85–7.04 (1H, m, 1ArH), 7.03 (8H, t, 1.46 Hz, 8ArH), 7.11 (2H, d, 7.82 Hz, 2ArH), 7.20–7.38 (14H, m, 14ArH), 7.57 (1H, td, 1.71 and 7.81 Hz, ArH), 8.53 (1H, d, 3.17 Hz, pyridyl H).

EXAMPLE 23

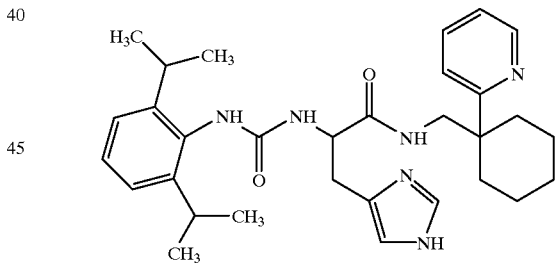

2-[3-(2,6-Diisopropyl-phenyl)-ureido]-3-(1H-imidazole-4-yl)-N-(1-pyridin-2-yl-cyclohexylmethyl)-propionamide A mixture of XV (120 mg, 0.15 mmol) in formic acid (5 mL) and DCM (50 mL) was stirred at room temperature for 24 hours. The solvents were removed in vacuo, and the residue was taken up in water 50 mL) and washed with EtOAc. The aqueous layer was concentrated in vacuo at below 40° C., and the residue was taken up in DCM and ether and concentrated in vacuo to obtain 23 as a solid (57.8 mg, 65.4%).

$^1$H NMR (DMSO): δ1.05–1.60 (8H, m, cyclohexyl), 1.06 (12H, d, 6.84 Hz, [(CH3)$_2$CH]$_2$), 2.10–2.13 (2H, m, cyclohexyl),

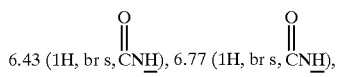

2.67–2.72 (1H, m, CNHCH<u>H</u>), 2.80–2.98 (1H, m, C<u>H</u>(CH₃)₂), 3.0–3.16 (1H, m, C<u>H</u>(CH₃)₂),

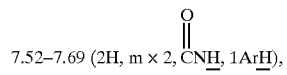

3.18–3.21 (1H, m, CNHCH<u>H</u>), 3.31–3.41 (2H, obscured by water peak, C<u>HH</u> imidazole), 4.38 4.42 (1H, m, α<u>H</u>), 6.43 (1H, br s, CN<u>H</u>), 6.77 (1H, br s, CN<u>H</u>), 7.08 (2H, d, 7.32 Hz, 2Ar<u>H</u>), 7.18–7.21 (2H, m 2Ar<u>H</u>), 7.34 (1H, d, 8.06 Hz, 1Ar<u>H</u>), 7.52–7.69 (2H, m × 2, CN<u>H</u>, 1Ar<u>H</u>), 7.71 (1H, t, 7.81 Hz, 1Ar<u>H</u>), 8.56 (1H, d, 4.15 Hz, Ar<u>H</u>), 12.00 (1h, br s, indole N<u>H</u>);

IR (film): 3291.0, 2929.0, 1733.0, 1645.0, 1589.0, 1539.0, 1471.0, 1362.0, and 1238.0 cm$^{-1}$; MS m/e (E1+) 530 (M$^+$) 531 (M+H$^+$);

Analysis for $C_{31}H_{42}N_6O_2 \cdot 0.7$ HCOOH; mp 114–116° C.; HPLC R.T.=17.045 and 17.36, $C^{18}$ reverse phase 10% to 80% MeCN:TFA/H₂O:TFA.

SCHEME 9

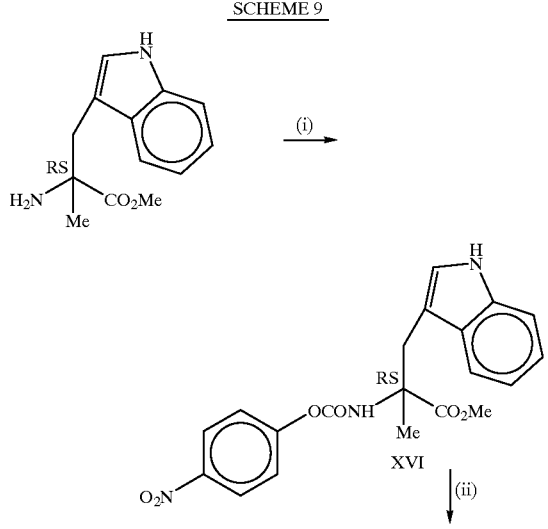

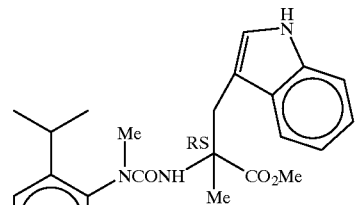

XVII

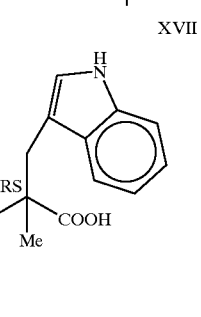

XVIII

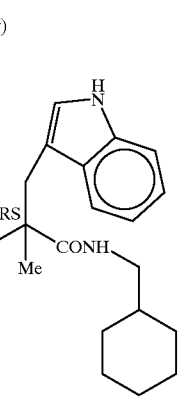

24

Reagents and Conditions:
i) P-nitrophenyl chloroformate, NEt₃, THF
ii) 2,6-Diisopropyl phenyl N methyl amine, NEt₃, toluene, Δ
iii) LiOH, H₂O, MeOH, Δ
iv) HBTU, cyclohexyl methyl amine, DIPEA, DMF Synthesis of Example 24

Step 1

To a cooled (0° C.) solution of α-Me (R,S) tryptophan methyl ester (2 g, 8.6 mmol) in dry THF (100 mL) was added dropwise p-nitro phenyl chloroformate (1.74 g, 8.6 mmol) followed by triethyl amine (1.2 mL, 8.6 mmol) dropwise. The reaction mixture was warmed to room temperature and stirred for 2 hours. The solution was then taken up in EtOAc and washed with 1N HU (aq), brine, dried (MgSO₄), and concentrated in vacuo. The residue was purified on normal phase silica with a gradient of heptane to 7:3 heptane/EtoAc as eluent to yield XVI (1.85 g, 54%) which was used without further purification in the next step.

Step 2

To a solution of the carbamate XVI (318 mg, 0.8 mmol) in toluene (60 mL) was added N-methyl diisopropyl aniline (XX) (153 mg, 0.8 mmol) followed by triethyl amine (1 mL), and the mixture was refluxed for 9 hours. The mixture was taken up in EtOAc and washed with 1N HCl (aq), brine, NaHCO$_3$ (aq), dried (MgSO$_4$), and concentrated in vacuo. The residue was purified by normal phase chromatography eluting with a gradient of heptane to 6:4 heptane/EtOAc to yield pure XVII (213 mg, 59.2%).

$^1$H NMR (CDCl$_3$): δ0.77, 0.86, 1.10, 1.14 (12H, 4×d, 6.84, 6.59, 7.08, 6.84 Hz, respectively, [(CH$_3$)$_2$CH]$_2$), 1.68 (3H, s, αC$\underline{H}_3$), 2.86 (1H, q$^n$, 6.84 Hz, (CH$_3$)$_2$C$\underline{H}$), 2.98 (1H, q$^n$, 6.84 Hz, (CH$_3$)$_2$C$\underline{H}$), 3.03 (1H, d, 14.40 Hz, CH$\underline{H}$ indole), 3.08 (3H, s, N-C$\underline{H}_3$), 3.13 (1H, d, 14.40 Hz, CH$\underline{H}$ indole), 3.63 (3H, s, CO$_2$C$\underline{H}_3$),

4.68 (1H, s, N(CH$_3$)$\overset{\overset{O}{\|}}{C}$N$\underline{H}$), 6.23 (1H, d, 2.44 Hz, 1Ar$\underline{H}$), 6.99 (1H, t, 7.08 Hz, 1Ar$\underline{H}$), 7.09–7.16 (3H, m, 3Ar$\underline{H}$), 7.25–7.27 (1H, m, Ar$\underline{H}$), 7.31–7.36 (2H, m, 2Ar$\underline{H}$), 7.77 (1H, s, indole N$\underline{H}$);

IR (film): 3280.0, 2963.0, 1737.0, 1650.0, 1508.0, 1459.0, 1343.0, 1256.0, 1105.0, 910.0, and 739.0 cm$^{-1}$.

Step 3

To a solution of the ester XVII (151.6 mg, 0.34 mmol) in THF (20 mL) was added lithium hydroxide (529 mg, 12.6 mmol) as a solution in water (30 mL) followed by methanol (10 mL), and the reaction mixture was refluxed for 7 hours. The mixture was concentrated in vacuo to remove only the organic solvents, and the aqueous mixture remaining was extracted with ether. The aqueous layer was acidified to pH 1 with HCl (aq) and re-extracted with EtOAc, dried (MgSO$_4$), and concentrated in vacuo to yield pure acid XVIII (105 mg, 71%).

$^1$H NMR (CDCl$_3$): δ0.69 (3H, d, 6.84 Hz, C$\underline{H}_3$CH), 0.82 (3H, d, 6.84 Hz, C$\underline{H}_3$CH), 1.09 (3H, d, 6.84 Hz, C$\underline{H}_3$CH), 1.13 (3H, d, 6.84 Hz, C$\underline{H}_3$CH), 1.65 (3H, s, αC$\underline{H}_3$), 2.72 (1H, q$^n$, 7.08 Hz, (CH$_3$)$_2$C$\underline{H}$), 2.79 (1H, q$^n$, 6.59 Hz, (CH$_3$)$_2$C$\underline{H}$), 2.99 (1H, d, 14.89 Hz, indole CH$\underline{H}$), 3.32 (1H, d, 14.89 Hz, CH$\underline{H}$ indole), 3.10 (3H, s, N-C$\underline{H}_3$),

4.72 (1H, s, NMeC$\overset{\overset{O}{\|}}{N}\underline{H}$), 6.46 (1H, d, 2.69 Hz, indole H2), 6.93 (1H, t, 7.08 Hz, indole H5), 6.99 (1H, t, 4.15 Hz, indole H6), 7.08–7.33 (5H, m, 5Ar $\underline{H}$), 7.79 (1H, br s, indole N$\underline{H}$);

IR (film): 3383.0, 1634.0, 1505.0, and 1053.0 cm$^{-1}$;

MS m/e (APCI) 436.7 (M+H$^+$).

EXAMPLE 24

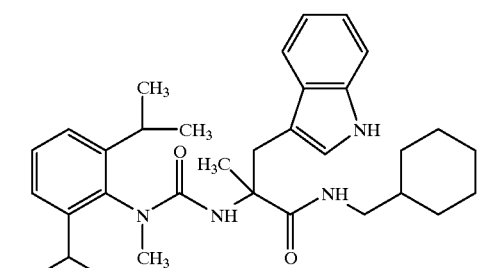

N-Cyclohexylmethyl-2-[3-(2,6-diisopropyl-phenyl)-3-methyl-ureido]-3-(1H-iindol-3-yl)-2-methyl-propionamide To a solution of the acid XVIII (104 mg, 0.24 mmol), HBTU (91 mg, 0.24 mmol) and diisorpropyl ethyl amine (93 mg, 0.72 mmol) which had been stirred for 10 minutes was added cyclohexyl methyl amine (54 mg, 0.48 mmol), and the mixture was stirred for an hour. The reaction mixture was taken up in EtOAc and washed with 1N HCl (aq), NaHCO$_3$ (aq), brine, dried (MgSO$_4$), and concentrated in vacuo. The residue was purified by normal phase chromatogrlaphy eluting with a gradient of heptane to 1:1 heptane/EtOAc to yield pure 24 (56 mg, 45%), mp 214–216° C.

$^1$H NMR (CDCl$_3$): δ0.68, 0.95, 1.11, 1.15 (12H, 4×d, 7.08 Hz, [(C$\underline{H}_3$)$_2$CH]$_2$), 0.82–0.93 (2H, m, cyclohexyl), 1.30–1.36 (2H, m, cyclohexyl), 1.56–1.66 (6H, m, cyclohexyl), 1.66 (3H, s, αC$\underline{H}_3$), 2.76–2.83 (1H, m, (CH$_3$)$_2$C$\underline{H}$), 2.78 (1H, d, 14.40 Hz, CH$\underline{H}$ indole), 2.90 (1H, q$^n$, 6.84 Hz, (CH$_3$)$_2$C$\underline{H}$),

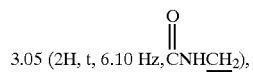
3.05 (2H, t, 6.10 Hz, $\overset{\overset{O}{\|}}{C}$NHC$\underline{H}_2$), 3.08 (3H, s, N-C$\underline{H}_3$), 3.37 (1H, d, 14.65 Hz, CH$\underline{H}$ indole),

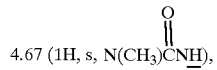
4.67 (1H, s, N(CH$_3$)$\overset{\overset{O}{\|}}{C}$N$\underline{H}$), 6.19 (1H, d, 2.4 Hz, Ar$\underline{H}$),

6.83 (1H, br t, $\overset{\overset{O}{\|}}{C}$N$\underline{H}$CH$_2$), 6.95 (1H, t, 7.81 Hz, Ar$\underline{H}$), 7.08 (2H, t, 7.57 Hz, 2Ar$\underline{H}$), 7.16 (1H, d, 7.57 Hz, Ar$\underline{H}$), 7.23 (1H, d, 8.3 Hz, Ar$\underline{H}$), 7.31–7.36 (2H, m, 2Ar$\underline{H}$), 7.73 (1H, br s, indole N$\underline{H}$);

IR (film): 3307.0, 2925.0, 1625.0, 1505.0, 1339.0, and 739.0 cm$^{-1}$; MS m/e (APCI) 531.7 (M+H$^+$);

Analysis for C$_{33}$H$_{46}$N$_4$O$_2$, C, H, N; mp 214–216° C.; HPLC R.T.=19.77, C$^{18}$ reverse phase, 40% to 100% MeCN:TFA/H$_2$O:TFA.

SCHEME 10

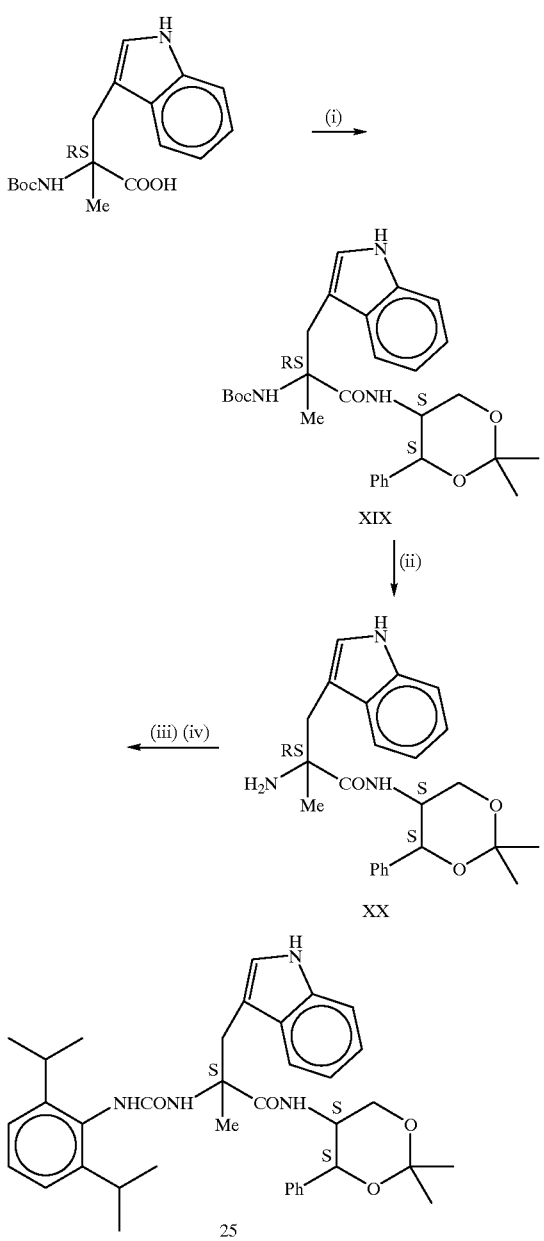

Reagents and Conditions:
i) DCC, HOBt, amine, DCM
ii) HCl gas, Et$_2$O
iii) 2,6-Diisopropyl phenyl isocyanate, EtOAc, Δ
iv) Separate diastereoisomers by chromatography

Synthesis of Example 25

Step 1

A solution of BOC(RS)-(α-methyl)tryptophan (3.00 g, 9.4 mmol), (4S,5S)-(+)-5-amino-2,2-dimethyl-4-phenyl-1, 3-dioxane (1.95 g, 9.4 mmol), 1-hydroxybenzotriazole hydrate (1.27 g, 9.4 mmol) in dichloromethane (100 mL) was cooled to 0° C. and stirred 5 minutes at which time dicyclohexylcarbodiimide (1.94 g, 9.4 mmol) was added, and the reaction mixture was stirred 10 days at room temperature. The reaction mixture was concentrated to dryness, taken up in ethyl acetate, washed with 10% aqueous potassium carbonate, saturated aqueous sodium chloride, dried over magnesium sulfate, filtered, and concentrated to a yellow oil. The oil was filtered through silica gel using ethyl acetate as eluant. The product (Intermediate XIX) was obtained as a white foam, 4.70 g.

FAB mass spectrum $(M+H^+)^+ = 508.6$.

Analysis for $C_{29}H_{37}N_3O_5$ (507.63).

Step 2

Anhydrous hydrogen chloride gas was bubbled into a solution of the BOC-amide-acetonide (1.00 g, 2.0 mmol) (Intermediate XIX) for about 3 minutes. The reaction mixture was allowed to stand at room temperature for 3 hours and no starting material remained by tlc. The reaction mixture was concentrated in vacuo to a light tan solid. The solid was partitioned between 0.1N sodium hydroxide and ethyl acetate, the ethyl acetate was dried over magnesium sulfate, filtered, and concentrated to a white foam. The white foam was filtered through silica gel using ethyl acetate as eluant. The product (Intermediate XX) was obtained as a white solid, 0.33 g.

E1 mass spectrum M+=407.

Parent molecular weight=407.5.

Analysis calculated for $C_{24}H_{29}N_3O_3 \cdot 0.33 H_2O$, C, H, N.

A by-product of the reaction was the aminodiol 0.25 g. A larger run employing 3.4 g of the BOC-amide-acetonide yielded 2.18 g of the amino acetonide and 0.58 g of the aminodiol.

EXAMPLE 25

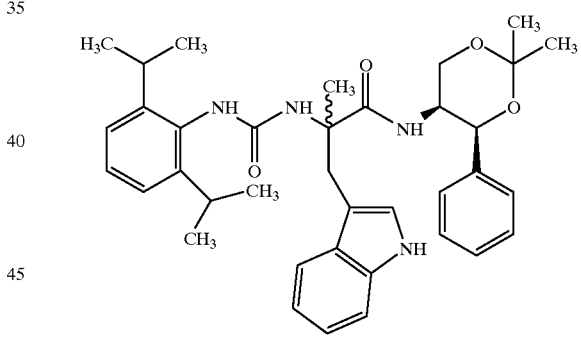

2-[3-(2,6-Diisopropyl-phenyl)-ureido]-N-(2,2-dimethyl-4-phenyl-[1,3]dioxan-5-yl)-3-(1H-indol-3-yl)-2-methyl-propionamide A solution of the amino acetonide (0.40 g, 0.98 mmol) (Intermediate XX) and 2,6-diisopropyl phenyl isocyanate (0.23 g, 1.13 mmol) in ethyl acetate (30 mL) was briefly heated to achieve solution. The reaction mixture was allowed to stand 2 days at room temperature and was then concentrated to a viscous oil. The oil was chromatographed on silica gel using ethyl acetate as eluant yielding 0.288 g of the less polar product (Example 25).

FAB mass spectrum $(M+H^+)^+ = 611.2$.

Analysis for $C_{37}H_{46}N_4O_4 \cdot 0.33 C_4H_8O_2$, C, H, N.

Parent molecular weight=610.78.

Also obtained was 0.237 g of the more polar product.

FAB mass spectrum $(M+H^+)^+ = 611.1$.

EXAMPLE 26

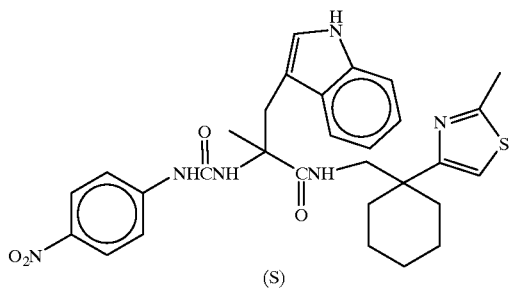

(S)

Example 26 was prepared as for Scheme 3 using Intermediate XXI. Example 26 was isolated in 24.5% yield.

$^1$H NMR (DMSO): δ 1.12–1.55 (8H, mm, cyclohexyl), 1.47 (3H, s, αC$\underline{H}_3$), 1.96–2.03 (2H, m, cyclohexyl), 2.56 (3H, s, N=C—C$\underline{H}_3$), 3.06 (1H, dd, J = 5.37 and 13.19 Hz, $\overset{\overset{\displaystyle O}{\|}}{C}$NHCH$\underline{H}$), 3.27 (1H, dd, J = 6.59 and 13.18 Hz, $\overset{\overset{\displaystyle O}{\|}}{C}$NHCH$\underline{H}$), 3.40 (2H, 2×d, J=15.62 and 15.14 Hz, respectively, C$\underline{HH}$ indole), 6.56 (1H, s, NH$\overset{\overset{\displaystyle O}{\|}}{C}$N$\underline{H}$αC), 6.81 (1H, t, J=7.81 Hz, indole H-5), 6.95 (1H, d, J=2.20 Hz, indole H-2), 6.98–7.00 (2H, m, indole H-6 and C$\underline{H}$-5), 7.28 (1H, d, J=8.06 Hz, Ar$\underline{H}$), 7.43 (1H, d, J=7.81 Hz, Ar$\underline{H}$), 7.46 (1H, Bt, J = 5.37 Hz, $\overset{\overset{\displaystyle O}{\|}}{C}$N$\underline{H}$CH$_2$), 7.63 (2H, d, J=9.28 Hz, p-NO$_2$Ar$\underline{H}$×2), 8.16 (2H, d, J = 9.27 Hz, p-NO$_2$ ArH × 2), 9.50 (1H, s, N$\underline{H}$$\overset{\overset{\displaystyle O}{\|}}{C}$NH), 10.83 (1H, s, indole N$\underline{H}$);

IR (film): 3342.0, 2933.4, 1704.3, 1645.0, 1555.9, 1505.0, 1456.4, 1329.0, 1112.0 cm$^{-1}$;

MS m/e (ES) 573.05 (M$^+$), 575.08 (M+H$^+$);

Analysis C$_{30}$H$_{34}$N$_6$O$_4$S: C,H,N;

mp 205–209° C.;

HPLC R.T.=10.85, C$^{18}$ reverse phase, 40% to 100% MeCN:TFA/H$_2$O:TFA.

EXAMPLE 27

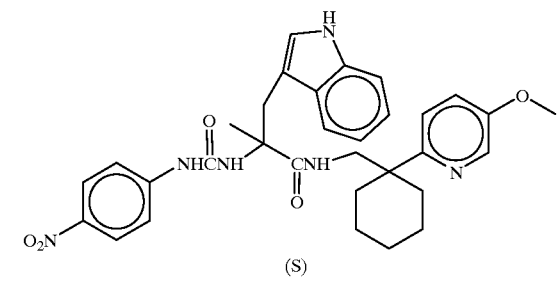

(S)

Example 27 was prepared as for Scheme 3 using Intermediate XXII. Example 27 was isolated in 26.2% yield.

$^1$H NMR (DMSO): δ 1.03–1.53 (8H, m, cyclohexyl), 1.44 (3H, s, αC$\underline{H}_3$), 2.10–2.20 (2H, m, cyclohexyl), 3.06 (1H, dd, J = 5.13 and 12.94 Hz, $\overset{\overset{\displaystyle O}{\|}}{C}$NHCH$\underline{H}$), 3.28 (1H, dd, obscured by water peak, $\overset{\overset{\displaystyle O}{\|}}{C}$NHCH$\underline{H}$), 3.38 (2H, 2×d, J=15.14 Hz, C$\underline{HH}$ indole), 3.68 (3H, s, OC$\underline{H}_3$), 6.55 (1H, s, NH$\overset{\overset{\displaystyle O}{\|}}{C}$N$\underline{H}$αC), 6.81 (1H, t, J=7.08 Hz indole H-5), 6.94 (1H, d, J=1.71 Hz, indole H2), 6.98 (1H, t, J=7.08 Hz, indole H6), 7.04 (1H, dd, J=2.93 and 8.79 Hz, indole H7), 7.19 (1H, d, J=8.79 Hz, pyridyl H3), 7.23 (1H, d, J=8.3 Hz, pyridyl H4), 7.41–7.45 (2H, m, $\overset{\overset{\displaystyle O}{\|}}{C}$N$\underline{H}$CH$_2$ and Ar$\underline{H}$), 7.62 (2H, d, J=9.23 Hz, p-NO$_2$Ar$\underline{H}$×2), 8.16 (2H, d, J=9.52 Hz, p-NO$_2$ Ar$\underline{H}$×2), 8.17–8.19 (1H, m, Ar$\underline{H}$), 9.49 (1H, s, N$\underline{H}$$\overset{\overset{\displaystyle O}{\|}}{C}$NH), 10.82 (1H, s, indole N$\underline{H}$);

IR (film): 3355.0, 2925.0, 1652.1, 1558.1, 1504.7, 1453.6, 1328.2, 1052.5 cm$^{-1}$;

MS m/e (APCI) 584.1 (M), (M+H$^+$)=585.1;

Analysis C$_{32}$H$_{36}$N$_6$O$_5$·0.3H$_2$O: C, H, N;

mp 213–215° C.;

HPLC R.T.=98.1 and 10.40, C$^{18}$ reverse phase, 40% to 100% MeCN:TFA/H$_2$O:TFA.

EXAMPLE 28

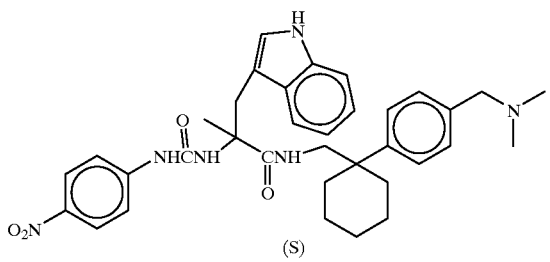
(S)

Example 28 was prepared as for Scheme 3 using Intermediate XXIII. Example 28 was isolated in 48% yield.

¹H NMR (DMSO): δ 1.10–1.23 (3H, m, cyclohexyl), 1.37–1.60 (5H, m, cyclohexyl), 1.40 (3H, s, αCH₃), 1.98–2.08 (2H, m, cyclohexyl), 2.06 (6H, s, NMe₂), 2.98 (1H, dd, J = 5.62 and 13.43 Hz, CNHCHH), 3.22 (2H, s, ArCH₂NMe₂), 3.27 (1H, dd, J = 7.08 and 14.16 Hz, CNHCHH), 3.35 (1H, d, J=14.65 Hz), CHH indole), 3.40 (1H, d, J=14.65 Hz, CHH indole), 6.49 (1H, s, NHCNHαC), 6.81 (1H, t, J=7.81 Hz, indole H5), 6.93 (1H, d, J=2.2 Hz, indole H-2), 6.98 (1H, t, J=7.08 Hz, indole H6), 7.05 (2H, d, J=8.06 Hz, 2×ArH), 7.16 (1H, bt, J = 6.35 Hz, CNHCH₂), 7.23 (2H, d, J=8.30 Hz, 2×ArH), 7.27 (1H, d, J=8.06 Hz, indole H7), 7.43 (1H, d, J=7.81 Hz, indole H4), 7.64 (2H, d, J=9.28 Hz, p-NO₂ArH×2), 8.18 (1H, d, J=9.28 Hz, 2×p-NO₂ArH), 9.45 (1H, s, NHCNH), 10.82 (1H, s, indole NH);
IR (film): 3339.0, 2930.8, 1705.3, 1651.2, 1599.0, 1505.0, 1329.0, 1112.0 (cm⁻¹);
MS m/e (APCI) 611.2 (M+H⁺);
Analysis C₃₅H₄₂N₆O₄: C, H, N;
mp 200–202° C.;
HPLC R.T.=23.35, C¹⁸ reverse phase, 10% to 80% MeCN:TFA/H₂O:TFA.

EXAMPLE 29

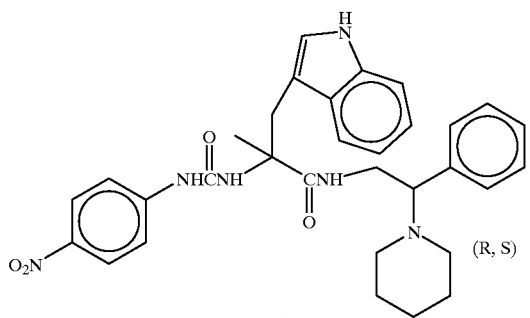
(R, S)
(S)

Example 29 was prepared as for Scheme 3 using Intermediate XXIV. Example 29 was isolated in 70% yield.

¹H NMR (DMSO): δ 1.10–1.22 (2H, m, piperidino CH's), 1.24–1.42 (4H, m, piperidino CH's), 1.39 (1.5H, s, αMe), 1.43 (1.5H, s, αMe), 2.02–2.16 (2H, m, piperidino CH's), 2.21–2.30 (2H, m piperidino CH's), 3.22–3.60 (5H, m, indole CH₂ and CONHCH₂CHN), 6.53 (0.5H, s, CONH), 6.57 (0.5H, s, CONH); 6.77–6.84 (1H, m, indole H5), 6.95–7.04 (2H, m, indole H6 and H2), 7.12–7.32 (6H, m, indole H7 and 5×ArH's), 7.45 (1H, d, J=8.1 Hz, indole H4), 7.48–7.63 (1H, m, CONHCH₂), 7.62 (2H, d, J=9.0 Hz Ar HNO₂ ring), 8.14–8.17 (2H, m, ArHNO₂ ring), 9.49 (0.5H, s, CONH), 9.50 (0.5H, s, CONH), 10.84 (0.5H, s, indole N H), and 10.87 (0.5H, s, indole NH);
IR (film): 3336.0, 2934.0, 1710.0, 1657.0, 1506.0, 1329.0, 1229.0, 1112.0, and 851.0 cm⁻¹;
MS m/e (ES+) 64.2 (20%), 205.2 (37%), 431.1 (12%), 569.2 (M+H⁺, 100%⁺);
mp 133–137° C.;
HPLC R.T.=10.57 and 10.77, C¹⁸ reverse phase, 40% to 100% MeCN:TFA/H₂O:TFA.

EXAMPLE 30

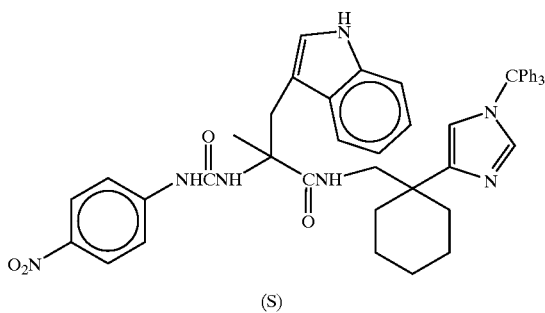
(S)

Example 30 was prepared as for Scheme 3 using Intermediate XXV. Example 30 was isolated in 83% yield.

¹H NMR (DMSO): δ 1.05–1.20 (3H, m, cyclohexyl CH), 1.30–1.42 (5H, m, cyclohexyl CH), 1.47 (3H, s, αCH₃), 1.70–1.90 (2H, m, cyclohexyl CH), 3.00–3.10 (1H, m, C HHNHCO), 3.20–3.28 (1H, m, CHHNHCO), 3.37 (1H, d, 14.4 Hz, CHH indole), 3.45 (1H, d, 14.4 Hz, CHH indole), 6.51 (1H, s, PhNHCONH or CH imidazole), 6.58 (1H, s, PhN, PhNHCONH or CH imidazole), 6.77–6.81 (1H, m, C₅—H indole), 6.93–7.04 (8H, m, 6×ArH, C₆—H indole, C₂—H indole), 7.19 (1H, s, imidazole CH), 7.27 (1H, d, 7.9 Hz, C₇—H indole), 7.32–7.39 (9H, m, ArH), 7.42 (1H, d, 8.1

Hz C$_4$—H indole), 7.56 (2H, d, 9.0 Hz, PhNO$_2$CH) 7.86 (1H, t, 5.4 Hz, NH amide), 8.07 (2H, d, 9.0 Hz, PhNO$_2$CH), 9.48 (1H, s, PhNHCO), 10.82 (1H, s, indole NH);

IR (film) 3335, 3060, 2932, 2855, 1704, 1645, 1599, 1557, 1505, 1446, 1330, 1303, 1230, 1176, 1113, 1039, 1011, 852, and 745 cm$^{-1}$;

MS m/e (APCI): 786.3 (M+H);

mp 148–154° C.;

HPLC R.T.=16.79, C$^{18}$ reverse phase, 40% to 100% MeCN:TFA/H$_2$O:TFA over 20 minutes.

EXAMPLE 31

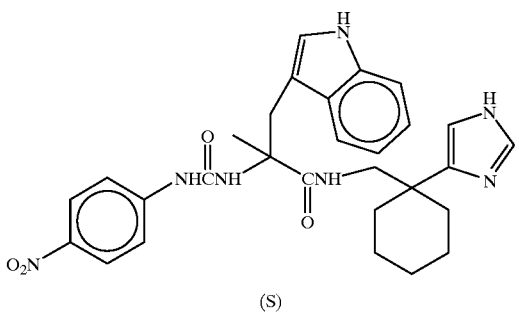

(S)

To a stirred solution of Example 30 (0.23 g, 0.29 mmol) in MeOH (50 mL) was added 2 N HCL (2 mL). The reaction mixture was refluxed for 2 hours. The solution was neutralized using 1 N NaOH and evaporated in vacuo. The residue was purified on reverse phase silica eluting with a gradient of MeOH/H$_2$O 0% to 10%. The product was eluted with 60% MeOH/H$_2$O to give Example 31 as a yellow solid (0.073 g, 44%).

$^1$H NMR (DMSO+DCL/D$_2$O): δ 1.05–1.25 (3H, m, cyclohexyl CH), 1.35–1.55 (5H, m, cyclohexyl CH), 1.36 (3H, s, αCH$_3$), 1.90–2.00 (2H, m, cyclohexyl CH), 3.10 (1H, d, 13.2 Hz, CHH-indole or CHH-cyclohexyl), 3.23 (1H, d, 13.4 Hz, CHH indole or CHH-cyclohexyl), 3.28 (2H, s, CH$_2$-indole or CH$_2$-cyclohexyl), 6.78–6.80 (1H, m, indole C$_5$—H), 6.93–6.97 (1H, m, indole C$_6$—H), 7.01 (1H, s, ArH), 7.24–7.26 (2H, m, indole C$_7$—H, Ar—H), 7.40 (1H, d, J=8.1 Hz, indole C$_4$—H), 7.59–7.61 (2H, m, PhNO$_2$CH), 8.11–8.14 (2H, m, PhNO$_2$CH), 9.05 (1H, d, 1.0 Hz, CH imidazole);

IR (film): 3356, 2935, 2859, 1699, 1652, 1597, 1557, 1505, 1458, 1331, 1303, 1232, 1208, 1195, 1177, 1112, 851, and 746 cm$^{-1}$;

MS m/e (ES$^+$ high resolution), Measured (M+H)$^+$ 544.2677, Expected (M+H)$^+$ 544.2672, Deviation (ppm)+ 0.9;

mp 150–152° C.;

HPLC R.T.=17.9 min, C$^{18}$ reverse phase, 10% to 80% MeCN:TFA/H$_2$O:TFA over 20 minutes.

EXAMPLE 32

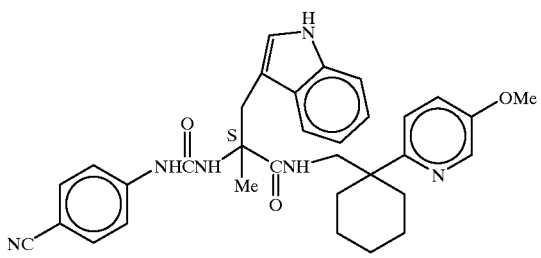

Example 32 was prepared as in Scheme 5 using Intermediate XXII; mp 110–115° C.

$^1$H NMR (DMSO): δ 1.05–1.25 (6H, m), 1.40 (3H, s), 1.40–1.50 (4H, m), 2.15 (2H, m), 3.05 and 3.25 (2H, Abq, J=15 Hz), 3.70 (3H, s), 6.40 (1H, s) 6.80 (1H, t, J=6 Hz), 6.95 (1H, s), 7.00 (1H, t, J=6 Hz), 7.20 (1H, d, J=7 Hz), 7.30 (1H, d, J=7 Hz), 7.40 (2H, m), 7.57 (2H, d, J=8 Hz), 7.70 (2H, d, J=8 Hz), 8.20 (1H, s), 9.20 (1H, s), 10.80 (1H, s); MS 565.11 (M+H).

PREPARATION OF INTERMEDIATE II

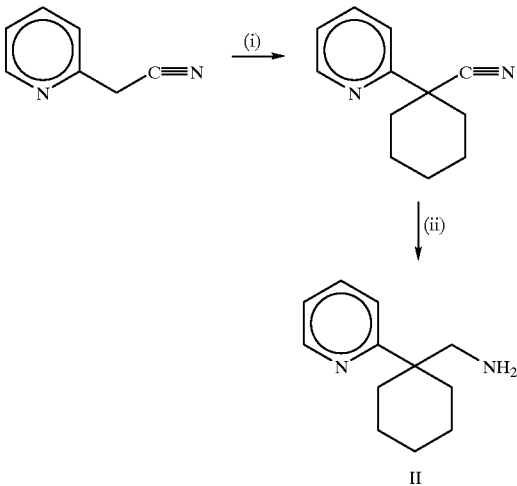

II

Reagents and Conditions:
i) Sodium hydride, 1,5-dibromopentane, DMSO, Et$_2$O, 15° C.
ii) Raney nickel, EtOH—NH$_3$, H$_2$, 50 psi, 40° C.

PREPARATION OF INTERMEDIATES

Synthesis of Intermediate II

Step 1

To a stirred suspension of sodium hydride (60% dispersed in oil) (4 g, 0.1 m) in DMSO (70 mL) under nitrogen at 15° C. was added dropwise a solution of 2-pyridyl acetonitrile (6 g, 51 mmol) and 1,5-dibromopentane (6.81 mL, 51 mmol) in ether (40 mL) and DMSO (10 mL) over 1 hour. The mixture was allowed to warm to room temperature and stirred for a further 24 hours under nitrogen. The reaction mixture was carefully quenched by the addition dropwise of isopropanol (10 mL), followed by water (100 mL) 10 minutes later. The reaction solution was taken up in EtOAc and washed with water. The aqueous layer was re-extracted with EtOAc, and the two organic layers were combined, dried (MgSO$_4$), and concentrated in vacuo. The residue was purified on silica with a gradient of heptane to 9:1 heptane/EtOAc to give 1-cyano-1-(2-pyridyl)cyclohexane (6.77 g, 72%).

$^1$H NMR (CDCl$_3$): δ 1.77–2.17 (10H, 2×m, cyclohexyl), 7.20–7.27 (1H, m, pyridyl H), 7.60–7.62 (1H, m, pyridyl H), 7.70–7.73 (1H, m, pyridyl H), 8.4–8.42 (1H, m, pyridyl H).

Intermediate II

Raney nickel (8 g) was washed with water to obtain pH 7 and then washed with ethanol to remove water (ensuring the catalyst was moist at all times). The Raney nickel was taken up in ethanolic ammonia (100 mL) and 1-cyano-1-(2-pyridyl)cyclohexane (6.7 g, 0.036 m) was added to the mixture which was then shaken on a Parr hydrogenation apparatus under 50 psi of hydrogen at 40° C. for 22 hours. The reaction mixture was filtered through Celite and concentrated in vacuo to give pure II as a clear oil (6.89 g, 100%).

$^1$H NMR: δ 1.20–1.65 (10H, m, cyclohexyl), 2.20–2.36 (2H, m, CH$_2$NH$_2$), 2.70–2.90 (2H, br s, NH$_2$), 7.00–7.20 (1H, m, ArH), 7.3–7.4 (1H, m ArH), 7.6–7.73 (1H, m, ArH), 8.6–8.7 (1H, m, ArH).

PREPARATION OF INTERMEDIATE III

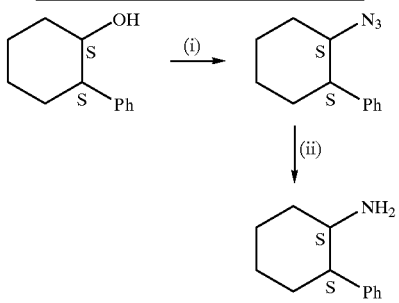

Reagents and Conditions:
i) DEAD, PPh$_3$, (PhO)$_2$PON$_3$, THF
ii) Lindlar, EtOH Synthesis of Intermediate III Step 1

A solution of diphenylposphonylazide (473 mg, 1.72 mmol) in THF (10 mL) was added dropwise over 20 minutes to a stirred solution of 1R,2S, trans-2-phenyl-1-cyclohexanol (303 mg, 1.72 mmol), triphenylphosphene (451 mg, 1.72 mmol), and diethyl ozodicarboxylate (300 mg, 1.72 mmol) in dry THF (10 mL) at room temperature. The resulting mixture was stirred for 3 days, then the solvent removed in vacuo. The product was purified by chromatography (silica, 10–20% ethyl acetate in heptane) to leave a clear oil A (217 mg, 63%).

$^1$H, NMR (CDCl$_3$): 1.34–2.4 (8H, m, 4×CH$_2$), 2.76–2.80 (1H, m, CH), 3.94 (1H, d, CH—N$_3$, J=2.8 Hz), 7.22–7.34 (5H, m, Ph);

IR (film): 3028, 2984, 2860, 2103, 1602, 1486, 1447; and 1267;

$$[\alpha] = \frac{18}{D} + 81.4°(c = 1.05, \text{acetone}).$$

Step 2

A (1.89 mg, 0.84 mmol) was hydrogenated in absolute ethanol (50 mL) at 30° C. and 45 psi over Lindlar catalyst (25 mg). The catalyst was filtered off and the solvent removed to yield an oil (130 mg, 79%).

$^1$H NMR (CDCl$_3$): 1.01 (2H, bs, NH$_2$), 1.35–2.06 (8H, m, 4×CH$_2$), 2.77–2.83 (1H, m, CH), 3.24–3.26 (1H, m, CHCH$_2$), 7.20–7.34 (5H, m, Ph);

IR (film): 3360, 3060, 3025, 2927, 2855, 1601, 1582, 1495, and 1447;

$$[\alpha]\frac{21}{D} + 72.9°(c = 1.04, \text{methanol}).$$

PREPARATION OF INTERMEDIATE XXI

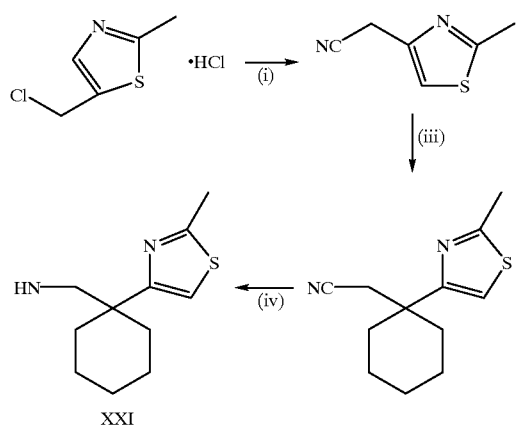

XXI

Reagents and Conditions:
(i) (a) EtOAc, NaHCO$_3$ (aq); (b) 95% Ethanol, water, potassium cyanide reflux
(ii) Sodium hydride, 1,5-dibromopentane, DMSO, Et$_2$O, room temperature, Ar
(iii) Raney Nickel, EtOH—NH$_3$, H$_2$, 50 psi, 35° C.

Synthesis of Intermediate XXI

Step 1

4-Chloromethyl-2-methyl thiazole hydrochloride (1 g, 5.4 mmol) was taken up in sodium bicarbonate saturated aqueous solution and extracted with EtOAc, dried (MgSO$_4$), and concentrated in vacuo. The residue was dissolved in 95% ethanol (50 mL) and potassium cyanide (353 mg, 5.4 mmol) followed by water (5 mL) were added to the reaction mixture. The mixture was refluxed for 18 hours and cooled to room temperature. The reaction mixture was taken up in EtOAc and washed with water, dried (MgSO$_4$), and concentrated in vacuo. The residue was purified on silica with a gradient of heptane to 1:1 heptane/EtOAc to give 4-cyanomethyl-2-methyl thiazole (180 mg, 24%).

$^1$H NMR (CDCl$_3$): δ 2.71 (3H, s, CH$_3$), 3.85 (2H, s, CH$_2$CN), 7.13 (1H, s, ArH);

IR (film): 2923.0, 2863.7, 2255.6, 1525.0, 1412.0, 1261.0, 1101.0, 1020.0, and 799.0 cm$^{-1}$;

MS m/e (ES$^+$) 139.06 (M+H$^+$).

Step 2 As for Intermediate II, Step 1

1-Cyano-1-(2-methyl thiazol-4-yl)cyclohexane isolated in 100% yield.

$^1$H NMR (CDCl$_3$): δ 1.70–2.00 (8H, mm, cyclohexyl), 2.12–2.20 (2H, m, cyclohexyl), 2.70 (3H, s, CH$_3$), 7.12 (1H, s, ArH);

IR (film): 2929.0, 2858.7, 1453.1, and 1227.0 cm$^{-1}$;

MS m/e (APCI) 207.12 (M+H$^+$) (100%).

Step 3 As for Intermediate II, Step 2

Intermediate XXI, 1-aminomethyl-1-(2-methyl thiazol-4-yl)cyclohexane was isolated in 98% yield.

$^1$H NMR (CDCl$_3$): δ 1.68–2.00 (8H, mm, cyclohexyl), 2.03–2.20 (4H, mm, 2 × cyclohexyl H, NH$_2$), 2.69 (2H, s, CH$_2$NH$_2$), 2.70 (3H, s, CH$_3$), 7.12 (1H, s, ArH);

IR (film): 2927.0, 2857.0, 2237.0, 1667.0, 1515.0, 1453.0, 1376.0, 1185.0, 1169.0, 1141.0, 957.0, and 745.0 cm$^{-1}$;

MS m/e (APCI) 211.15 (M+H$^+$), 207.13 (100%).

PREPARATION OF INTERMEDIATE XXII

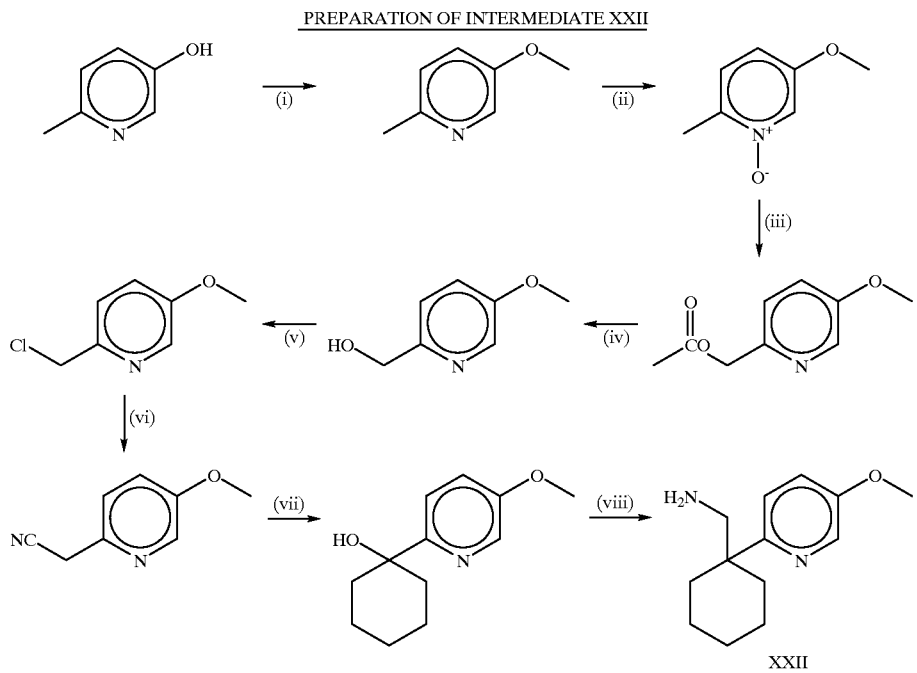

Reagents and Conditions:
(i) Sodium hydride, methyl iodide, DMF, 0° C.-room temperature under argon
(ii) M-chloro-peroxy-benzoic acid, sodium sulphate, DCM, room temperature
(iii) Acetic anhydride, reflux
(iv) Potassium hydroxide, methanol, reflux
(v) Thionyl chloride, DCM, reflux
(vi) Potassium cyanide, 95% ethanol, water, reflux
(vii) Sodium hydride, 1,5-dibromopentane, DMSO, $Et_2O$, room temperature, Ar
(viii) Raney Nickel, EtOH——$NH_3$, $H_2$, 57 psi, 35° C.

Synthesis of Intermediate XXII

Step 1

To a stirred suspension of sodium hydride (60% dispersed in oil) (1.8 g, 45 mmol) in DMF (60 mL) at 0° C. under argon was added a solution of 2-hydroxy- 5-methyl-pyridine (4.91 g, 45 mmol) in DMF (60 mL). Effervescence was observed, and the reaction mixture was allowed to warm to 18° C. Methyl iodide (2.8 mL, 45 mmol) was added to the reaction mixture which was allowed to warm to room temperature and stirred for 1 hour. The reaction mixture was quenched by the addition of isopropanol (20 mL), followed by water (20 mL) 30 minutes later, under argon. The reaction mixture was taken up in EtOAc and washed with $NaHCO_3$ (aq), dried ($MgSO_4$), and concentrated in vacuo to give 2-methoxy-pyridine as a pure volatile liquid (2.93 g, 53%).

$^1$H NMR ($CDCl_3$): δ 2.49 (3H, s, $CH_3$—C), 3.83 (3H, s, $OCH_3$, 7.05–7.13 (2H, mm, pyridyl H4 and 5), 8.19 (1H, d, J=2.8 Hz, pyridyl H2);

IR (film): 2924.0, 2854.0, 1575.0, 1497.0, 1464.0, 1378.0, 1270.0, 1243.0, 1211.0, and 1034.0 cm$^{-1}$.

Step 2

To a solution of 2-methyl-5-methoxy-pyridine (2.93 g, 24 mmol) in DCM (100 mL) was added sodium sulphate (5 g, 35 mmol), followed by m-chloro-peroxy-benzoic acid (10 g, 58 mmol), and mixture was stirred at room temperature for ~48 hours. The reaction mixture was filtered, and the white solid was washed with DCM. The filtrate was concentrated and purified by normal phase chromatography eluting with a gradient of 1:1 EtOAc/heptane to EtOAc to give 2-methyl-5-methoxy-pyridine-N-oxide (2.41 g, 72%).

$^1$H NMR (DMSO): δ 2.27 (3H, s, C—$CH_3$), 3.79 (3H, s, $OCH_3$), 6.96 (1H, dd, J=2.4 and 8.8 Hz, pyridyl H5), 7.36 (1H, d, J=8.8 Hz, pyridyl H4), 8.08 (1H, d, J=2.4 Hz, pyridyl H2);

IR (film): 3386.0, 1616.0, 1566.0, 1516.0, 1452.0, 1375.0, 1304.0, 1197.0, 1172.0, 1131.0, 1030.0, 996.0, and 960.0 cm$^{-1}$;

MS m/e (ES) 140 (M+H$^+$).

Step 3

A mixture of 2-methyl-5-methoxy-pyridyl-N-oxide (1.082 g, 7.8 mmol) and acetic anhydride (excess, 5 mL) was gently warmed to reflux for 10 minutes. The reaction mixture was allowed to cool to room temperature before being taken up in EtOAc, washed ($NaHCO_3$ (aq)), dried ($MgSO_4$), and concentrated in vacuo to give crude 2-acetoxy-methyl-5-methoxy-pyridine which was taken through to the next step without further purification.

$^1$H NMR ($CDCl_3$): δ 2.13 (3H, s, $\text{OC}\underline{\text{CH}}_3$), 3.87 (3H, s, $\underline{CH_3}$O), 5.16 (2H, s, $\underline{CH_2}$OC), 7.20 (1H, dd, J=3.2 and 8.8 Hz, pyridyl H), 7.30 (1H, d, J=8.4 Hz, pyridyl H), 8.30 (1H, d, J=3.2 Hz, pyridyl H);

IR (film): 2943.0, 1740.0, 1576.0, 1499.0, 1377.0, 1293.0, 1227.0, and 1029.0 cm$^{-1}$;

MS m/e (ES) 182.16 (100%) (M+H$^+$).

Step 4

To a stirred solution of 2-acetoxy-methyl-5-methoxy-pyridine (1.41 g, 7.8 mmol) in methanol (30 mL) was added excess potassium hydroxide (1.6 g), and the mixture was refluxed for 2 hours. The solvent was removed in vacuo, and the residue was purified by column chromatography eluting with a heptane to ethyl acetate gradient. The extremely volatile 2-hydroxy-methyl-5-methoxy-pyridine was obtained as a solution in ethyl acetate (0.68 g, 63% yield).

$^1$H NMR (CDCl$_3$): δ 3.87 (3H, s, OCH$_3$), 4.70 (2H, s, CH$_2$OH), 7.18–7.24 (2H, m, pyridyl H4 and 5), 8.25 (1H, d, J=1.8 Hz, pyridyl H2);

IR (film): 3346.0, 1575.0, 1499.0, 1271.0, 1210.0, and 1028.0 cm$^{-1}$;

MS m/e (ES) 140.18 (M+H$^+$).

Step 5

To a solution of 2-hydroxy-methyl-5-methoxy-pyridine (0.68 g, 4.9 mmol) in dry DCM was added dropwise excess thionyl chloride (2.0 mL), and the mixture was refluxed for 2 hours. The solvent was removed in vacuo, and the residue was taken up in EtOAc and washed with NaHCO$_3$ (aq), dried (MgSO$_4$, and concentrated in vacuo. The extremely volatile 2-chloromethyl-5-methoxy-pyridine was obtained as a solution in ethyl acetate to give (984.0 mg, 83.5%) yield.

$^1$H NMR (CDCl$_3$): δ 3.87 (3H, s, OCH$_3$), 4.65 (2H, s, CH$_2$Cl), 7.21 (1H, dd, J=2.8 and 8.4 Hz, pyridyl H4), 7.39 (1H, d, J=8.4 Hz, pyridyl H5), 8.27 (1H, d, J=2.8 Hz, pyridyl H2);

IR (film): 3337.1, 2930.0, 2854.7, 1731.3, 1639.5, 1537.0, 1423.2, 1301.9, and 1158.0 cm$^{-1}$;

MS m/e (ES) 158.15 (M+H$^+$) (100%).

Step 6 As for Intermediate XXI, Step 1

2-Cyanomethyl-5-methoxy-pyridine was isolated in 73% pure yield.

$^1$H NMR (CDCl$_3$): δ 3.87 (3H, s, OCH$_3$), 3.88 (2H, s, CH$_2$CN), 7.22 (1H, dd, J=3.2 and 8.8 Hz, pyridyl H4), 7.34 (1H, dd, J=0.4 and 8.4 Hz, pyridyl H5), 8.27 (1H, d, J=2.8 Hz, pyridyl H2);

IR (film): 2922.8, 1575.5, 1496.0, and 1271.5 cm$^-$;

MS m/e (APCI) 149.18 (M+H$^+$) (100%).

Step 7 As for Intermediate II, Step 1

-1-Cyano-1-(4-methoxypyrid-2-yl)cyclohexane was isolated in 60% yield.

NMR (CDCl$_3$): δ 1.76–2.12 (10H, mm, cyclohexyl), 3.87 (3H, s, OCH$_3$), 7.21 (1H, dd, J=2.8 and 8.8 Hz, pyridyl H4), 7.51 (1H, dd, J=0.8 and 9.6 Hz, pyridyl H5), 8.29 (1H, d, 3.2 Hz, pyridyl H2);

IR (film): 2935.0, 2863.7, 1575.0, 1478.0, 1299.0, 1269.0, 1244.0, and 1017.0 cm$^{-1}$;

MS m/e (ES) 217.16 (M+H$^+$).

Step 8 As for Intermediate II, Step 2

Intermediate XXII, 1-amino-methyl-1-(4-methoxy-pyrid-2-yl)cyclohexane was isolated in 82% yield.

$^1$H NMR (DMSO): δ 1.13–1.58 (8H, mm, cyclohexyl), 2.14–2.22 (2H, m, cyclohexyl), 2.56 (2H, s, NH$_2$CH$_2$), 3.80 (3H, s, OCH$_3$), 7.30 (2H, m, pyridyl H4 and H5), 8.26 (1H, m, pyridyl H2);

IR (film): 2925.0, 2858.6, 1569.4, and 1477.8 cm$^{-1}$;

MS m/e (APCI) 221.14 (M+H$^+$).

PREPARATION OF INTERMEDIATE XXIII

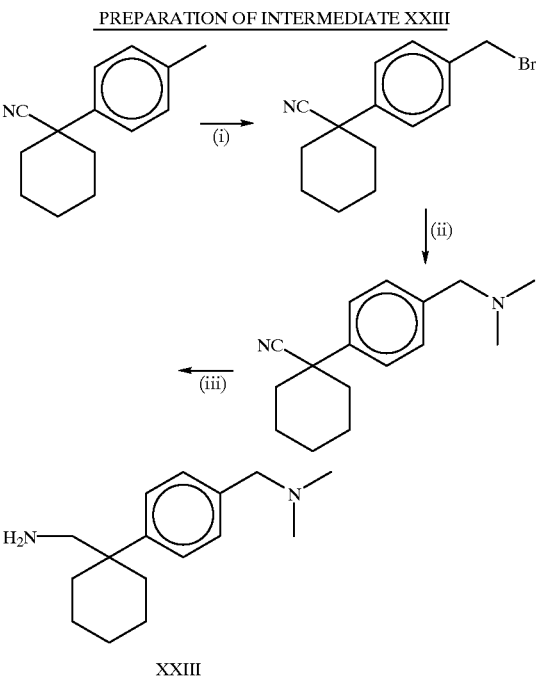

Reagents and Conditions:
(i) N-Bromo-succinimde, benzoyl peroxide, carbon tetrachloride, room temperature under argon
(ii) Dimethyl amine, DCM, room temperature
(iii) Raney Nickel, EtOH•NH$_3$, 50 psi, 30° C.

Synthesis of Intermediate XXIII

Step 1

To a solution of 1-(4-methyl-phenyl)-1-cyclohexyl-carbonitrile (2 g, 0.01 m) in CCl$_4$ (20 mL) under argon at room temperature was added N-bromo-succinimide (1.96 g, 0.011 m) followed by benzoyl peroxide (30% water) (2.3 mg, 1.6 mmol) in CCl$_4$ (10 mL), and the reaction mixture was refluxed for 5 hours. The mixture was cooled to room temperature, filtered, washed with DCM, and concentrated in vacuo. The residue was purified by normal phase chromatography eluting with a gradient of heptane to 10% EtOAc:heptane to give the bromide (2.57 g, 92%).

$^1$H NMR (CDCl$_3$): δ 1.71–1.86 (8H, mm, cyclohexyl), 2.14 (2H, d, J=11.96 Hz, cyclohexyl), 4.49 (2H, s, CH$_2$—Br), 7.41 (2H, d, J=8.54 Hz, 2ArH), 7.47 (2H, d, J=8.06 Hz, 2ArH);

IR (film): 2936.0, 2860.0, 2232.0, 1914.0, 1789.0, 1765.0, 1610.0, 1515.0, 1451.0, 1415.0, 1355.0, and 1231.0 cm$^{-1}$.

Step 2

To a stirred solution of 1-(4-bromomethyl-phenyl)-1-cyclohexyl-carbonitrile (0.89 g, 3.2 mmol) in DCM (30 mL) under argon at room temperature was added dimethylamine (2M in THF) (6.42 mL, 12.8 mmol), and the reaction mixture was stirred for 20 hours at room temperature. 1N NaOH (aq) (15 mL) was added to the reaction mixture, and the solution was stirred for 10 minutes. The reaction mixture was taken up in water and extracted with DCM, dried and concentrated in vacuo. The residue was purified on silica (normal phase) eluting with a gradient of heptane to ethyl acetate to give the dimethylamine in 76% yield (593 mg).

$^1$H NMR (CDCl$_3$): δ 1.72–1.88 (8H, m, cyclohexyl), 2.15 (2H, d, J=11.71, cyclohexyl), 2.24 (2H, s, N(CH$_3$)$_2$), 3.4 (2H, s, CH$_2$NMe$_2$), 7.32 (2H, d, J=8.3 Hz, 2ArH);

IR (film): 3375.0, 2932.9, 2859.7, 1645.8, 1455.6, and 1042.0 cm$^{-1}$;

MS m/e (APCI) 243.2 (M+H$^+$).

Step 3 As for Intermediate II, Step 2

Intermediate XXIII, 1-aminomethyl-1-[4-(N,N-dimethylaminomethyl)-phenyl]cyclohexane was isolated in quantitative yield.

$^1$H NMR (CDCl$_3$): δ 1.22–1.63 (8H, mm, cyclohexyl), 2.07–2.17 (2H, m, cyclohexyl), 2.25 (6H, s, N(CH$_3$)$_2$), 2.68 (2H, s, CH$_2$NH$_2$), 3.41 (2H, s, ArCH$_2$NMe$_2$), 7.27 (4H, 2 x d, J=6.8 Hz, 4 x ArH);

IR (film): 2931.0, 2856.0, 2814.0, 2766.0, 1513.0, and 1455.0 cm$^{-1}$;

MS m/e (ES) 247 (M+H$^+$).

PREPARATION OF INTERMEDIATE XXIV

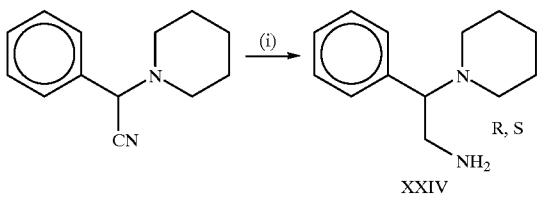

Reagents and Conditions:
(i) Lithium aluminum hydride/aluminum chloride, Et$_2$O THF 0° C.

SYNTHESIS OF INTERMEDIATE XXIV

Step 1

To an ice-cold solution of Et$_2$O (30 mL) under nitrogen was added aluminum chloride (0.5 g, 3.74 mmol), with stirring, over 2 minutes. This solution was added to an ice-cold solution of lithium aluminum hydride, 1M in Et$_2$O (3.74 mL, 3.74 mmol) in anhydrous THF (50 mL) stirring under nitrogen. The reducing solution was allowed to warm to room temperature before gradually adding alpha-(1-piperidino)phenylacetonitrile (0.75 g, 3.74 mmol) dissolved in THF (20 mL). The reaction mixture was stirred for 3 hours before cooling and adding a 1:1 mixture of H$_2$O/THF. Fifty percent aqueous postassium hydroxide (20 mL) was added producing two layers. The organic layer was separated, dried (K$_2$CO$_3$), and concentrated in vacuo. The residue was purified on silica eluting with a gradient of DCM to 25% MEOH/DCM to give pure XXIV as a white oil (0.47 g, 62%).

$^1$H NMR (CDCl$_3$): δ1.28–1.40 (2H, m, piperidino CH's), 1.48–1.63 (4H, m, piperidino CH's), 2.17–2.51 (6H, m, NH$_2$ and 4 piperidino CH's), 2.99–3.04 (1H, m, CHCHHNH$_2$), 3.19–3.24 (1H, m, CHCHHNH$_2$), 3.45–3.48 (1H, m, CHCH$_2$NH), 7.20–7.37 (5H, m, ArH);

IR (film): 293.0, 2853.0, 2804.0., 1492.0, 1452.0, 1158.0, 1104.0, and 765.0 cm$^{-1}$;

MS me/(ES+) 205.2 (M+H$^+$, 100%).

PREPARATION OF INTERMEDIATE XXV

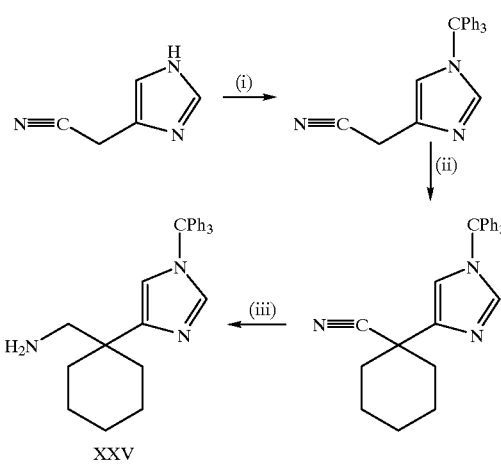

XXV

Reagents and Conditions:
(i) Triphenylmethylchloride, triethylamine, DMF, room temperature
(ii) Sodium hydride, 1,5-dibromopentane, DMSO, room temperature
(iii) Lithium aluminum hydride/aluminum chloride, Et$_2$O, THF, 0° C.

SYNTHESIS OF INTERMEDIATE XXV

Step 1

To a stirred solution of 4-cyanomethlimidazole (2.24 g, 20.9 mmol) in DMF (50 mL) was added triphenylmethyl-chloride (6.42 g, 23.0 mmol) and triethylamine (2.12 g, 20.9 mmol). The reaction mixture was stirred at room temperature overnight. The DMF was evaporated in vacuo and the residue taken up in ethyl acetate (100 mL). The resulting white solid was filtered off and discarded. The filtrate was evaporated in vacuo and purified on silica with a gradient of heptane to 2:5 heptane/EtOAc to give the desired product (6.52 g, 89%).

$^1$H NMR (CDCl$_3$): δ3.69 (2H, s, CH$_2$N), 6.84 (1H, d, 1.0 Hz, imidazole CH), 7.10–7.15 (6H, m, 6 ArH), 7.32–7.37 (9H, m, 9 ArH), 7.41 (1H, d, 1.5 Hz, imidazole CH);

IR (film): 3059, 1597, 1493, 1445, 1412, 1240, 1187, 1156, 1120, 1087 1037, 991, 907, 871,and 751 cm$^{-1}$;

Analysis C$_{24}$H$_{19}$N$_3$: C, H, N;

mp 139–142° C.

Step 2 As for Intermediate II, Step 1 The desired compound was isolated in 63% yield.

$^1$H NMR (CDCl$_3$): δ1.20–1.35 (1H, m , cyclohexyl CH), 1.65–1.90 (7H, m, cyclohexyl CH), 2.13–2.18 (2H, m, cyclohexyl CH), 6.82 (1H, d, 1.5 Hz, imidazole CH), 7.09–7.50 (6H, m, ArH), 7.30–7.36 (9H, m , ArH), 7.39 (1H, d, 1.0 Hz, imidazole CH);

IR (film): 3060, 2934, 2859, 2233, 1492, 1446, 1161, 1134, 1036, 974, 907, 832, and 747 cm$^{-1}$;

MS (ES$^+$) 418.5 (M$^+$+H);

Analysis C$_{29}$H$_{27}$N$_3$: C, H, In;

mp 184–186° C.

Step 3 As for Intermediate XXIV, Step 1 The intermediate XXV was isolated in 73% yeild.

$^1$H NMR (CDCl$_3$): 1.10–1.70 (2H, br s, NH$_2$), 1.26–1.52 (8H, m, cyclohexyl CH), 1.95–1.99 (2H, m, cyclohexyl CH), 2.67 (2H, s, CH$_2$NH$_2$), 6.54 (1H, d, 1.6 Hz, imidazole (CH), 7.12–7.17 (6H, m, ArH), 7.31–7.35 (9H, m, ArH), 7.41 (1H, d, 1.6 Hz, imidazole CH);

IR (film): 3374, 3059, 2927, 2852, 1598, 1493, 1445, 1324, 1231, 1184, 1118, 1087, 1036, 906, 870, 825, and 747 cm$^{-1}$.

What is claimed is:

1. A compound of Formula I

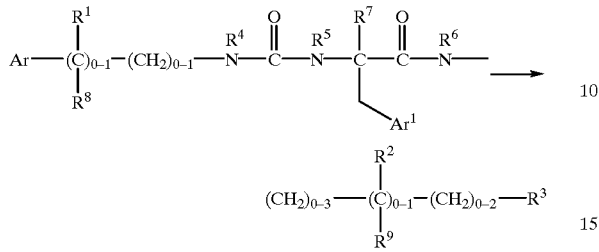

or a pharmaceutically acceptable salt thereof wherein

Ar is phenyl or pyridyl unsubstituted or substituted from 1 to 3 sustituents selected from alkyl, halogen, alkoxy, nitro, amino, $NH_2CH_2$-, cyano, $CF_3$, —$NHCONH_2$, and $CO_2R^1$;

$R^1$ is hydrogen or straight, branched, or cyclic alkyl of from 1 to 7 carbon atoms;

$R^8$ is hydrogen or forms a ring with $R^1$ of from 3 to 7 carbon atoms;

$R^2$ is hydrogen or straight, branched, or cyclic alkyl of form 1 to 8 carbon atoms;

$R^9$ is hydrogen or forms a ring of from 3 to 7 carbon atoms with $R^2$;

$Ar^1$ can be independently selected from Ar and can also include pyridyl-N-oxide, indolyl, pyridyl, and imidazole;

$R^4$, $R^5$, $R^6$, and $R^7$ are each independently selected from hydrogen and methyl;

$R^3$ can be independently selected from Ar or is hydrogen, hydroxy, $NMe_2$, N-methyl-pyrrole,

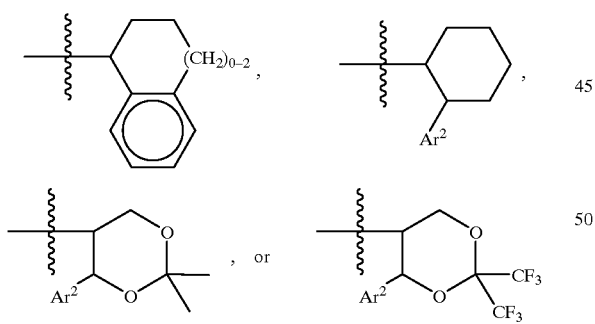

wherein $Ar^2$ is phenyl or pyridyl with the proviso that when $Ar^1$ is phenyl, said phenyl is substituted; —$[CR^1(R^8)]_{0-1}$—$(CH_2)_{0-1}$— is not —$(CH_2)_{1-2}$; and —$(CH_2)_{0-3}$—$[CR^2(R^9)]_{0-1}$—$(CH_1)_{0-2}$— is not —$(CH_2)_{1-6}$—.

2. A compound according to claim 1 wherein

Ar is phenyl unsubstituted or substituted with 1 or 2 substituents selected from isopropyl, chloro, nitro, and cyano;

$R^2$ forms a ring of form 5–7 carbon atoms with $R^9$;

$R^4$, $R^5$, and $R^6$ are hydrogen;

$R^7$ is methyl or hydrogen; $R^3$ is 2-pyridyl or hydroxy; and $Ar^1$ is indolyl, pyridyl, pyridyl-N-oxide, and imidazolyl.

3. A compound according to claim 1 wherein

Ar is unsubstituted phenyl;

$R^1$ is cyclopentyl or tert-butyl;

$R^4$ and $R^5$ are hydrogen;

$R^7$ is methyl;

$R^6$ is hydrogen;

$R^3$ is phenyl with two isopropyl substituents, unsubstituted phenyl, or

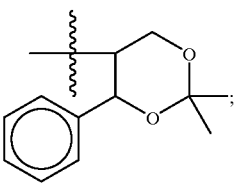

and $Ar^1$ is indolyl.

4. A compound according to claim 1 wherein

Ar is 2,6-diisopropyl-phenyl, 4-nitrophenyl, and 4-cyanophenyl;

$R^4$, $R^5$, and $R^6$ are hydrogen;

$R^7$ is methyl;

$R^2$ is hydrogen or forms a ring of 6 carbon atoms with $R^9$;

$R^3$ is hydroxyl, 2-pyridyl,

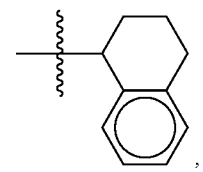

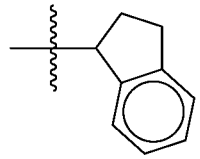

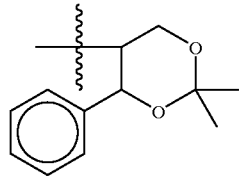

and $Ar^1$ is indolyl, pyridyl-N-oxide, pyridyl.

5. A compound according to claim 1 and selected from:

N-Cyclohexylmethyl-2-[3-(2,6-diisopropyl-phenyl)-ureido ]-3-(1H-indol-3-yl)-2-methyl-propionamide;

N-Cyclohexylmethyl-2-[3-(2,6-diisopropyl-phenyl)-ureido ]-3-(1H-indol-3-yl)-N-methyl-propionamide;

N-Cyclohexylmethyl-2-[3-(2,6-diisopropyl-phenyl)-1-methyl-ureido ]-3-(1H-indol-3-yl)-propionamide.

6. A compound according to claim 4 and selected from:

2-[3-(2,6-Diisopropyl-phenyl)-ureido ]-2-methyl-3-(1-oxy-pyridin-2-yl)-N-(1-pyridin-2-yl-cyclohexylmethyl)-propionamide; and 2-[3-(2,6-Diisopropyl-phenyl)-ureido ]2-methyl-3-pyridin-2-yl-N-(1-pyridin-2-yl-cyclohexylmethyl)-propionamide.

7. A compound according to claim 1 and selected from:

N-Cyclohexylmethyl-2-[3-(2,6-dissopropyl-phenyl) ureido ]-3-(1H-indol-3-yl)-2-methyl-propionamide;

N-Cyclohexylmethyl-2-[3-(2,6-diisopropyl-phenyl) ureido ]-3-(1H-indol-3-yl)-N-methyl-propionamide;

N-Cyclohexylmethyl-2-[3-(2,6-diisopropyl-phenyl)-3-methyl-ureido ]-3-(1H-indol-3-yl)-2-methyl-propionamide;

N-Cyclohexylmethyl-2-[3-(2,6-diisopropyl-phenyl)-1-methyl-ureido ]-3-(1H-indol-3-yl)-propionamide;

2-[3-(2,6-Diisopropyl-phenyl)-ureido ]-2-methyl-3-(1-oxy-pyridin-2-yl)-N-(1-pyridin-2-yl-cyclohexylmethyl)-propionamide;

2-[3-(2,6-Diisopropyl-phenyl)-ureido ]-2-methyl-3-pyridin-2-yl-N-(1-pyridin-2-yl-cyclohexylmethyl)-propionamide;

2-[3-(2,6-Diisopropyl-phenyl)-ureido ]-2-methyl-N-(1-pyridin-2-yl-cyclohexylmethyl)-3-(2-trifluoromethyl-phenyl)-propionamide;

2-Methyl-3-(2-nitro-phenyl)-2-[3-(4-nitro-phenyl)-ureido ]-N-(1-pyridin-2-yl-cyclohexylmethyl)-propionamide;

2-[3-(2,6-Diisopropyl-phenyl)-ureido ]-3-(1H-imidazol-4-yl)-N-(1-pyridin-2-yl-cyclohexylmethyl)-propionamide;

N-Cyclohexylmethyl-2-[3-(2,6-dimethyoxy-phenyl) ureido ]-3-(1H-indol-3-yl)-2-methyl-propionamide;

3-(1H-Indol-3-yl)-2-methyl-2-{3-[1-(4-nitro-phenyl)-ethyl ]-ureido}-N-(1-pyridin-2-yl-cyclohexylmethyl)-propionamide;

3-(1H-Indol-3-yl)-2-methyl-2-[3-(4-nitro-phenyl)-ureido ]-N-(1-pyridin-2-yl-cyclohexylmethyl)-propionamide;

4-(3-{2-(1H-Indol-3-yl)-1-methyl-1- [(1-pyridin-2-yl-cyclohexylmethyl)-carbamoyl ]-ethyl}-ureido)-benzoic acid ethyl ester;

3-(1H-Indol-3-yl)-2-methyl-N-(1-pyridin-2-yl-cyclohexylmethyl)-2- [3-(4-trifluoromethylphenyl)-ureido]-propionamide;

2-[3-(4-Cyano-phenyl)-ureido ]-3-(1H-indol-3-yl)-2-methyl-N-(1-pyridin-2-yl-cyclohexylmethyl)-propionamide;

N-Cyclohexylmethyl-3-(1H-indol-3-yl)-2-methyl-2-[3-(4-nitro-phenyl)-ureido ]-propionamide; and N-(1-Hydroxy-cyclohexylmethyl)-3-(1H-indol-3-yl)-2-methyl-2- [3-(4-nitro-phenyl)-ureido]-propionamide.

8. A compound according to claim 1 and named:

(S)-N-(2,6-Diisopropyl-phenyl)-2-[3-(2,2-dimethyl-1-phenyl-propyl)-ureido ]3-(1H-indol-3-yl)-propionamide.

9. A compound according to claim 1 and selected from:

2-[3-(2,6-Diisopropyl-phenyl)-ureido ]-N-(2,2-dimethyl-4-phenyl-[1, 3]dioxan-5-yl)-3-(1H-indol-3-yl)-2-methyl-propionamide;

N-(2-Cyclohexyl-ethyl)-2-[3-(2,6-diisopropyl-phenyl)-ureido ]-3-(1H-indol-3-yl)-2-methyl-propionamide;

2-[3-(2,6-Diisopropyl-phenyl)-uriedo ]-3-(1H-indol-3-yl)-2-methyl-propionamide;

2-[3-(2,6-Diisopropyl-phenyl)-ureido ]-3-(1H-indol-3-yl)-2-methyl-N-(,2,3,4-tetrahydro-naphthalen-1-yl)-propionamide;

2-[3-(2,6-Diisopropyl-phenyl)-ureido ]-3-(1H-indol-3-yl)-2-methyl-N-(2-phenyl-cyclohexyl)-propionamide;

2-[3-(2,6-Diisopropyl-phenyl)-ureido ]-N-indan-1-yl-3-(1H-indol-3-yl)-2-methyl-propionamide; and 2-[3-(2,6-Diisopropyl-phenyl)-ureido ]-3-(1H-indol-3-yl)-2-methyl-N-(1-pyridin-2-yl-cyclohexylmethyl)-propionamide.

10. A pharmaceutical composition comprising a therapeutically effective amount of a compound according to claim 1 in combination with a pharmaceutically acceptable carrier.

11. A method of antagonizing the effects of neuromedin B and/or gastrin-releasing peptide at bombesin receptors which comprises administering a compound according to claim 1 to a patient.

12. A method of treating depression in a patient in need of said treatment comprising administering a therapeutically effective amount of a compound according to claim 1.

13. A method of treating seasonal affective disorders in a patient in need of said treatment comprising administering a therapeutically effective amount of a compound according to claim 1.

14. A method of treating feeding disorders in a patient in need of said treatment comprising administering therapeutically effective amount of a compound according to claim 1.

15. A method of treating gastrointestinal disorders in a patient in need of said treatment comprising administering a therapeutically effective amount of a compound according to claim 1.

16. A method of treating sleeping disorders in a patient in need of said treatment comprising administering a therapeutically effective amount of a compound according to claim 1.

17. A method treating memory impairment in a patient in need of said treatment comprising administering a therapeutically effective amount of a compound according to claim 1.

18. A method of treating cancer in a patient in need of said treatment comprising administering a therapeutically effective amount of a compound according to claim 1.

19. A method of treating small cell lung carcinoma in a patient in need of said treatment comprising administering a therapeutically effective amount of a compound according to claim 1.

20. A method of treating psychoses in a patient in need of said treatment comprising administering a therapeutically effective amount of a compound according to claim 1.

* * * * *

UNITED STATES PATENT AND TRADEMARK OFFICE
CERTIFICATE OF CORRECTION

PATENT NO.   : 6,194,437 B1
DATED        : February 27, 2001
INVENTOR(S)  : Horwell et al.

It is certified that error appears in the above-identified patent and that said Letters Patent is hereby corrected as shown below:

Column 65,
Line 31, "form" should read -- from --.
Lines 58 to 59, at the end "and -(CH2)0.3-[CR2(R9)]0-1-(CH1)0-2-" should read -- and -(CH2)0-3-[CR2(R9)]0-1-(CH2)0-2- --
Line 65, middle of line: "form" should read -- from --.

Column 67,
Line 27, after "(2,6-": "dimethyoxy" should read -- dimethoxy --.

Column 68,
Line 6, after "N-": "(,2,3,4-" should read -- (1,2,3,4- --.
Line 41, "A method treating" should read -- A method of treating --.

Signed and Sealed this

Fifth Day of August, 2003

JAMES E. ROGAN
*Director of the United States Patent and Trademark Office*